United States Patent
Wang

(10) Patent No.: US 11,192,901 B2
(45) Date of Patent: Dec. 7, 2021

(54) NITROGEN-CONTAINING HETEROCYCLIC ORGANIC COMPOUND AND ORGANIC ELECTROLUMINESCENT DEVICE

(71) Applicant: SHENZHEN CHINA STAR OPTOELECTRONICS SEMICONDUCTOR DISPLAY TECHNOLOGY CO., LTD., Guangdong (CN)

(72) Inventor: Shipan Wang, Shenzhen (CN)

(73) Assignee: SHENZHEN CHINA STAR OPTOELECTRONICS SEMICONDUCTOR DISPLAY TECHNOLOGY CO., LTD., Guangdong (CN)

( * ) Notice: Subject to any disclaimer, the term of this patent is extended or adjusted under 35 U.S.C. 154(b) by 277 days.

(21) Appl. No.: 16/615,453

(22) PCT Filed: Jul. 25, 2019

(86) PCT No.: PCT/CN2019/097700
§ 371 (c)(1),
(2) Date: Nov. 21, 2019

(87) PCT Pub. No.: WO2021/007882
PCT Pub. Date: Jan. 21, 2021

(65) Prior Publication Data
US 2021/0332066 A1    Oct. 28, 2021

(30) Foreign Application Priority Data
Jul. 17, 2019 (CN) .......................... 201910646891.0

(51) Int. Cl.
*C07D 519/00* (2006.01)
*H01L 51/00* (2006.01)
*H01L 51/50* (2006.01)

(52) U.S. Cl.
CPC ........ *C07D 519/00* (2013.01); *H01L 51/0061* (2013.01); *H01L 51/0072* (2013.01); *H01L 51/0094* (2013.01); *H01L 51/5016* (2013.01)

(58) Field of Classification Search
CPC .. C07D 519/00; C07D 498/04; C07D 495/04; C07D 413/04; C07D 417/04; H01L 51/00; H01L 51/50; A01N 43/72; C07F 5/025
See application file for complete search history.

(56) References Cited

U.S. PATENT DOCUMENTS

2009/0156572 A1* 6/2009 Ikeura .................. A61P 1/00 514/210.02
2010/0029690 A1* 2/2010 Atobe .................. A61K 31/44 514/256

(Continued)

*Primary Examiner* — Dung A. Le
(74) *Attorney, Agent, or Firm* — Benesch, Friedlander, Coplan & Aronoff LLP

(57) ABSTRACT

A nitrogen-containing heterocyclic organic compound and an organic electroluminescent device are provided. The nitrogen-containing heterocyclic organic compound has a structure represented by the following general formula (I):

Formula (I)

(Continued)

and

X is N or CH; Y is a single bond, O, S, an imino, a methylene, a methylidenesilane group, a substituted imino, a substituted methylene, or a substituted methylidenesilane group, the substituents in the substituted imino, and the substituted methylene; L, $Ar_1$, and $Ar_2$ are each independently selected from one of a $C_6$-$C_{30}$ aryl, a $C_3$-$C_{30}$ heteroaryl, a substituted $C_6$-$C_{30}$ aryl, and a substituted $C_3$-$C_{30}$ heteroaryl; n is an integer from 0 to 3; $R_1$ to $R_8$ are each independently selected from one of a hydrogen, a deuteron, a halogen, a $C_1$-$C_{30}$ alkyl, a $C_1$-$C_{30}$ alkyl substituted with a heteroatom, a $C_6$-$C_{30}$ aryl, and a $C_3$-$C_{30}$ heteroaryl.

10 Claims, 2 Drawing Sheets

(56) References Cited

U.S. PATENT DOCUMENTS

| 2010/0168418 A1* | 7/2010 | Kiyoto | C07D 405/14 544/51 |
| 2011/0136782 A1* | 6/2011 | Mitani | C07D 498/04 514/211.1 |
| 2011/0178060 A1* | 7/2011 | Shirai | A61P 25/22 514/210.18 |

* cited by examiner

NITROGEN-CONTAINING HETEROCYCLIC ORGANIC COMPOUND AND ORGANIC ELECTROLUMINESCENT DEVICE

BACKGROUND OF INVENTION

Field of Invention

The present invention relates to a field of electroluminescent materials, and more particularly, to a nitrogen-containing heterocyclic organic compound and an organic electroluminescent device.

Description of Prior Art

Recently, organic light-emitting diodes (OLEDs) have characteristics such as self-luminous, large viewing angles, wide color gamut, low energy consumption, high efficiency, fast response times, being lighter and thinner, and a flexible display, and thus have great application prospects in the fields of full color display and solid state lighting. Currently, the development of organic electroluminescent devices is critically limited by the properties of organic electroluminescent materials. Therefore, many researches are focused on developing an organic electroluminescent material having high stability and efficiency.

Optoelectronic materials being organic small molecules have been widely developed to use as high performance materials, since they have advantages such as having clear structure and easy to be modified, processed and purified. According to the statistics rule of quantum spin, the ratio of singlet excitons to triplet excitons generated by conventional fluorescent materials is 1:3. Conventional fluorescent materials can only use 25% of singlet excitons to emit light, and quantum efficiency is not high (less than 5%). Organic phosphorescent materials can emit light by singlet exciton or triplet exciton due to the spin-orbit coupling of heavy metal atoms. Theoretically, the internal quantum efficiency can achieve 100%. However, the noble metals such as ruthenium and platinum are necessary for using organic phosphorescent materials, and such resources are limited and expensive. Further, the stability of blue phosphorescent materials is poor.

Being noble metal-free, pure organic small molecule materials, having a relatively low single-triplet level difference ($\Delta E_{ST}$), thermally activated delayed fluorescence (TADF) materials have a molecular structure of electron donor group combined with electron acceptor group. Therefore, the triplet excitons of TADF materials can be transformed into singlet excitons by reverse intersystem crossing (RISC) under environmental heat. Hence, their internal quantum efficiency can theoretically achieve 100%.

TADF materials are developed as novel electroluminescent materials and have great application prospects due to their advantages of high quantum efficiency and low production cost. However, there is only a few TADF materials, and their properties should be improved. Therefore, there is still an unmet need for more TADF materials having higher properties.

SUMMARY OF INVENTION

The purpose of the present invention is to provide a nitrogen-containing heterocyclic organic compound as a novel organic electroluminescence compound of donor-acceptor (D-A) type. The compound's highest occupied molecular orbital (HOMO) and lowest unoccupied molecular orbital (LUMO) are distributed on the donor group and the acceptor group, respectively, and there is less overlap between HOMO and LUMO, such that the compound has a property of thermally activated delayed fluorescence and can be used as a light emitting material in the organic electroluminescent device.

Another purpose of the present invention is to provide an organic electroluminescent device, in which the organic functional layer includes the above nitrogen-containing heterocyclic organic compound and has an excellent luminescent property.

For the above purposes, the present invention provides a nitrogen-containing heterocyclic organic compound, having a chemical structure represented by the following formula (I):

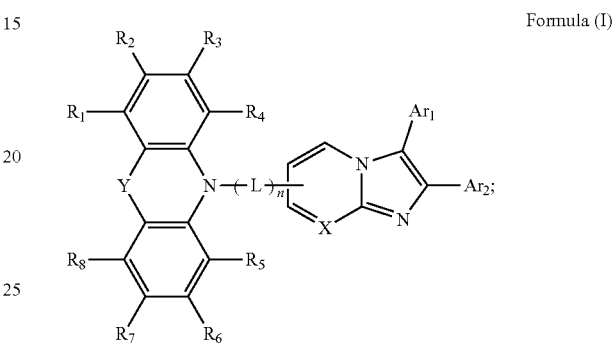

Formula (I)

and

X is N or CH;

Y is a single bond, O, S, an imino, a methylene, a methylidenesilane group, a substituted imino, a substituted methylene, or a substituted methylidenesilane group, the substituents in the substituted imino, the substituted methylene, and the substituted methylidenesilane group are each independently selected from one of a hydrogen, a deuteron, a $C_1$-$C_{30}$ alkyl, a $C_1$-$C_{30}$ alkyl substituted with a heteroatom, a $C_6$-$C_{30}$ aryl, and a $C_3$-$C_{30}$ heteroaryl;

L, $Ar_1$, and $Ar_2$ are each independently selected from one of a $C_6$-$C_{30}$ aryl, a $C_3$-$C_{30}$ heteroaryl, a substituted $C_6$-$C_{30}$ aryl, and a substituted $C_3$-$C_{30}$ heteroaryl;

n is an integer from 0 to 3;

$R_1$ to $R_8$ are each independently selected from one of a hydrogen, a deuteron, a halogen, a $C_1$-$C_{30}$ alkyl, a $C_1$-$C_{30}$ alkyl substituted with a heteroatom, a $C_6$-$C_{30}$ aryl, and a $C_3$-$C_{30}$ heteroaryl.

In one embodiment, the nitrogen-containing heterocyclic organic compound has a chemical structure represented by the following formula (II):

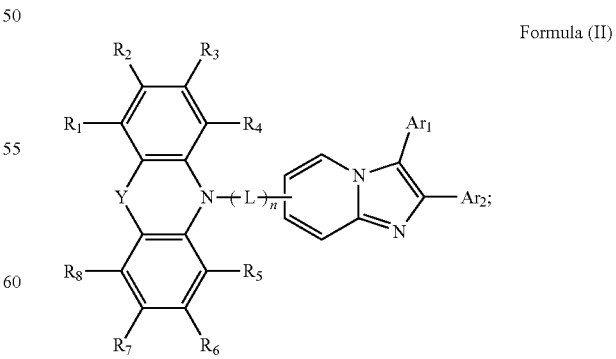

Formula (II)

and

Y is a single bond, O, S, an imino, a methylene, a methylidenesilane group, a substituted imino, a substituted methylene, or a substituted methylidenesilane group, the substituents in the substituted imino, the substituted methylene, and the substituted methylidenesilane group are each independently selected from one of a hydrogen, a deuteron, a $C_1$-$C_{30}$ alkyl, a $C_1$-$C_{30}$ alkyl substituted with a heteroatom, a $C_6$-$C_{30}$ aryl, and a $C_3$-$C_{30}$ heteroaryl;

L, $Ar_1$, and $Ar_2$ are each independently selected from one of a $C_6$-$C_{30}$ aryl, a $C_3$-$C_{30}$ heteroaryl, a substituted $C_6$-$C_{30}$ aryl, and a substituted $C_3$-$C_{30}$ heteroaryl;

n is an integer from 0 to 3;

$R_1$ to $R_8$ are each independently selected from one of a hydrogen, a deuteron, a halogen, a $C_1$-$C_{30}$ alkyl, a $C_1$-$C_{30}$ alkyl substituted with a heteroatom, a $C_6$-$C_{30}$ aryl, and a $C_3$-$C_{30}$ heteroaryl.

In one embodiment, the nitrogen-containing heterocyclic organic compound has a chemical structure represented by the following formula (III):

Formula (III)

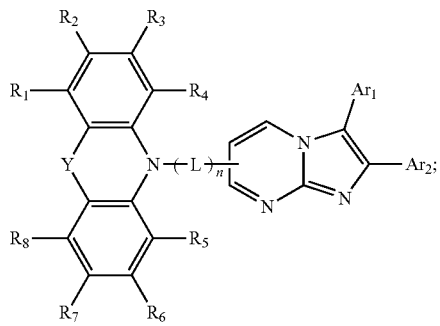

and

Y is a single bond, O, S, an imino, a methylene, a methylidenesilane group, a substituted imino, a substituted methylene, or a substituted methylidenesilane group, the substituents in the substituted imino, the substituted methylene, and the substituted methylidenesilane group are each independently selected from one of a hydrogen, a deuteron, a $C_1$-$C_{30}$ alkyl, a $C_1$-$C_{30}$ alkyl substituted with a heteroatom, a $C_6$-$C_{30}$ aryl, and a $C_3$-$C_{30}$ heteroaryl;

L, $Ar_1$, and $Ar_2$ are each independently selected from one of a $C_6$-$C_{30}$ aryl, a $C_3$-$C_{30}$ heteroaryl, a substituted $C_6$-$C_{30}$ aryl, and a substituted $C_3$-$C_{30}$ heteroaryl;

n is an integer from 0 to 3;

$R_1$ to $R_8$ are each independently selected from one of a hydrogen, a deuteron, a halogen, a $C_1$-$C_{30}$ alkyl, a $C_1$-$C_{30}$ alkyl substituted with a heteroatom, a $C_6$-$C_{30}$ aryl, and a $C_3$-$C_{30}$ heteroaryl.

In one embodiment, the $C_6$-$C_{30}$ aryl is phenyl, naphthyl, or biphenyl.

In one embodiment, the $C_3$-$C_{30}$ heteroaryl is pyridyl, pyrimidinyl, imidazolyl, oxazolyl, triazinyl, carbazolyl, or diphenylamino.

In one embodiment, the nitrogen-containing heterocyclic organic compound is selected from one of Compounds 1 to 156, and each structural formula of Compounds 1 to 156 is as follows:

Compound 1

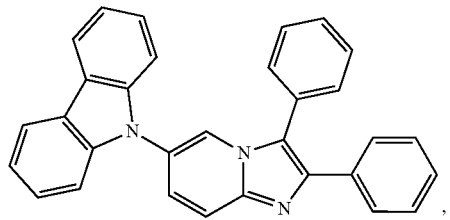

Compound 2

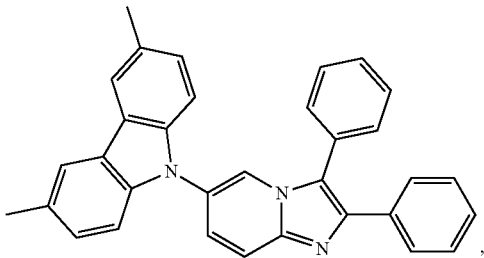

Compound 3

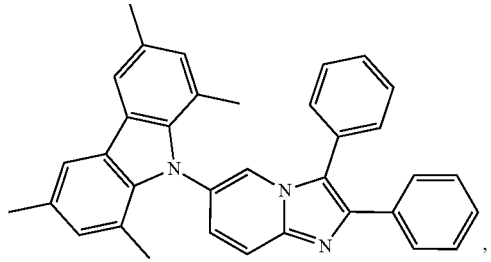

Compound 4

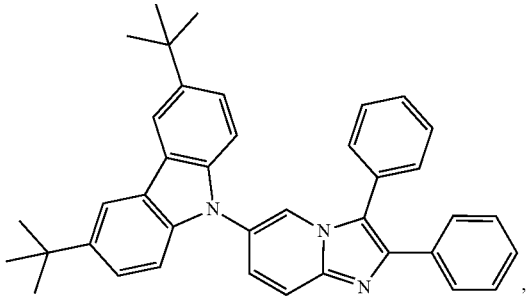

-continued
Compound 5
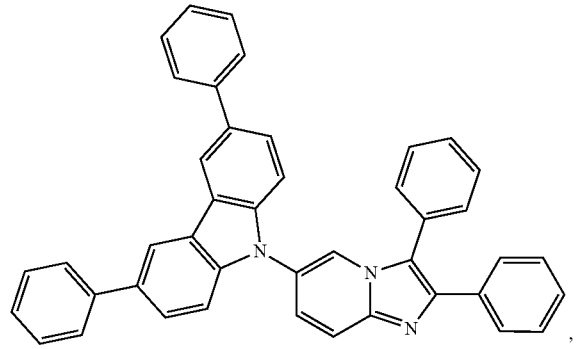
Compound 6
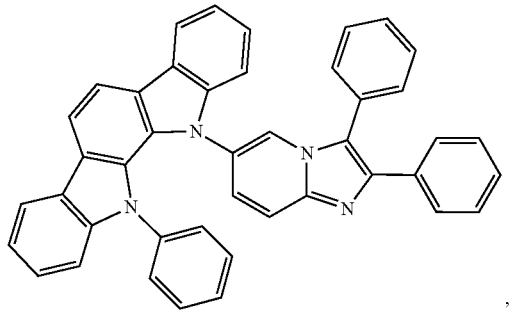
Compound 7
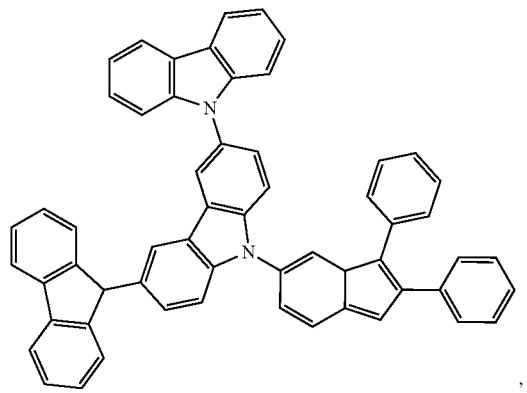
Compound 8
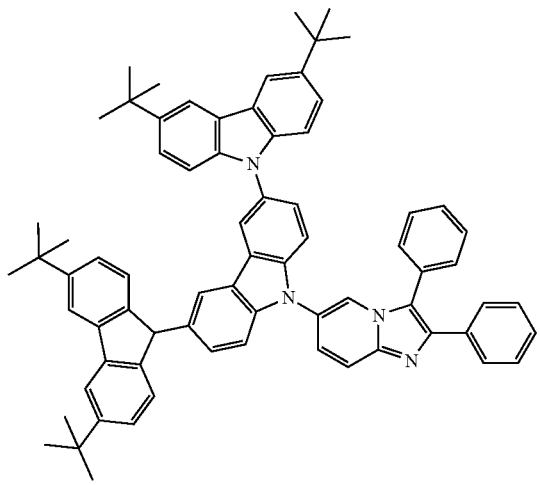
Compound 9
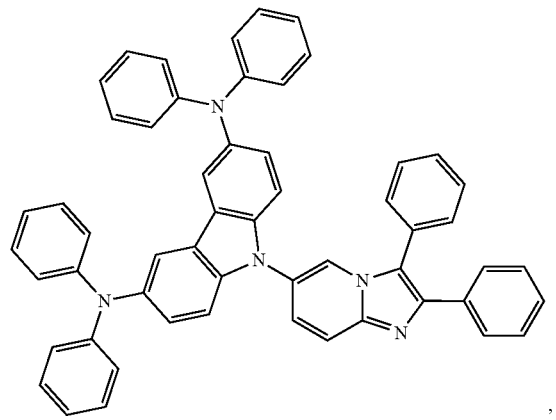
Compound 10
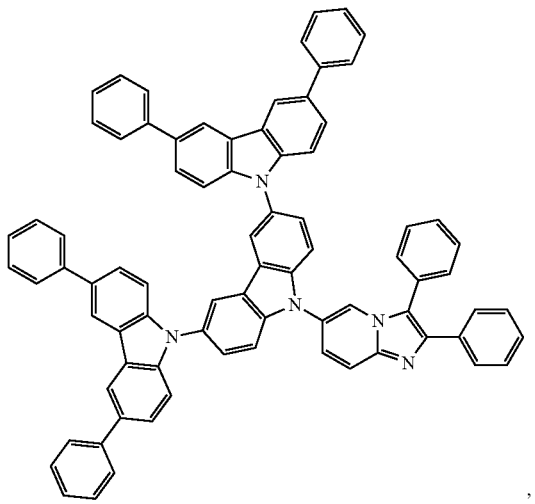

-continued
Compound 11
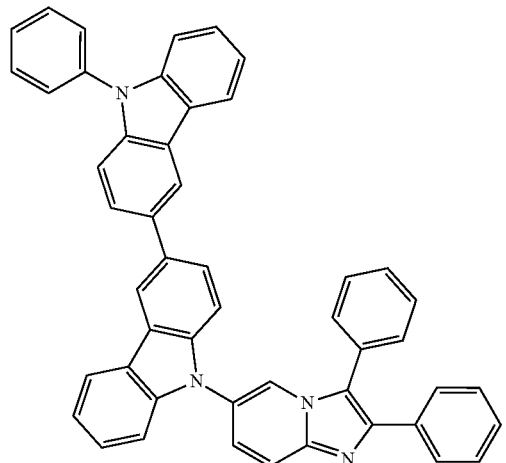
Compound 12
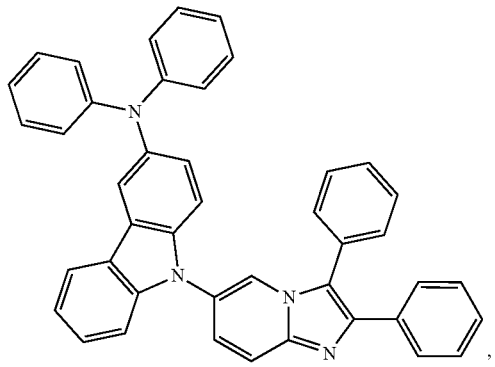
Compound 13
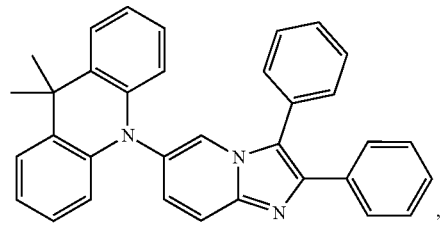
Compound 14
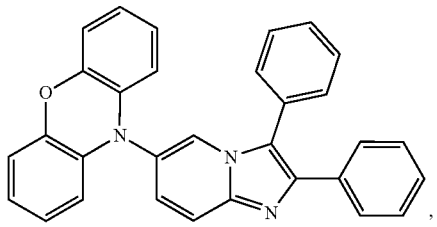
Compound 15
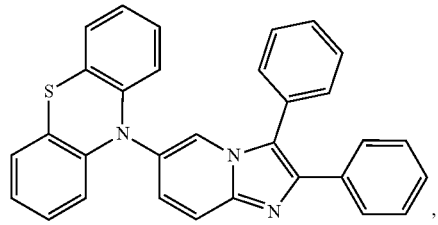
Compound 16
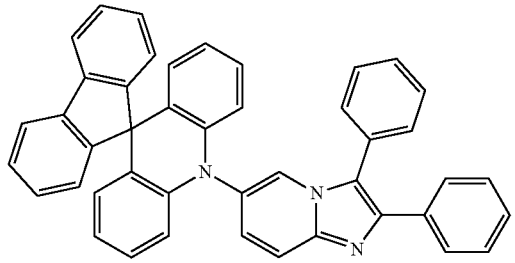
Compound 17
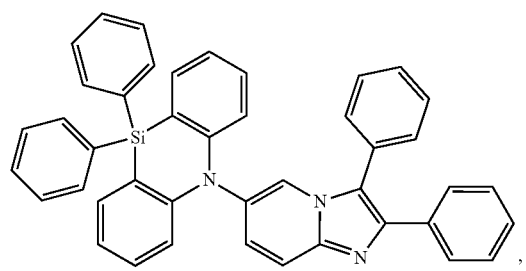
Compound 18
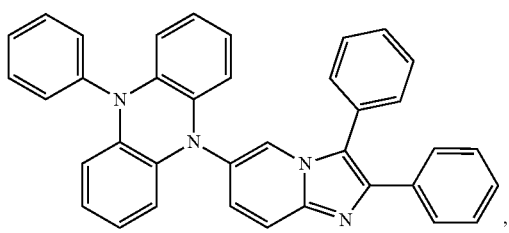
Compound 19
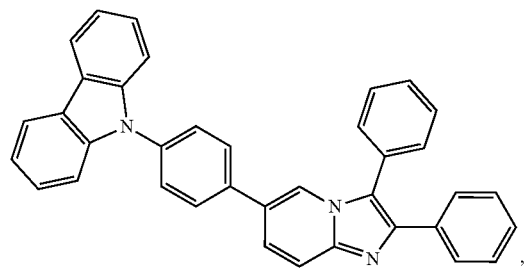
Compound 20
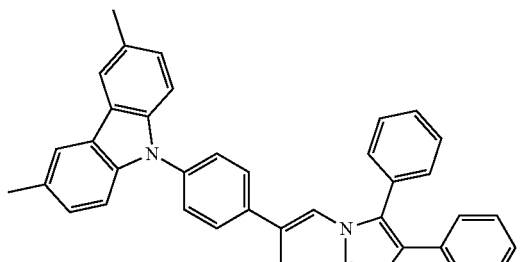

-continued
Compound 21
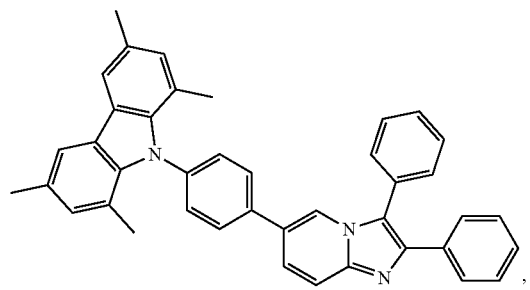
Compound 22
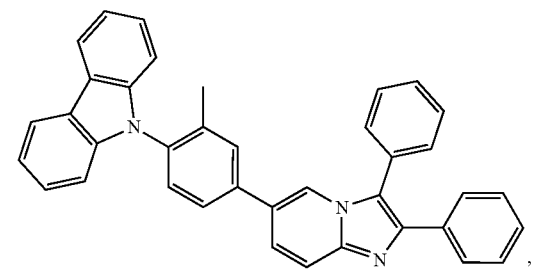
Compound 23
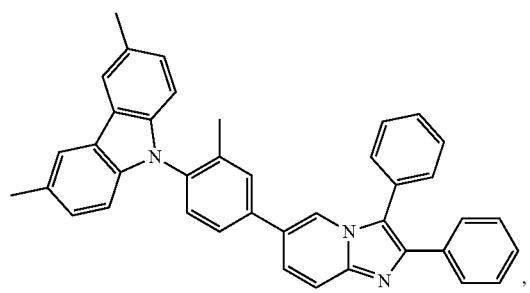
Compound 24
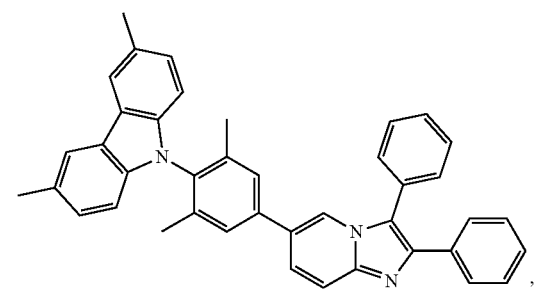
Compound 25
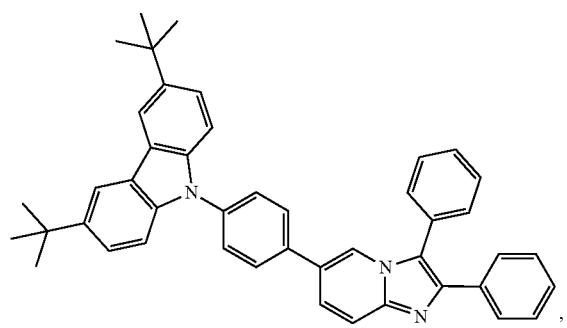
Compound 26
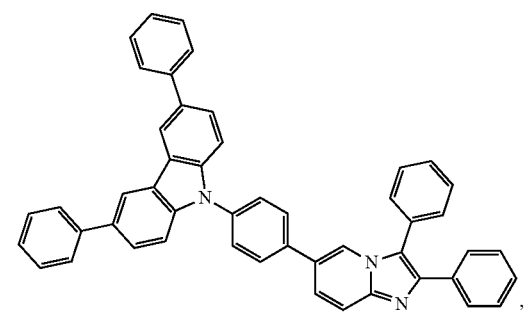
Compound 27
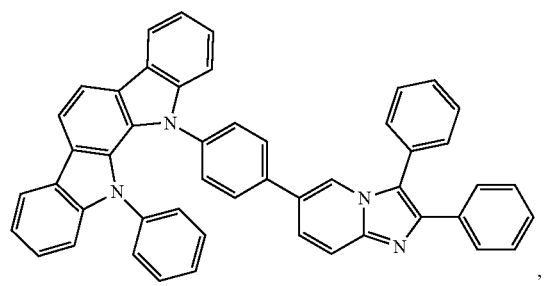
Compound 28
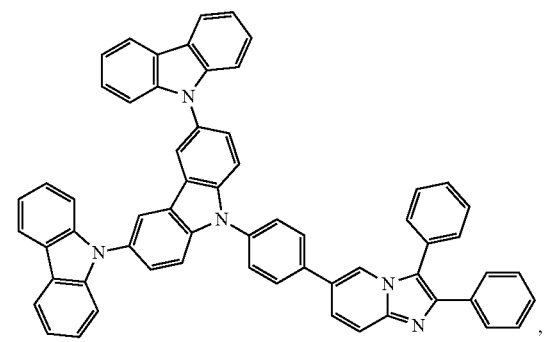

-continued
Compound 29
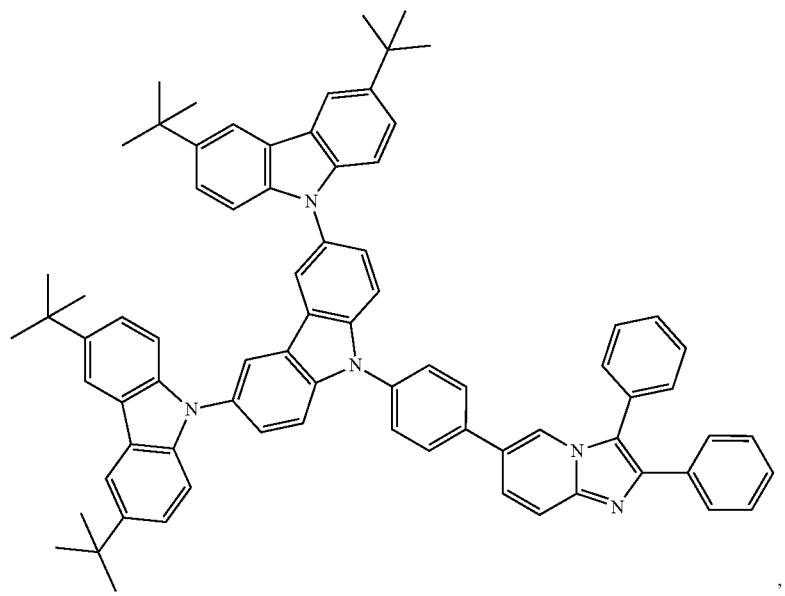
Compound 30
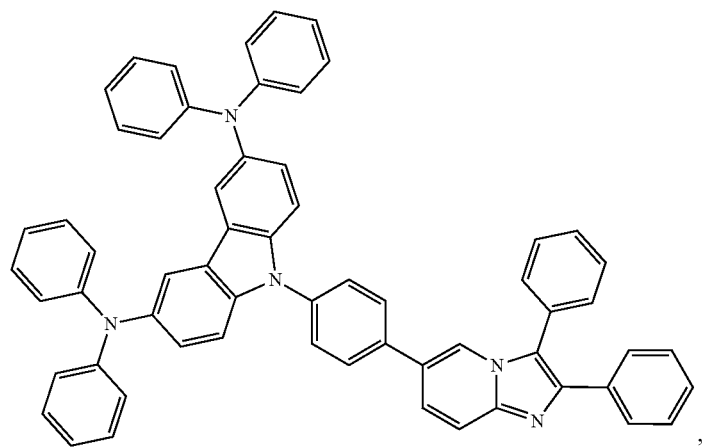

-continued
Compound 31
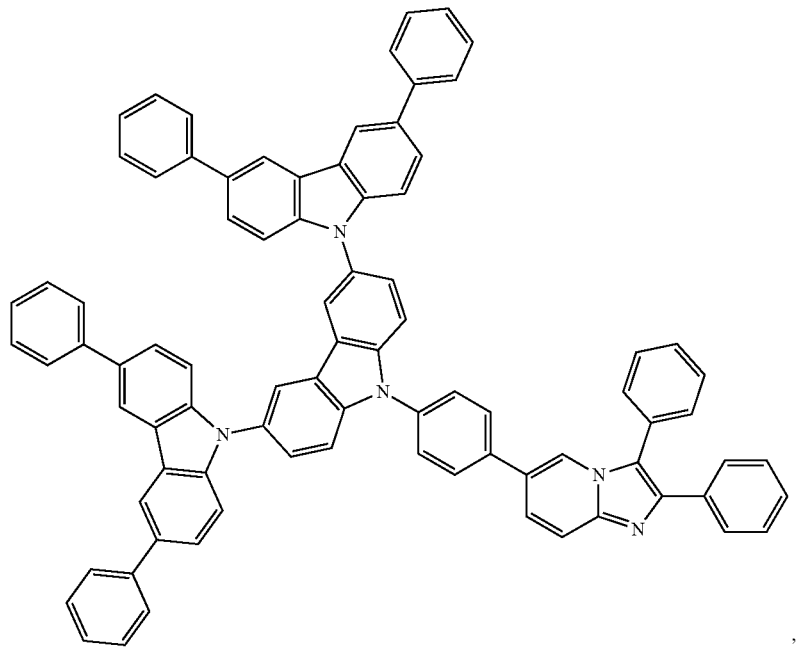
Compound 32
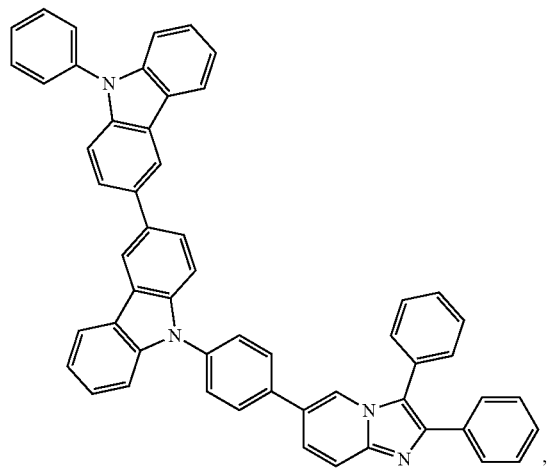
Compound 33
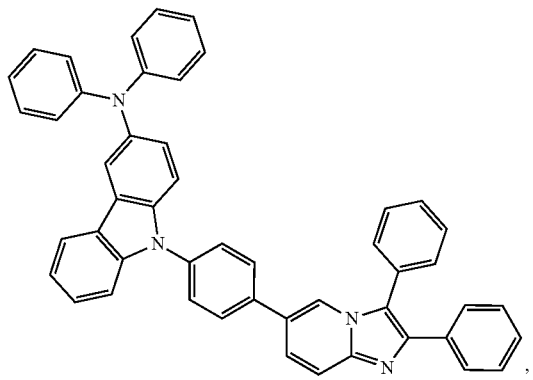
Compound 34
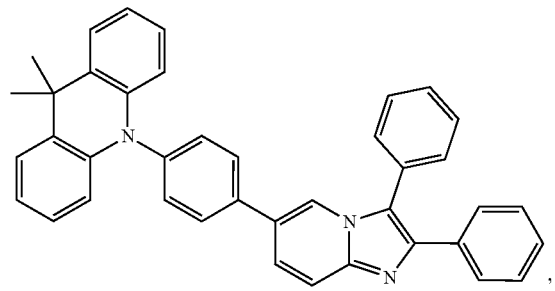
Compound 35
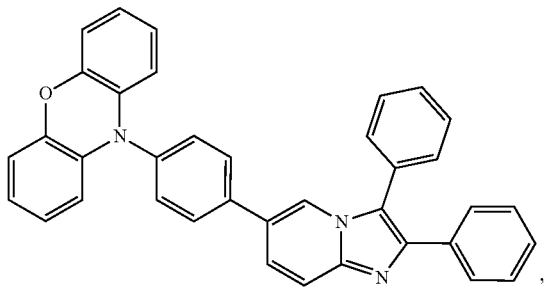

-continued
Compound 36
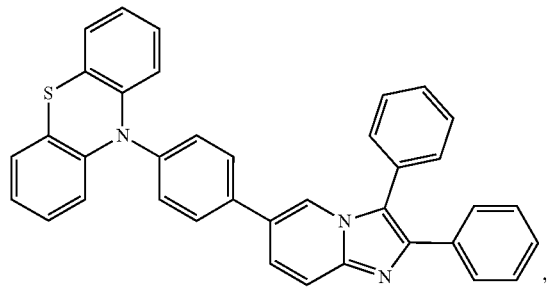
Compound 37
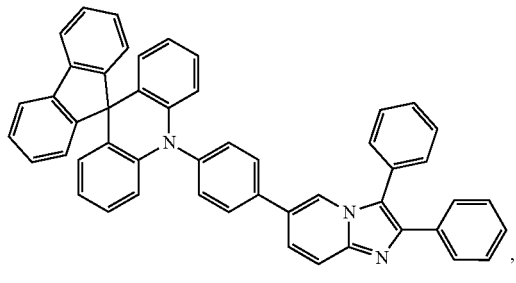
Compound 38
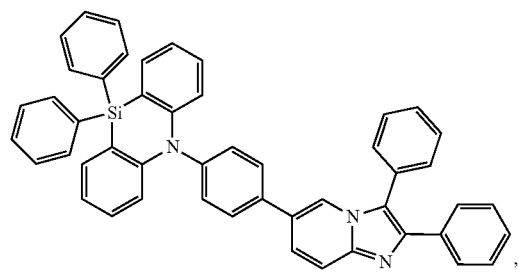
Compound 39
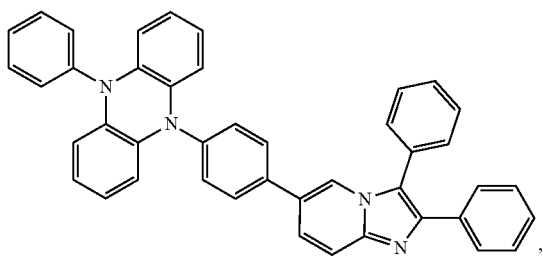
Compound 40
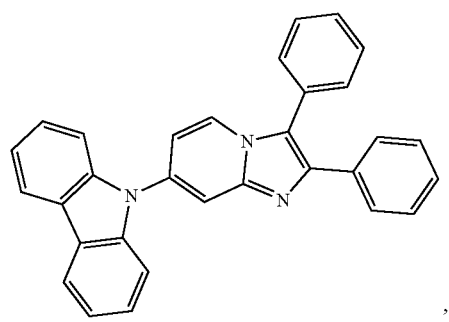
Compound 41
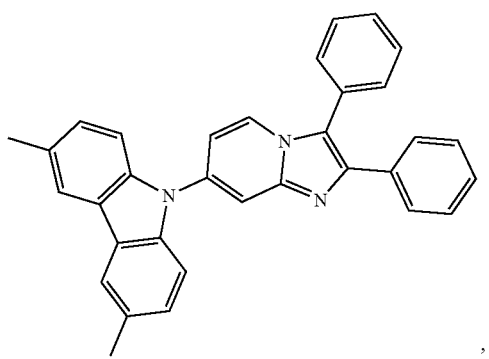
Compound 42
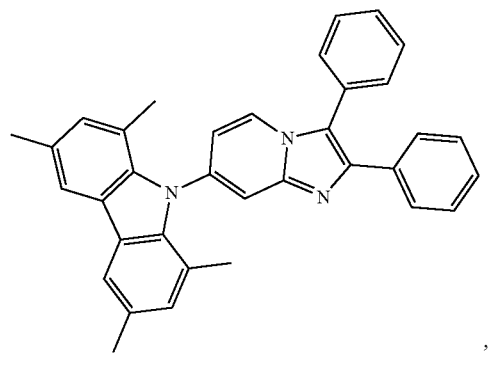
Compound 43
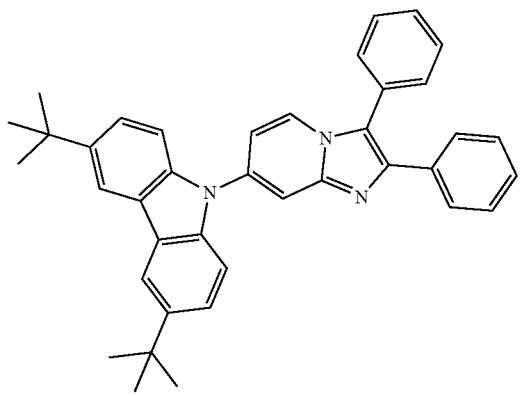

-continued
Compound 44
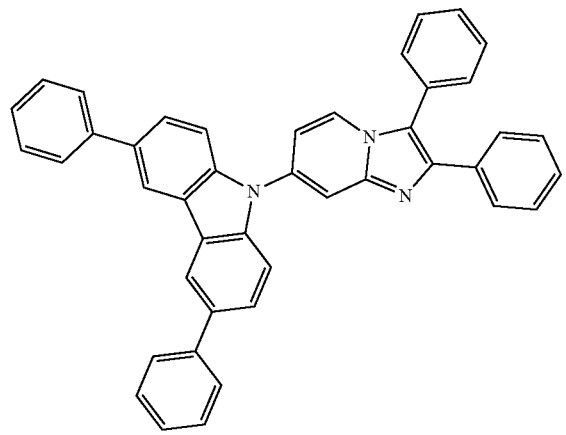
Compound 45
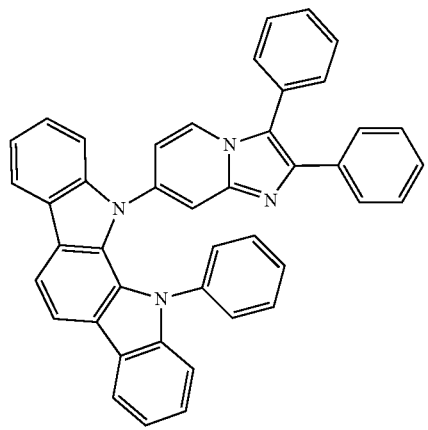
Compound 46
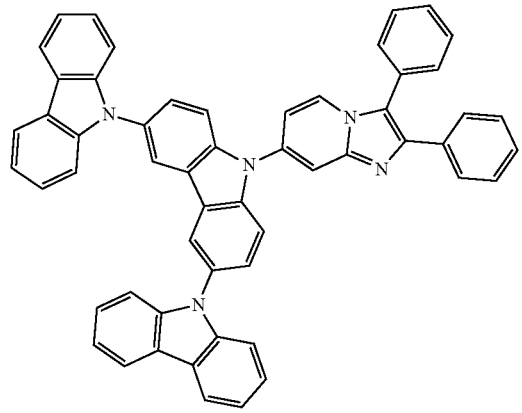
Compound 47
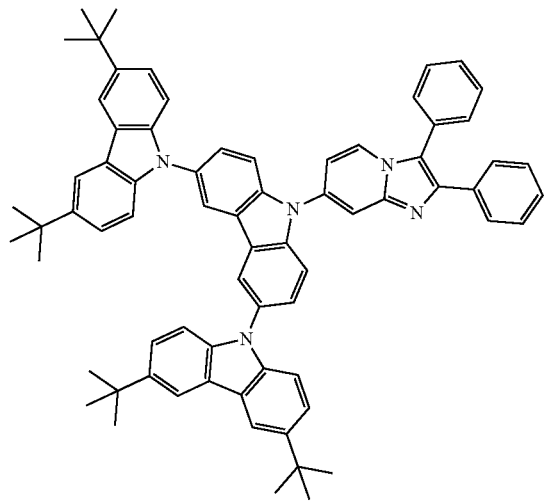
Compound 48
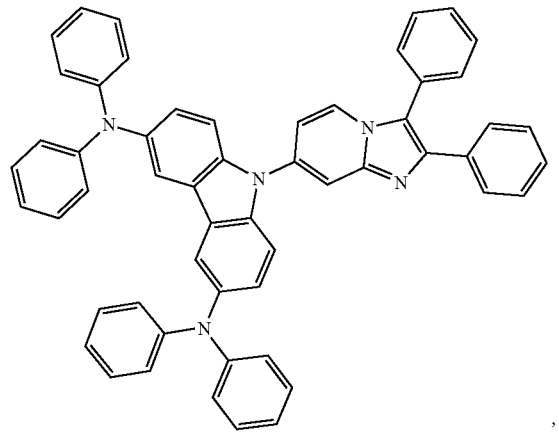
Compound 49
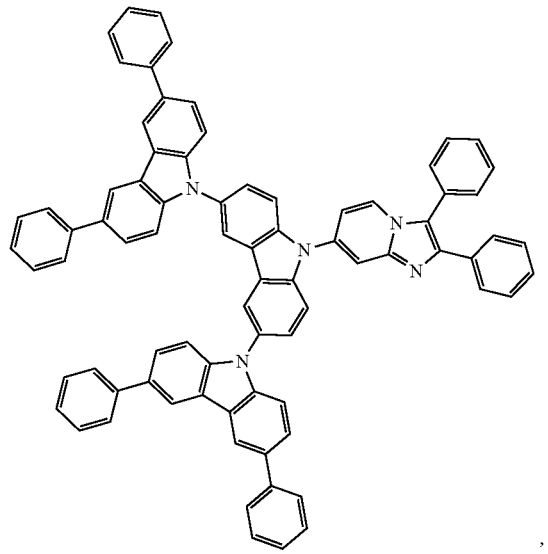

-continued
Compound 50
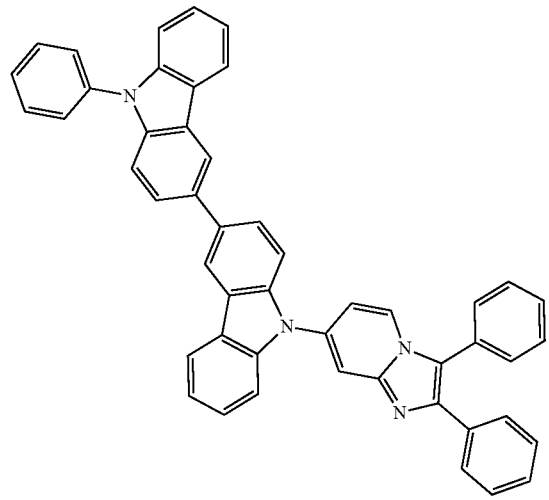
Compound 51
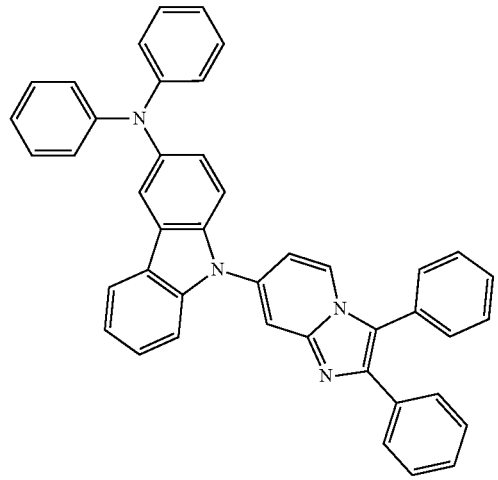
Compound 52
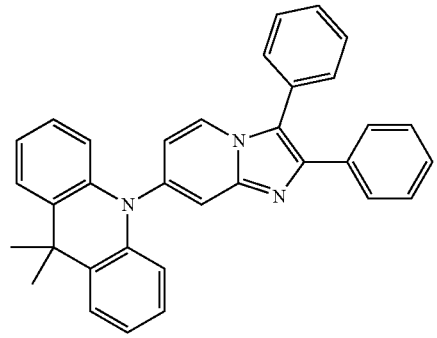
Compound 53
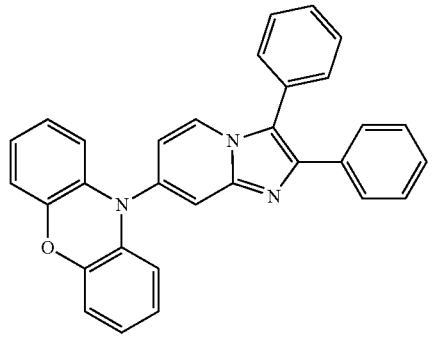
Compound 54
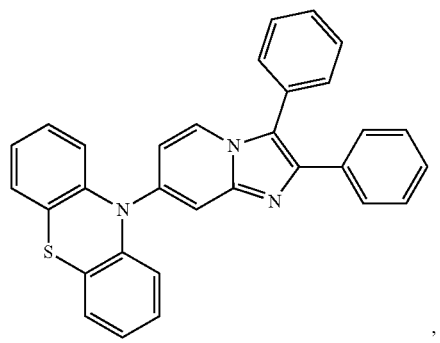
Compound 55
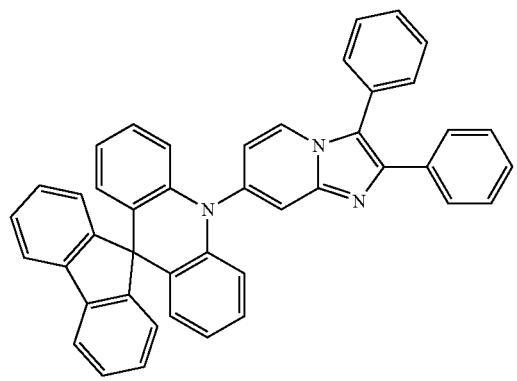
Compound 56
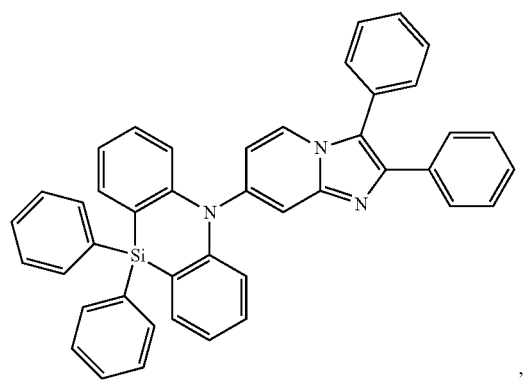
Compound 57
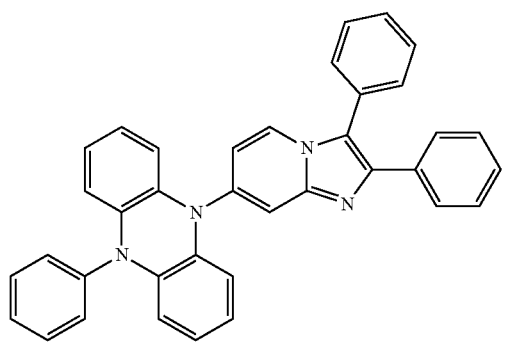

-continued
Compound 58
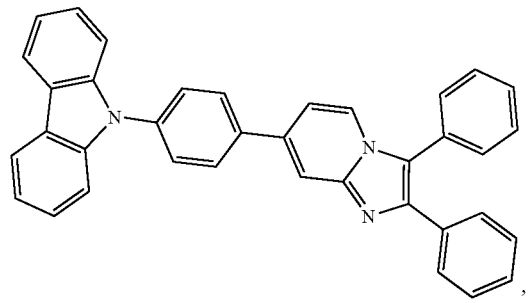
Compound 59
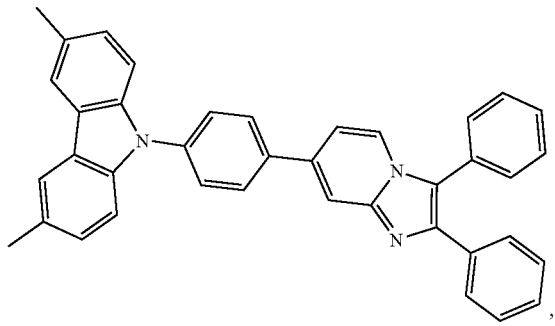
Compound 60
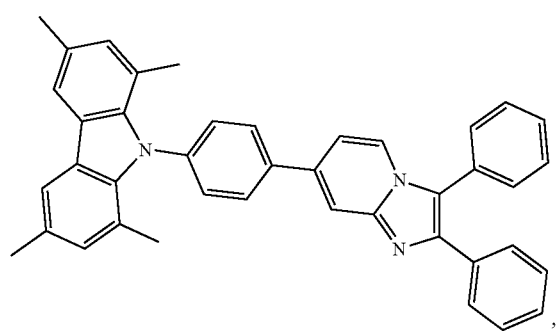
Compound 61
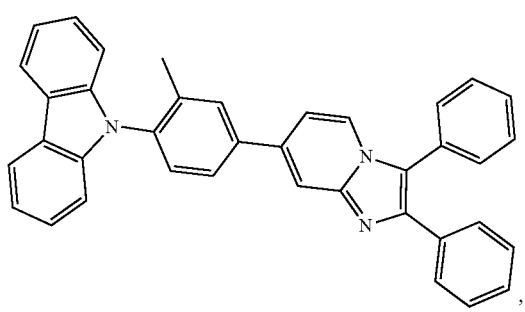
Compound 62
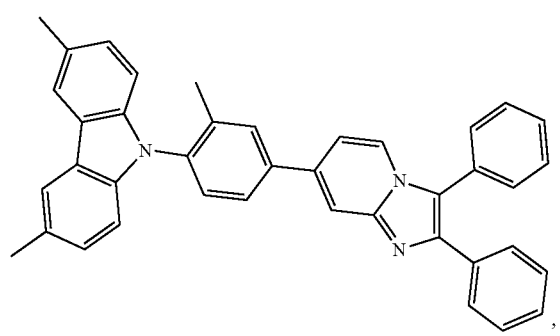
Compound 63
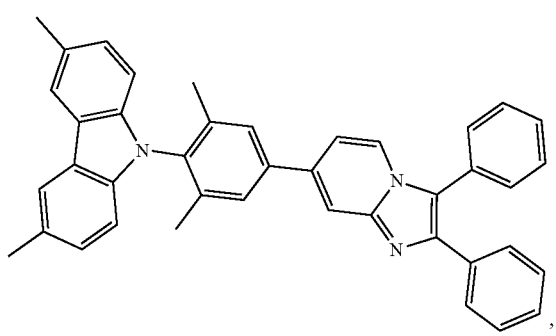
Compound 64
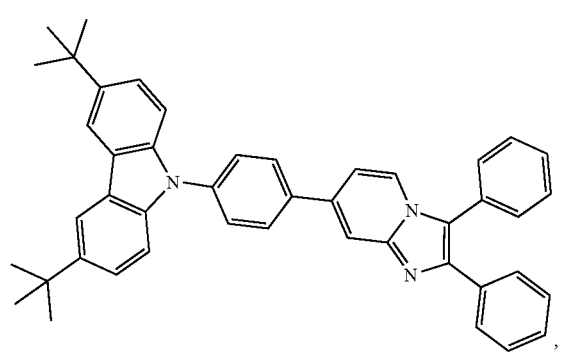
Compound 65
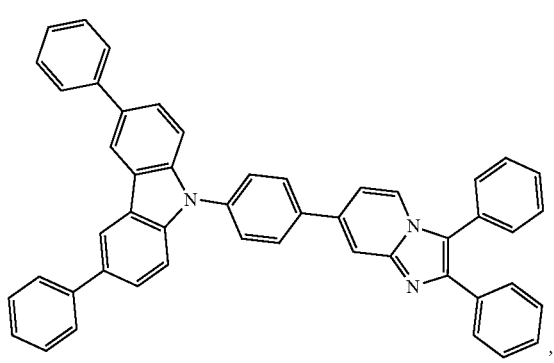

-continued
Compound 66
Compound 67
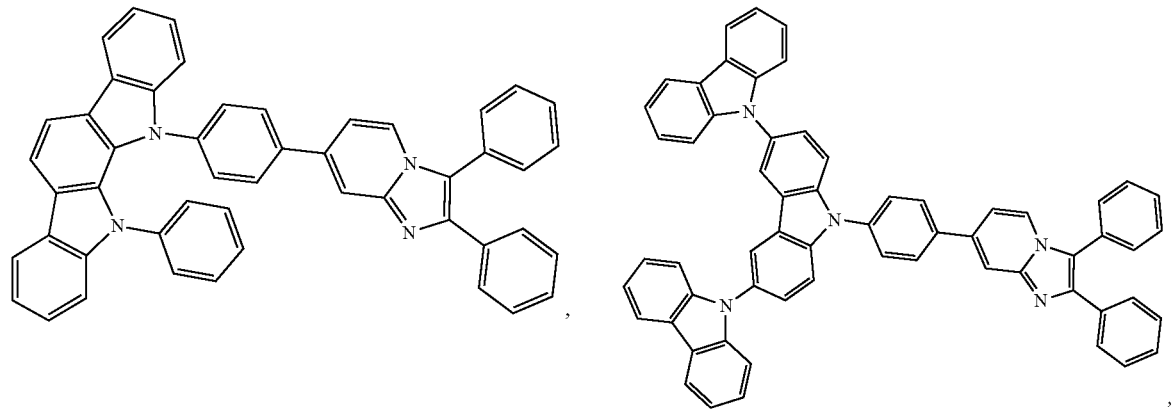
Compound 68
Compound 69
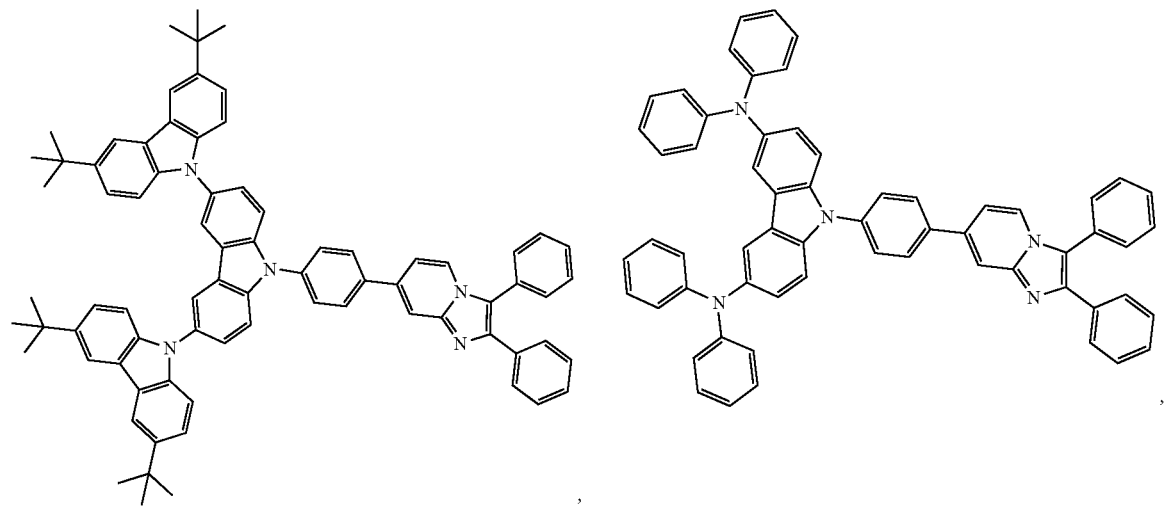
Compound 70
Compound 71
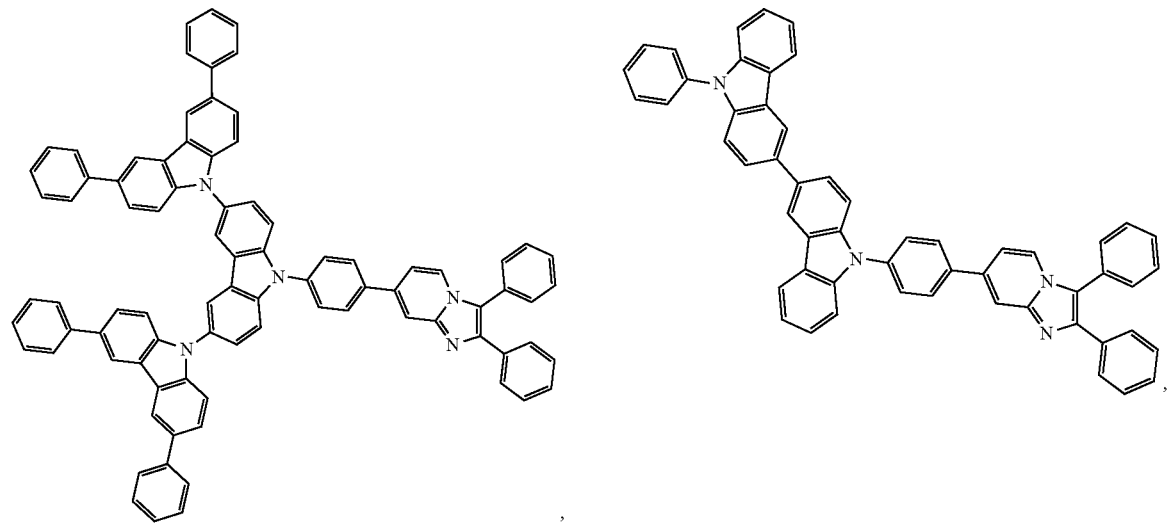

-continued
Compound 72
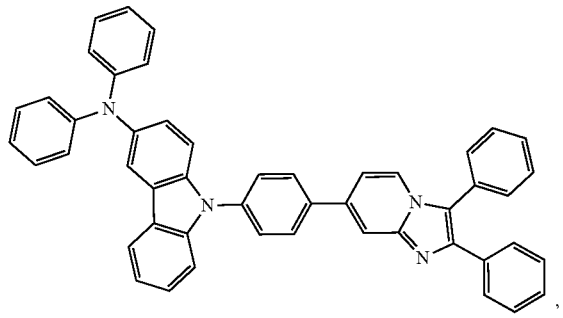
Compound 73
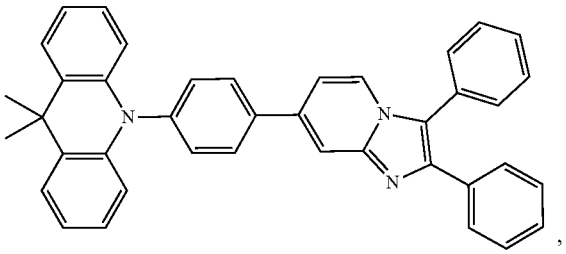
Compound 74
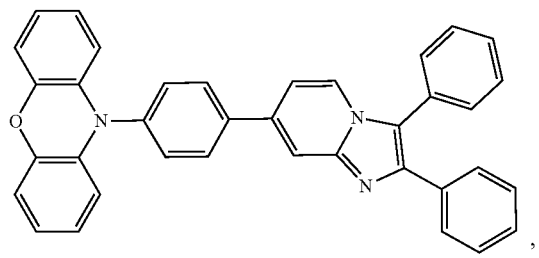
Compound 75
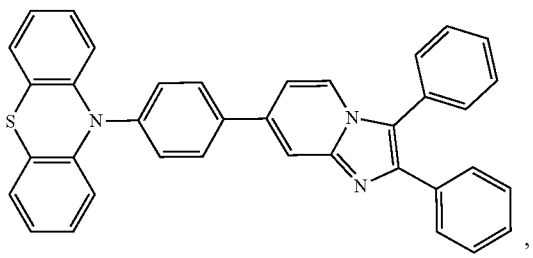
Compound 76
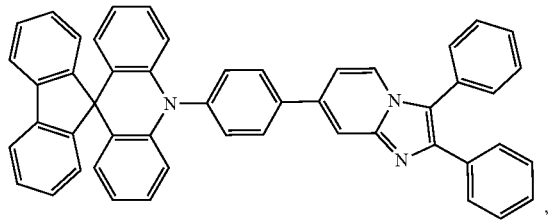
Compound 77
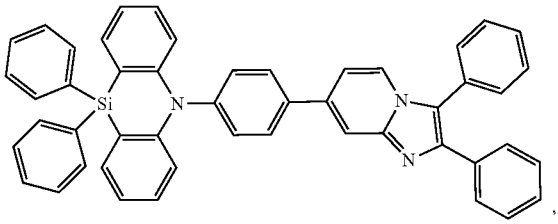
Compound 78
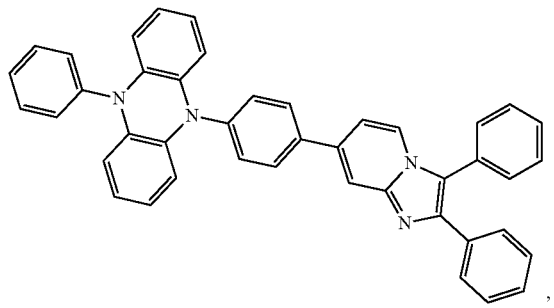
Compound 79
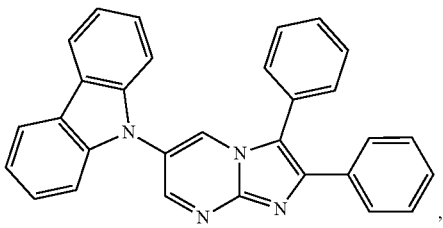
Compound 80
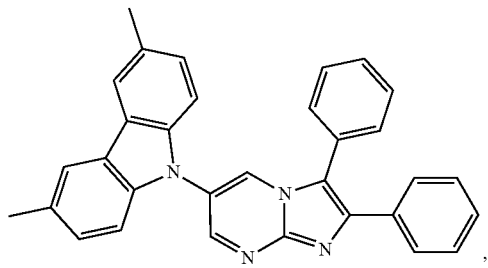
Compound 81
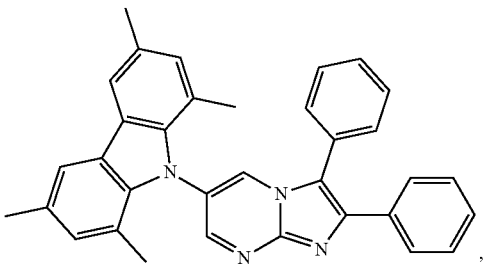

-continued
Compound 82
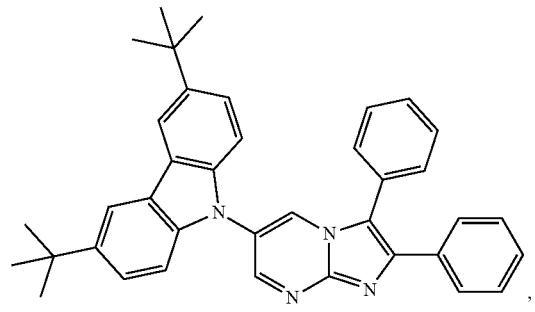
Compound 83
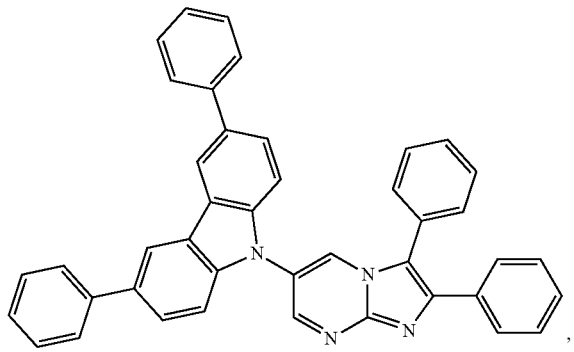
Compound 84
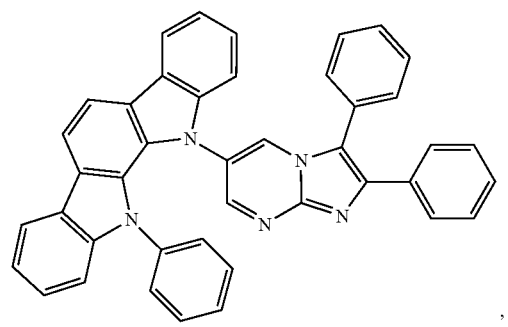
Compound 85
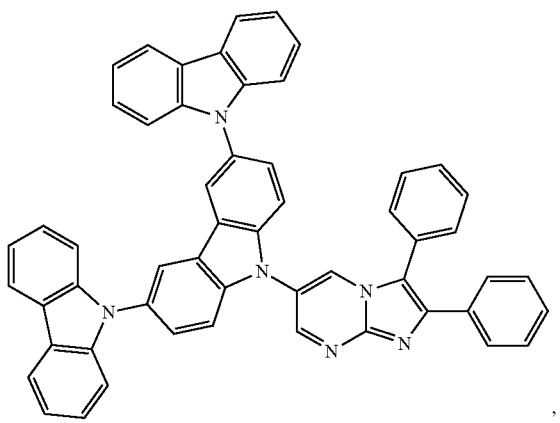
Compound 86
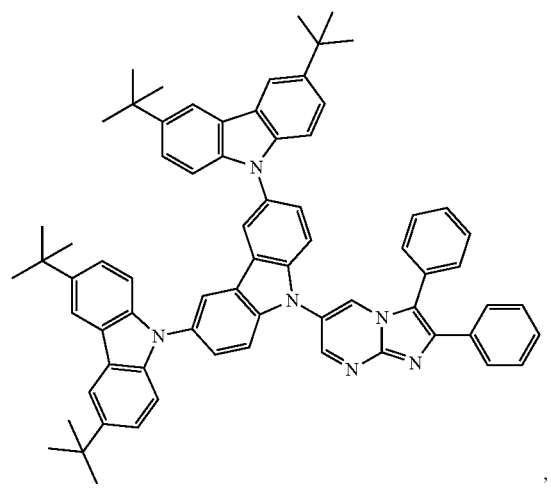
Compound 87
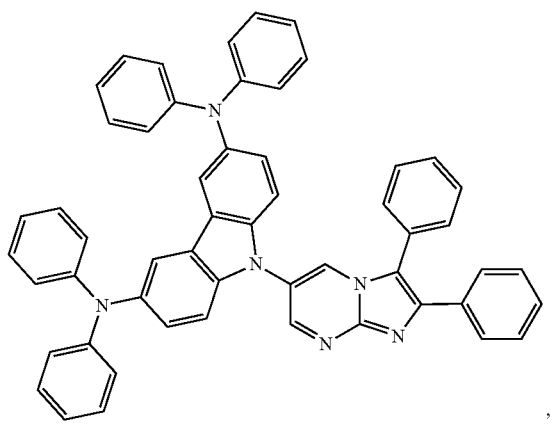

-continued
Compound 88
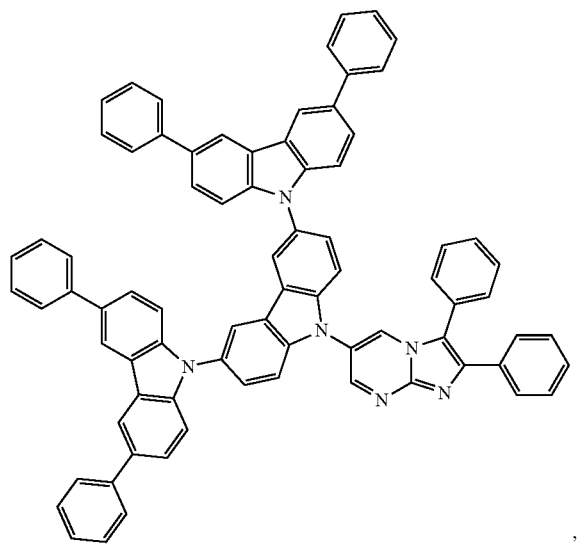
Compound 89
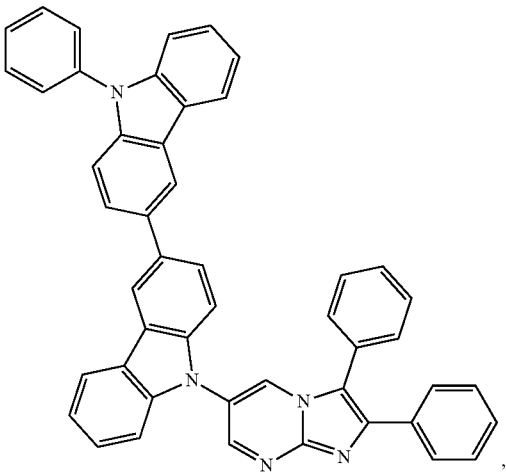
Compound 90
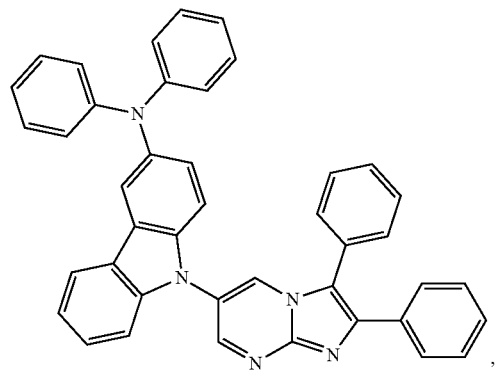
Compound 91
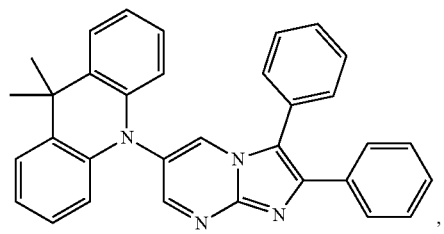
Compound 92
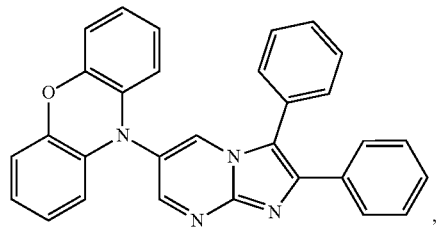
Compound 93
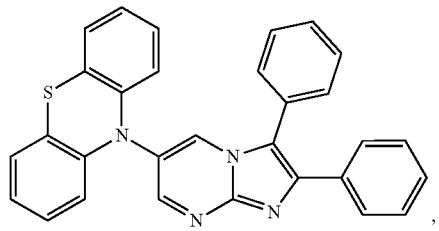
Compound 94
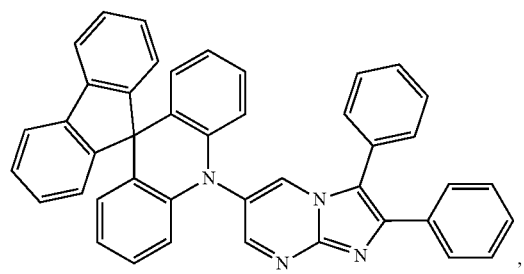
Compound 95
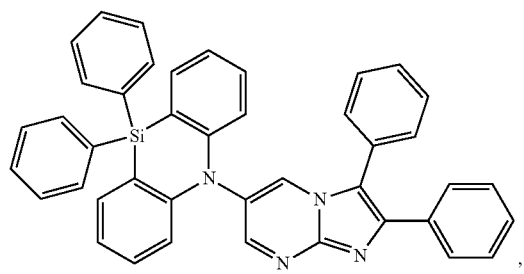

-continued
Compound 96
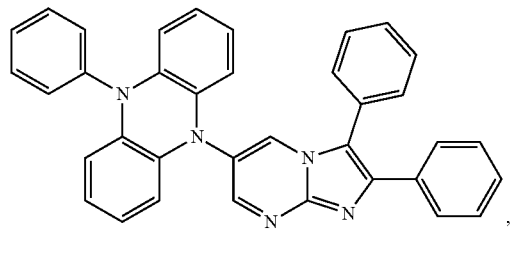
Compound 97
Compound 98
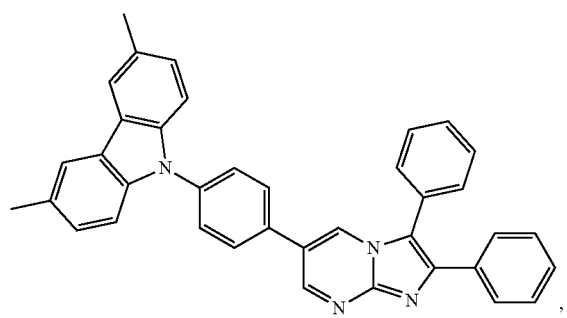
Compound 99
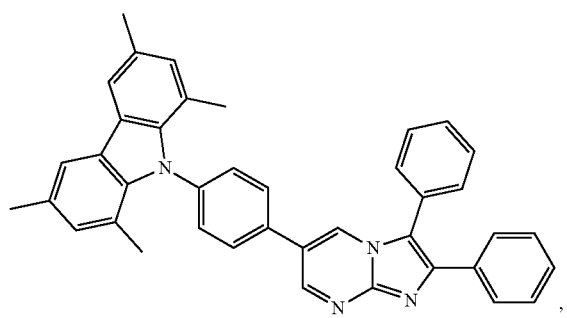
Compound 100
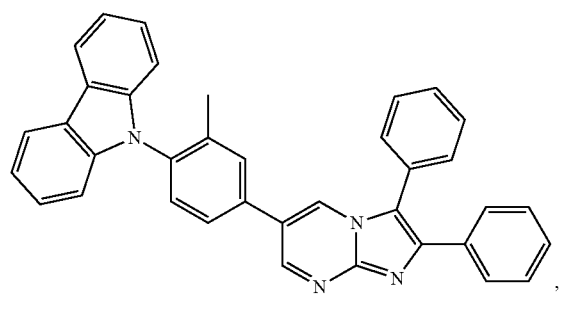
Compound 101
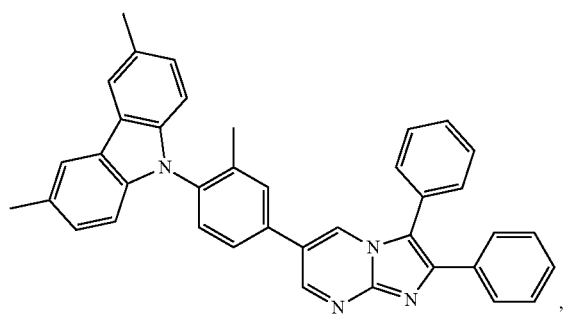
Compound 102
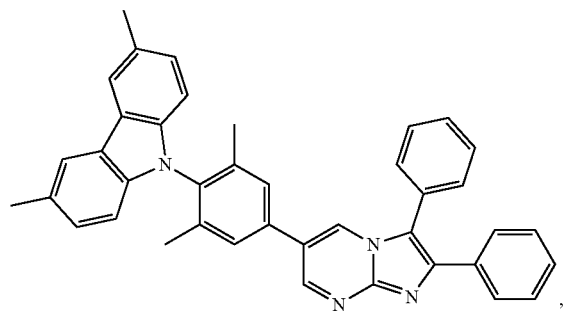
Compound 103
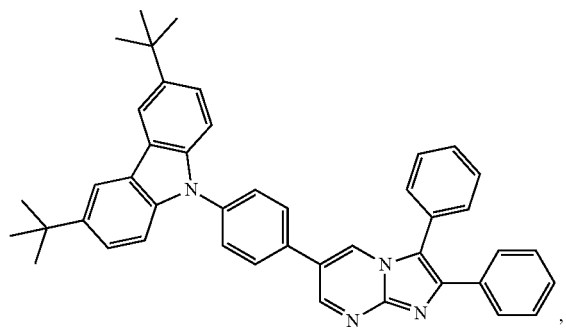

-continued
Compound 104
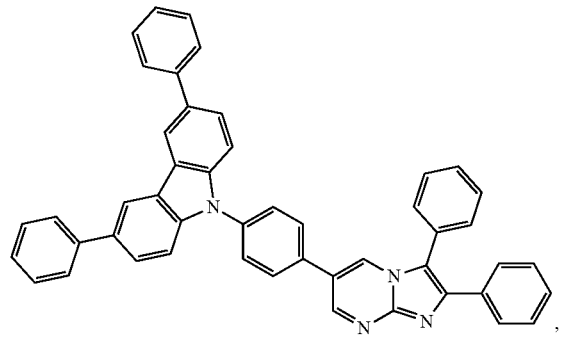
Compound 105
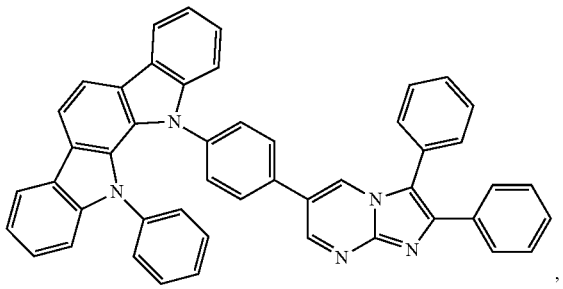
Compound 106
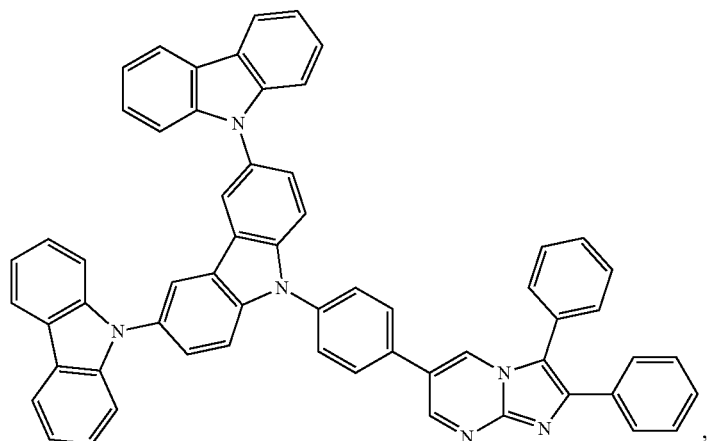
Compound 107
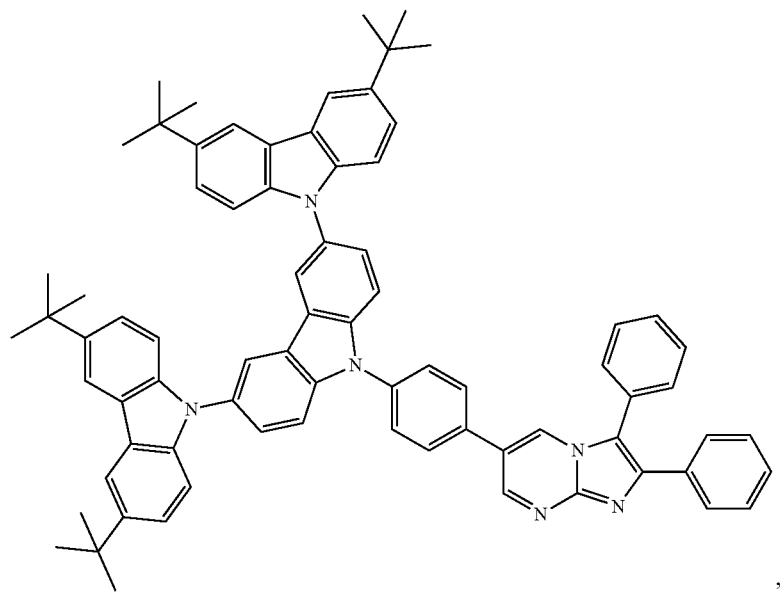

Compound 108
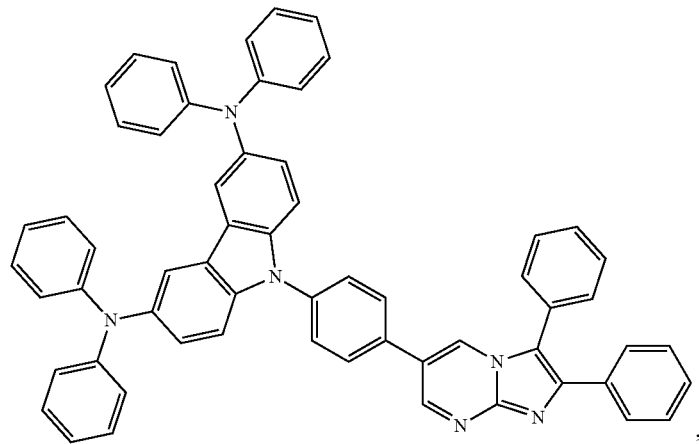
Compound 109
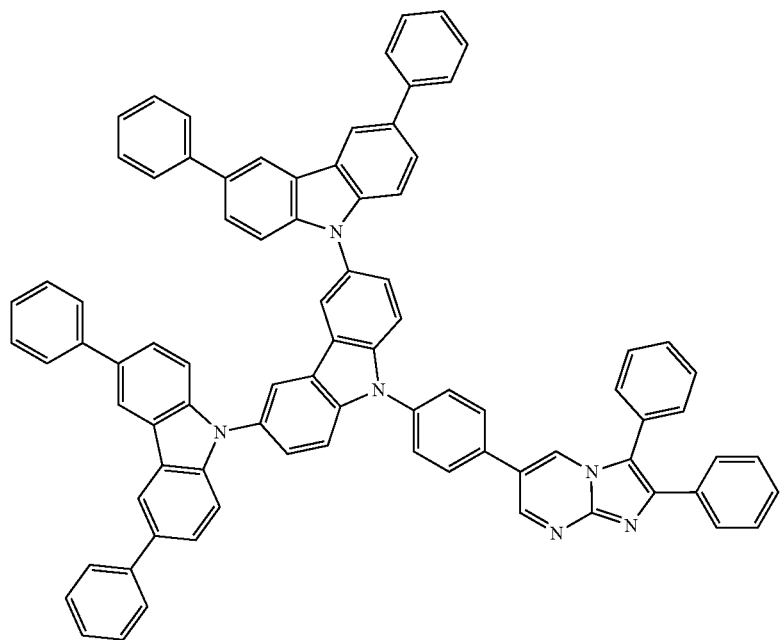
Compound 110
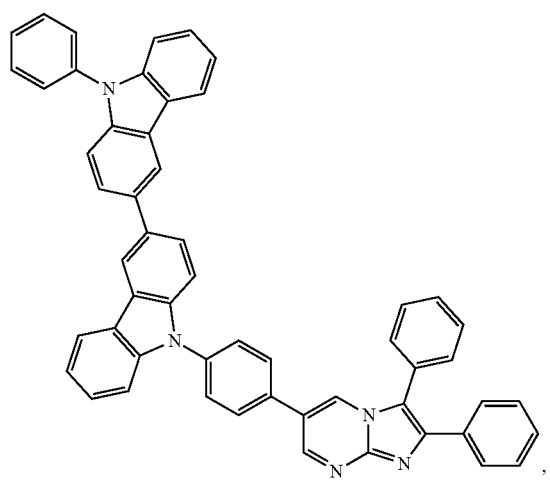
Compound 111
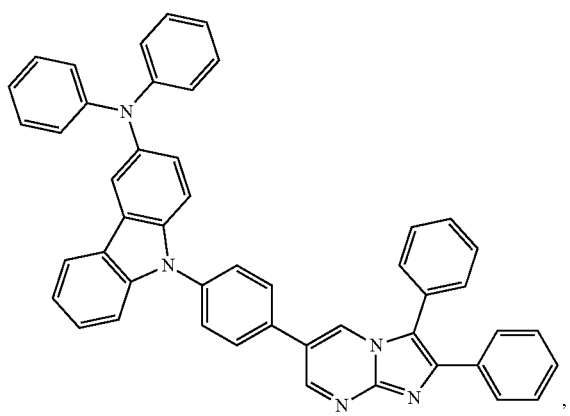

-continued
Compound 112
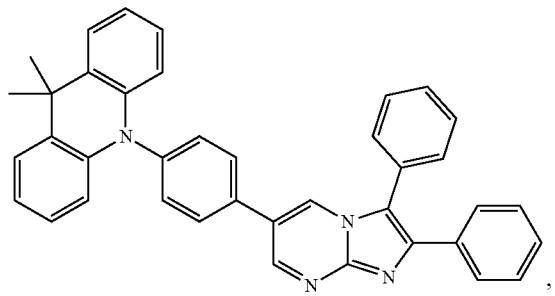
Compound 113
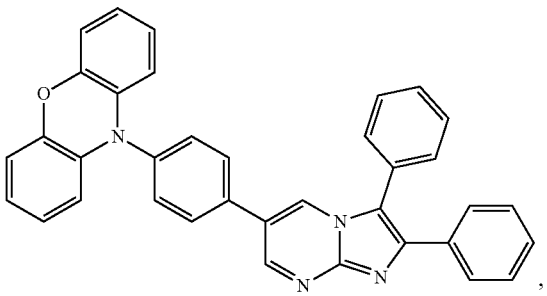
Compound 114
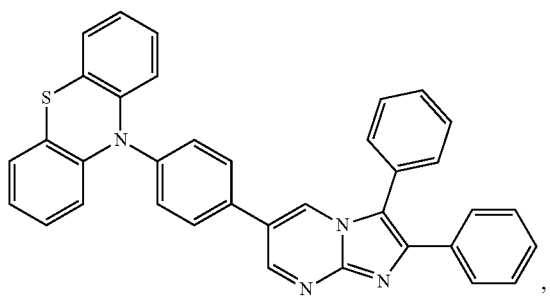
Compound 115
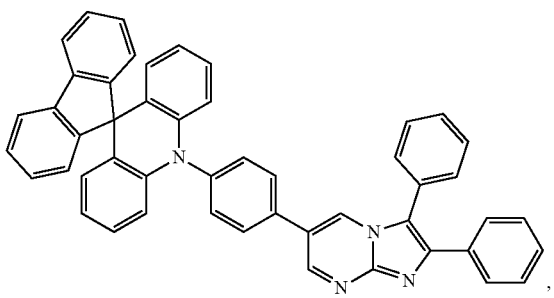
Compound 116
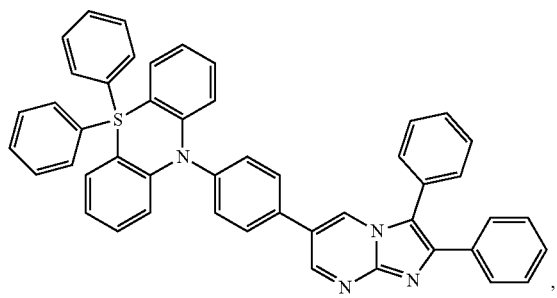
Compound 117
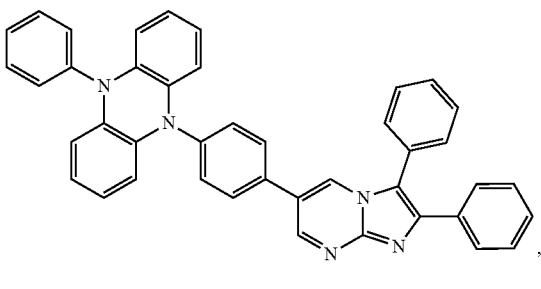
Compound 118
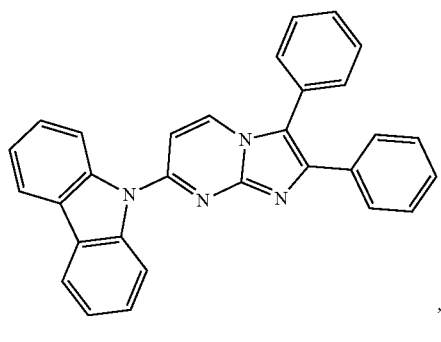
Compound 119
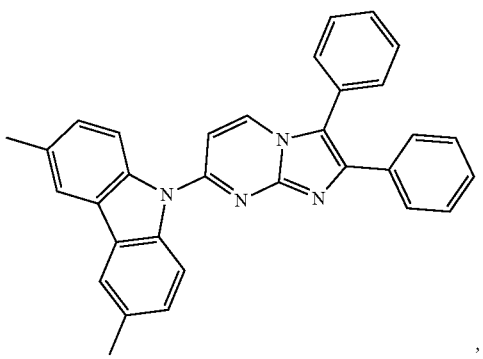

-continued
Compound 120
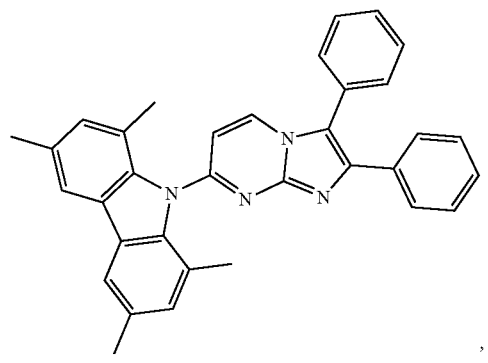
Compound 121
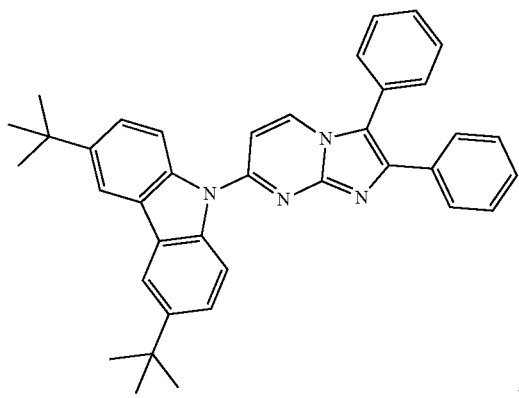
Compound 122
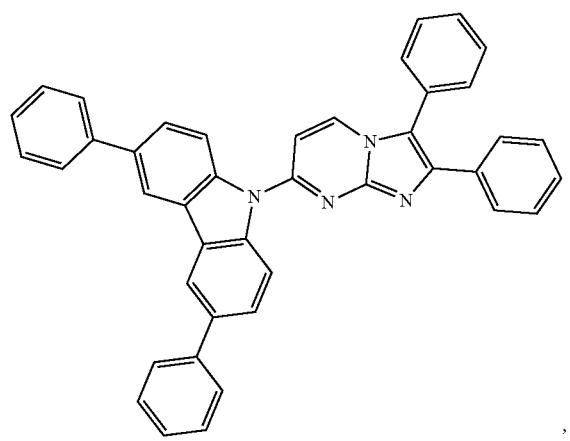
Compound 123
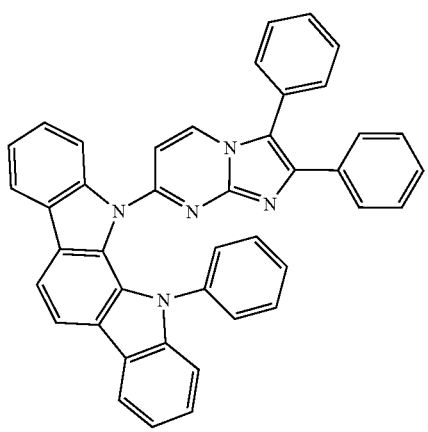
Compound 124
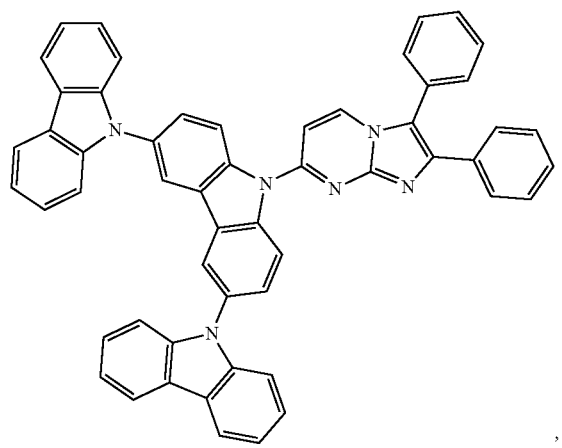
Compound 125
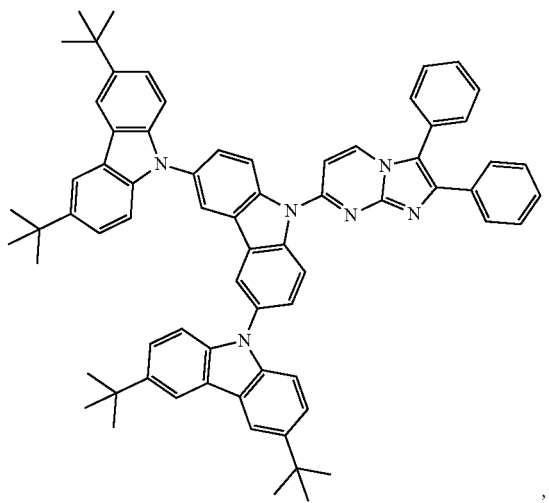

-continued
Compound 126
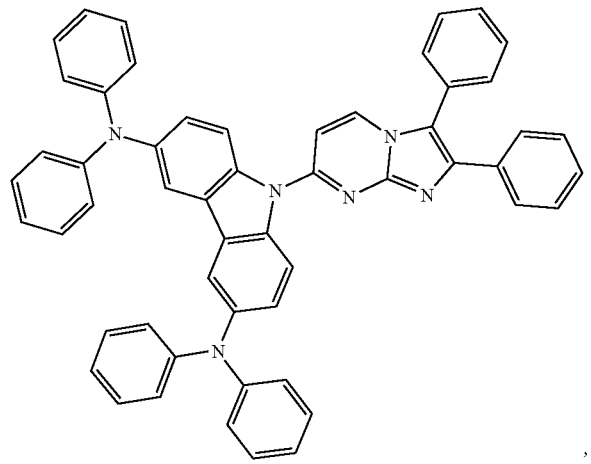
Compound 127
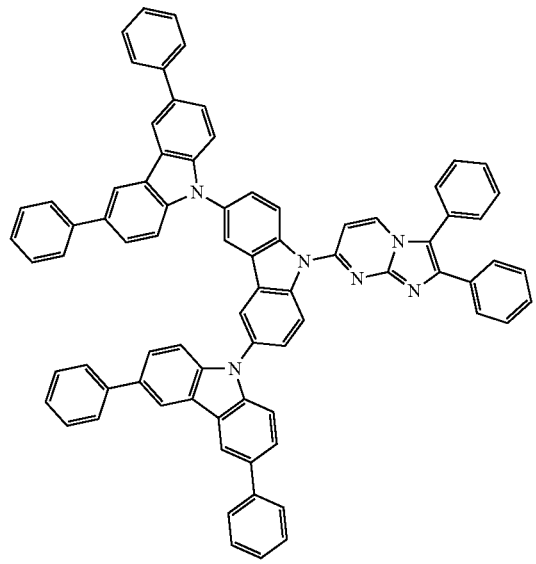
Compound 128
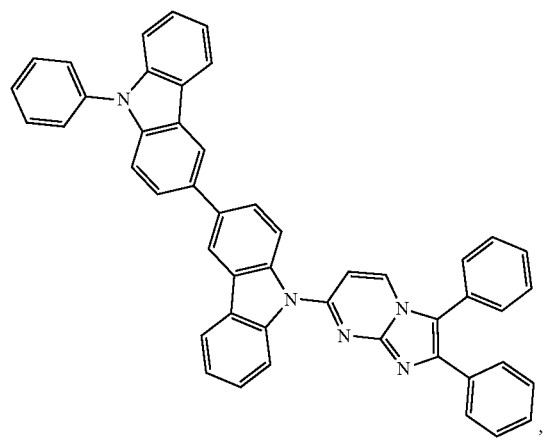
Compound 129
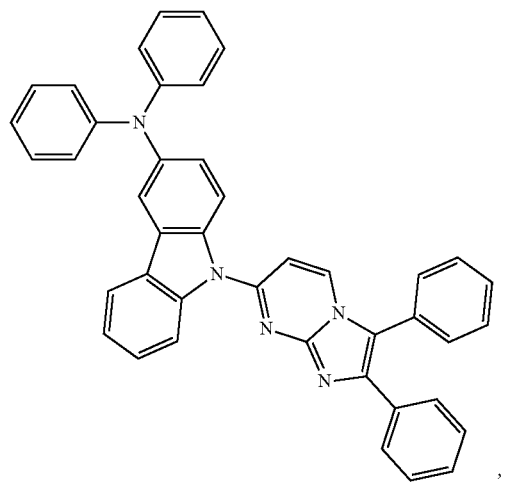
Compound 130
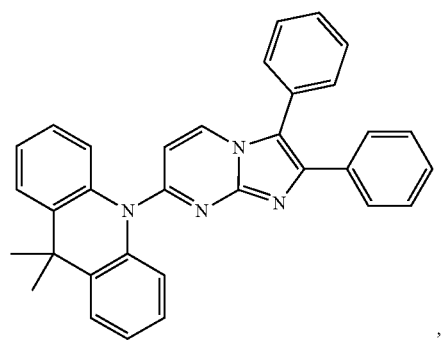
Compound 131
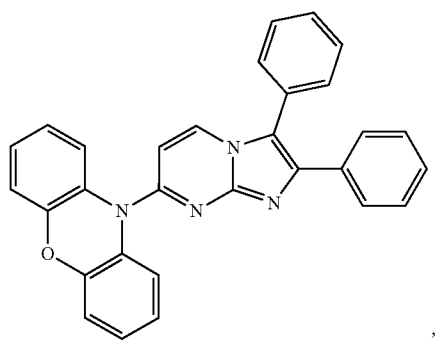

-continued
Compound 132
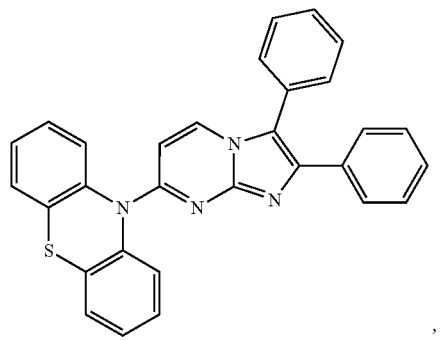
Compound 133
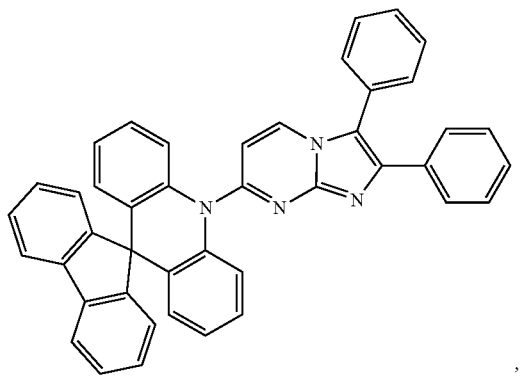
Compound 134
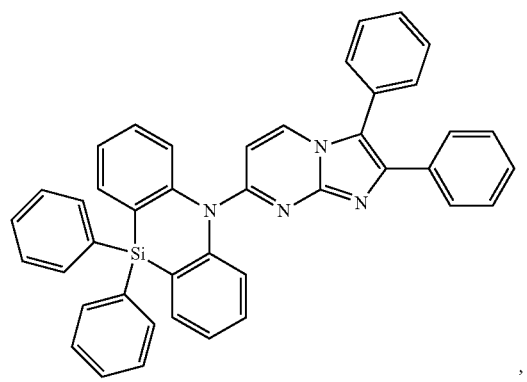
Compound 135
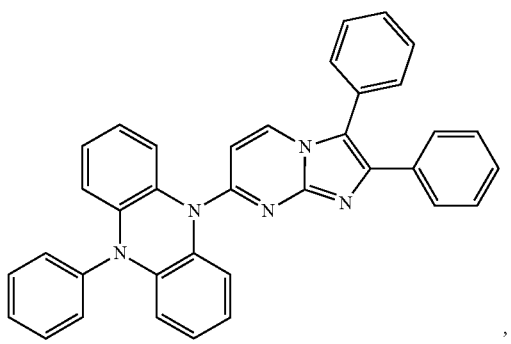
Compound 136
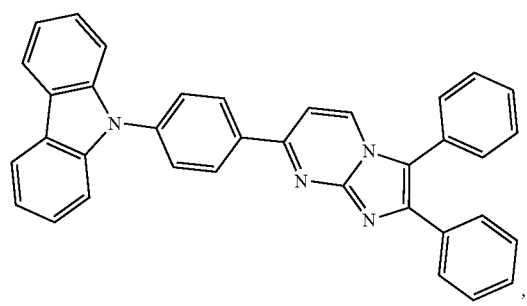
Compound 137
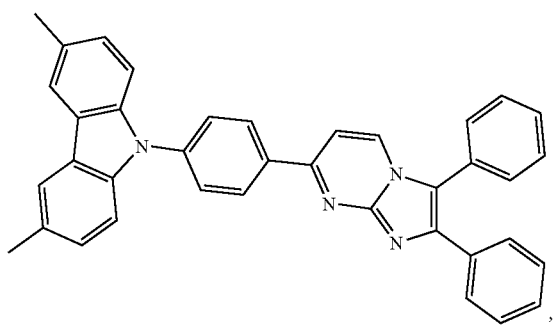
Compound 138
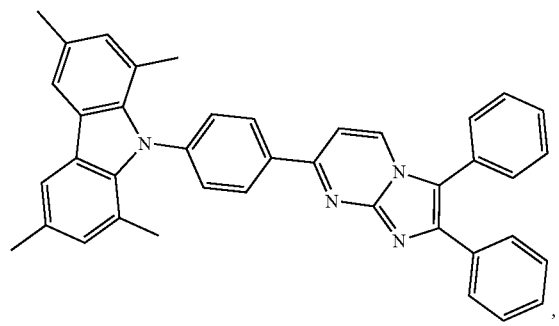
Compound 139
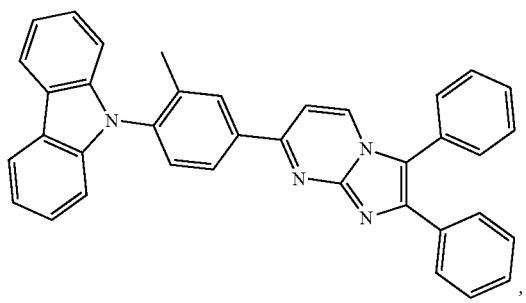

-continued
Compound 140
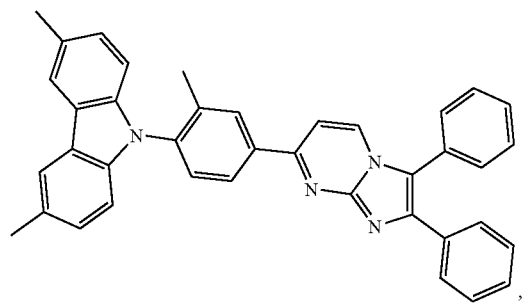
Compound 141
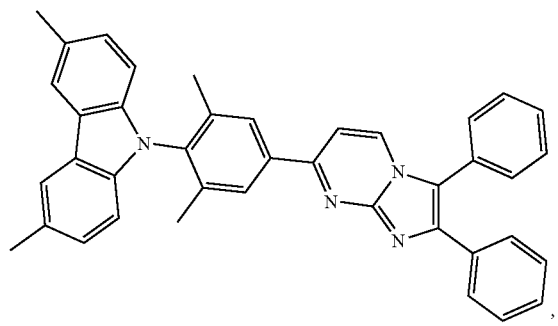
Compound 142
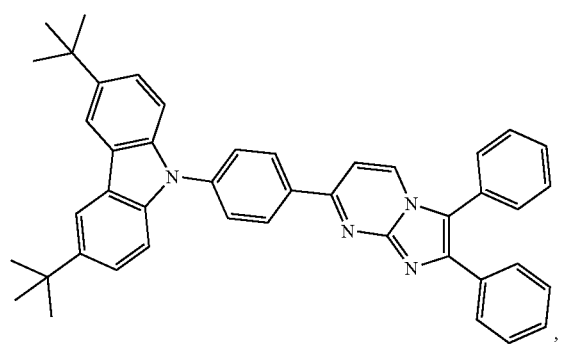
Compound 143
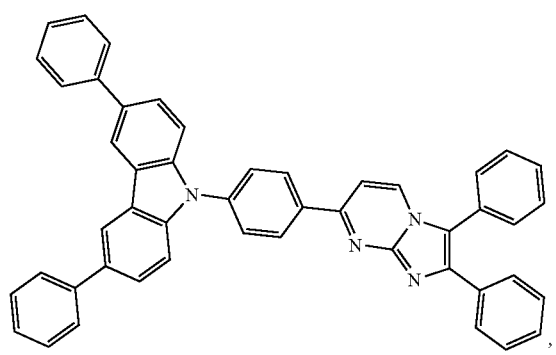
Compound 144
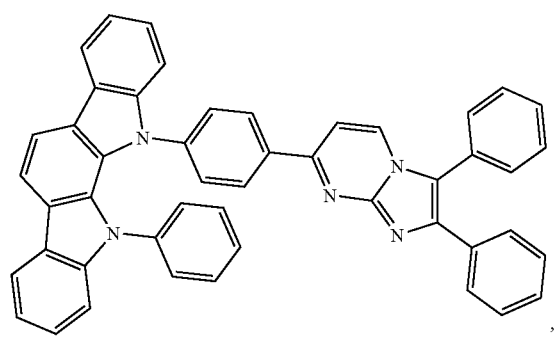
Compound 145
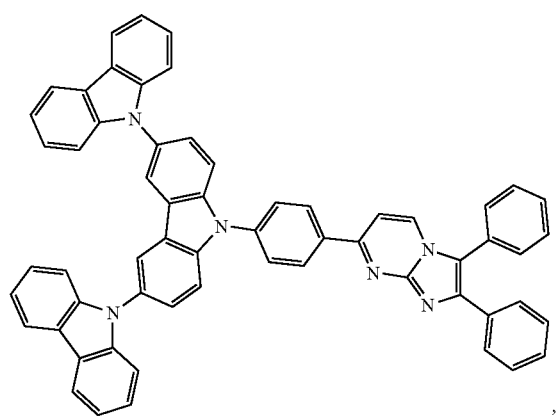

-continued
Compound 146
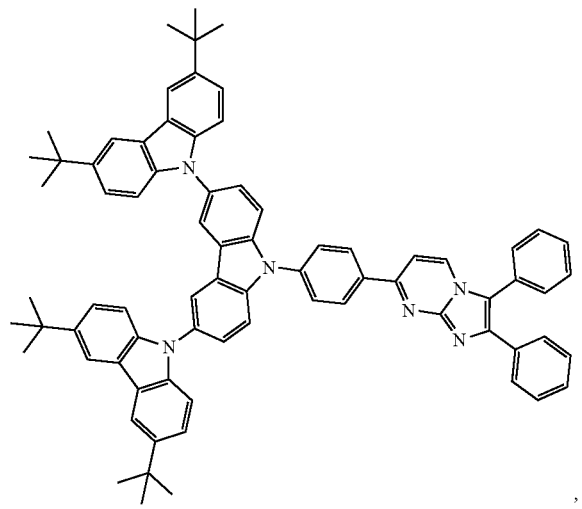
Compound 147
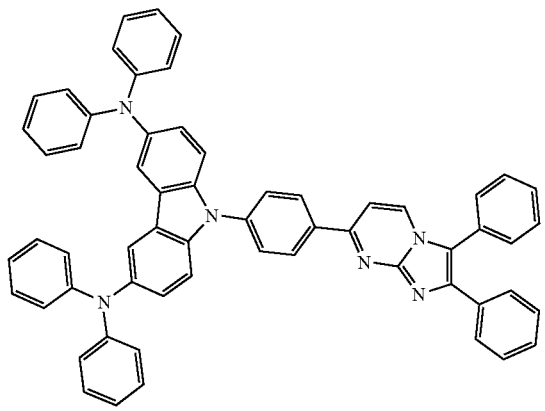
,
Compound 148
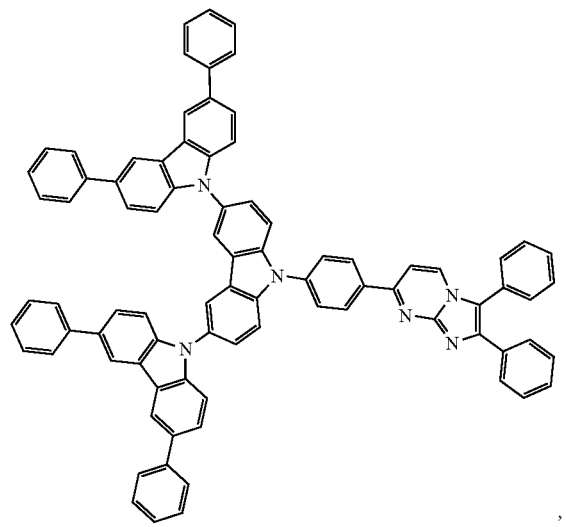
,
Compound 149
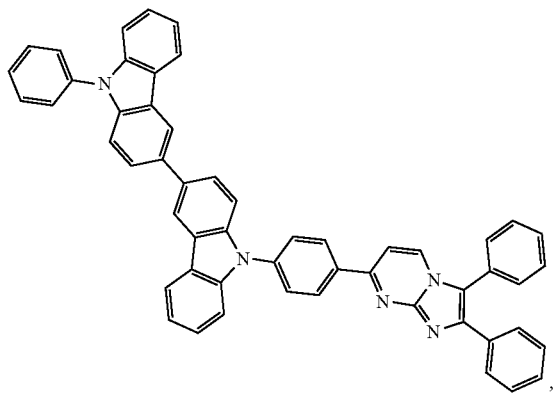
,
Compound 150
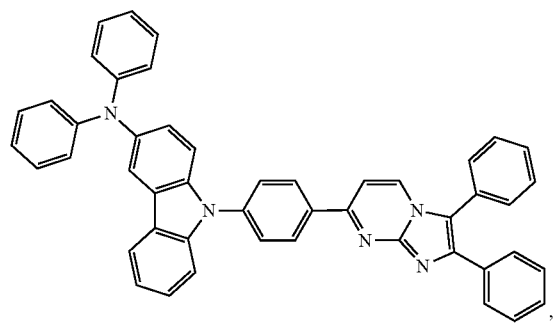
,
Compound 151
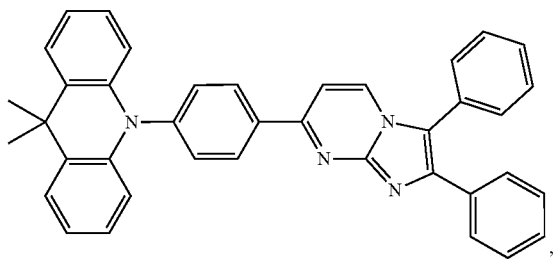
, -continued Compound 152

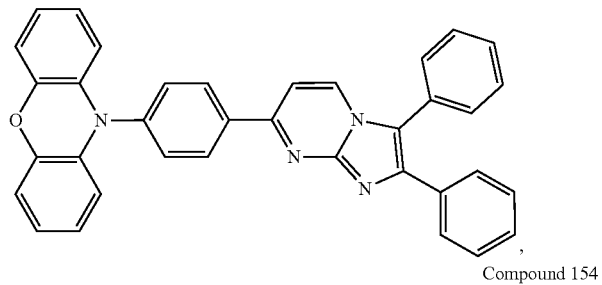

Compound 153

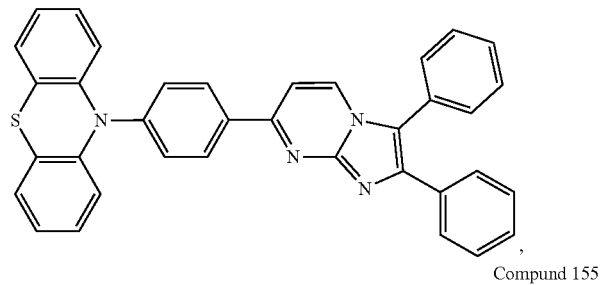

Compound 154

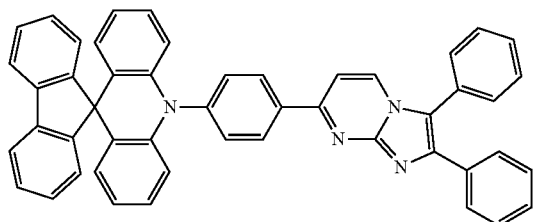

Compound 155

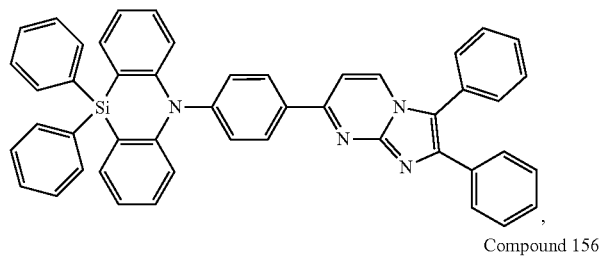

Compound 156

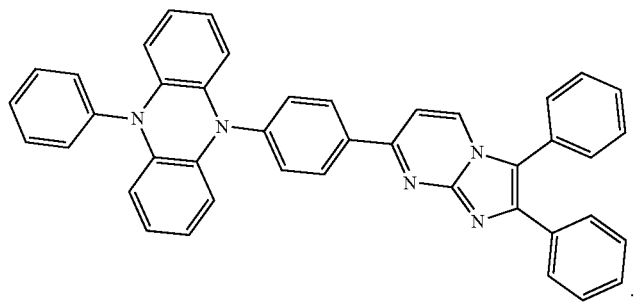

The present invention further provides an organic electroluminescent device, including an anode and a cathode which are oppositely arranged, and an organic functional layer disposed between the anode and the cathode, in which the organic functional layer includes a plurality of organic layers, and at least one of the organic layers contains one or more nitrogen-containing heterocyclic organic compounds as mentioned above.

In one embodiment, the plurality of organic layers include at least one layer of a hole injection layer, a hole transport layer, an electron blocking layer, a light emitting layer, a hole blocking layer, an electron transport layer, and an electron injection layer.

In one embodiment, the organic layers in the organic functional layer are formed by vacuum evaporation, molecular beam epitaxy, spin coating, dip coating, bar coating, or inkjet printing, and the anode and the cathode are both formed by evaporation or sputtering.

In one embodiment, the plurality of organic layers include the light emitting layer, and the light emitting layer includes a host light emitting material and the nitrogen-containing heterocyclic organic compound as mentioned above.

In one embodiment, the above nitrogen-containing heterocyclic organic compound in the organic layer is used alone, or in combination with the other compounds.

In comparison with the conventional materials and techniques, the present invention has the advantages and excellent effects as follows:

The nitrogen-containing heterocyclic organic compound provided in the present invention has superior thermal stability and high luminous efficiency, makes it possible to not use noble metal complexes, results in the reduction of production cost, and has broad application prospects. The organic electroluminescent device based on the nitrogen-containing heterocyclic organic compound of the present invention has higher luminous efficiency.

BRIEF DESCRIPTION OF DRAWINGS

The technical solutions and the other advantages of the present invention will be more clearly illustrated by the embodiments described in detail below with reference to the accompanying drawings. In the drawings, FIG. 1. is a diagram of the highest occupied molecular orbital of compound 35 according to one embodiment of the present invention.

DETAILED DESCRIPTION OF PREFERRED EMBODIMENTS

Figure 1:
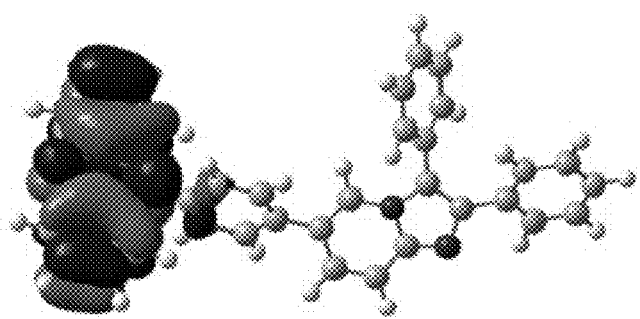
Figure 2:
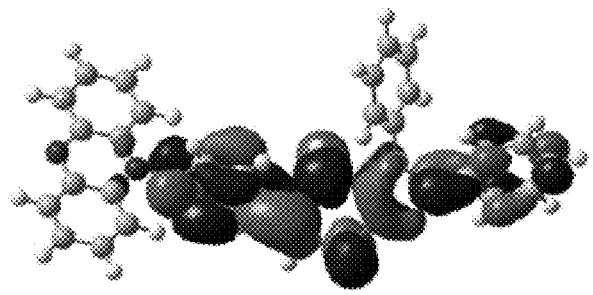
FIG. 2. is a diagram of the lowest unoccupied molecular orbital of compound 35 according to one embodiment of the present invention.

The raw materials used in the present invention but unannotated herein are commercially available. The preparations of the certain compounds are described in the examples. The present invention is further specifically described in the following embodiments, but the application of the present invention is not limited to that.

Example 1

Synthesis scheme of compound 1 is as follows:

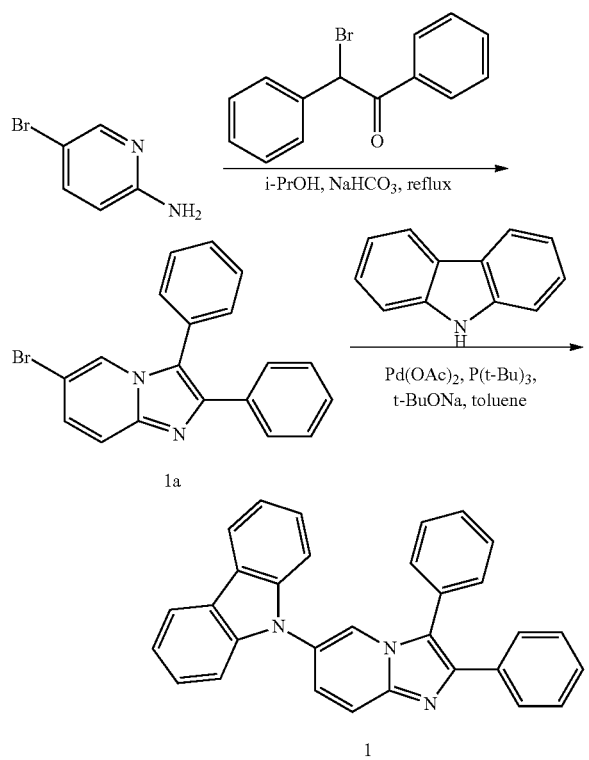

The synthesis method of compound 14 is similar to that of compound 1, except that carbazole used as the raw material in the second step is substituted with phenoxazine.

Example 2

Synthesis scheme of compound 35 is as follows:

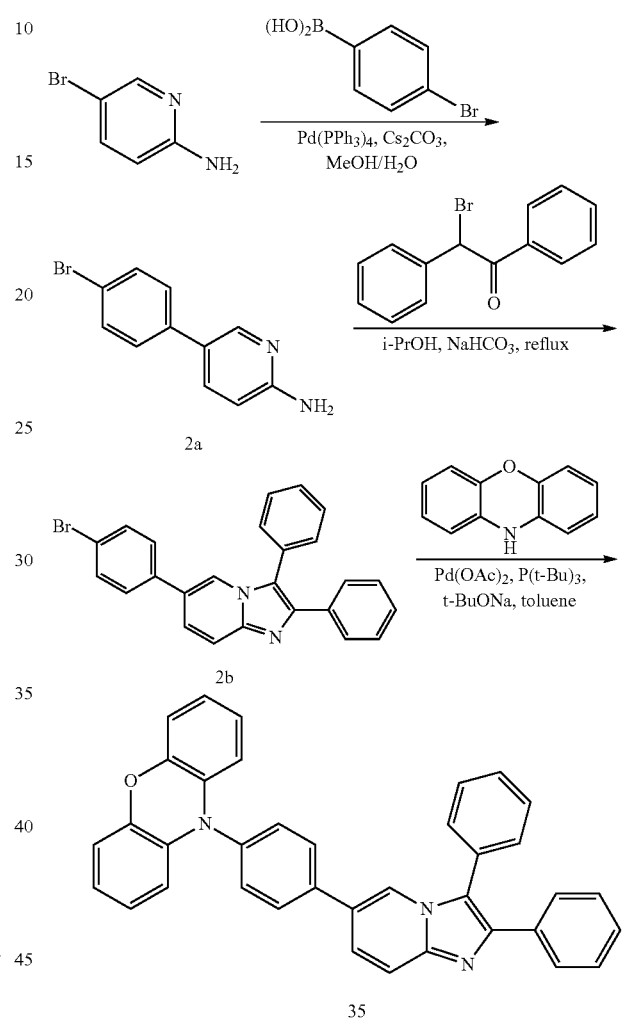

Synthesis of Compound 1a:

5-bromo-2-pyridinamine (8.60 g, 50.0 mmol), 2-bromo-2-phenylacetophenone (16.5 g, 60.0 mmol), and NaHCO$_3$ (5.04 g, 60.0 mmol) are dissolved in isopropanol (100 mL), and then stirred under reflux for 12 h. The mixture is subjected to the vacuum rotary evaporation for removing isopropanol. After then, dichloromethane (60 mL) and water (30 mL) are added into the solid residues. The organic phase is separated and washed twice with the saturated saline, followed by removing the solvent by the vacuum rotary evaporation; subsequently, it is extracted by the silica gel column chromatography to obtain the solid compound 1a (11.8 g, 34.0 mmol). A yield of compound 1a is 68%. By the gas chromatography-mass spectrometry, ESI-MS (m/z) is determined as 349.1.

Synthesis of Compound 1:

The compound 1a (3.48 g, 10.0 mmol), carbazole (1.84 g, 11.0 mmol), palladium(II) acetate (0.23 g, 1.0 mmol), sodium tert-butylate (3.36 g, 35.0 mmol), and tri-tert-butylphosphine (0.20 g, 1.0 mmol) are dissolved in toluene (60 mL), and then heated under reflux and atmospheric nitrogen for 10 h. The mixture is subjected to the vacuum rotary evaporation for removing the solvent. After then, dichloromethane is added into the residues under stirring; subsequently, it is filtered and extracted by the silica gel column chromatography to obtain the solid compound 1 (3.26 g, 7.5 mmol). A yield of compound 1 is 75%. By the gas chromatography-mass spectrometry, ESI-MS (m/z) is determined as 435.2.

Synthesis of Compound 2a:

5-bromo-2-pyridinamine (8.60 g, 50.0 mmol), 4-bromophenylboronic acid (11.0 g, 55.0 mmol), tetrakis(triphenylphosphine)palladium (2.89 g, 2.5 mmol), and caesium carbonate (10.8 g, 33.0 mmol) are dissolved in methanol/water (200 mL, 1/1), and then stirred under reflux for 12 h. After then, ethyl ethanoate and water are added into the mixture. The organic phase is separated and washed twice with the saturated saline, followed by removing the solvent by the vacuum rotary evaporation; subsequently, it is extracted by the silica gel column chromatography to obtain the solid compound 2a (7.84 g, 31.5 mmol). A yield of compound 2a is 63%. By the gas chromatography-mass spectrometry, ESI-MS (m/z) is determined as 248.7.

Synthesis of Compound 2b:

The compound 2a (12.5 g, 50.0 mmol), 2-bromo-2-phenylacetophenone (16.5 g, 60.0 mmol), and NaHCO$_3$ (5.04 g, 60.0 mmol) are dissolved in isopropanol (100 mL), and then stirred under reflux for 12 h. The mixture is subjected to the vacuum rotary evaporation for removing isopropanol. After then, dichloromethane (60 mL) and water (30 mL) are added into the solid residues. The organic phase is separated and washed twice with the saturated saline, followed by removing the solvent by the vacuum rotary evaporation; subsequently, it is extracted by the silica gel column chromatography to obtain the solid compound 2b (13.8 g, 32.5 mmol). A yield of compound 2b is 65%. By the gas chromatography-mass spectrometry, ESI-MS (m/z) is determined as 425.1.

Synthesis of Compound 35:

The compound 2b (4.25 g, 10.0 mmol), phenoxazine (1.84 g, 11.0 mmol), palladium(II) acetate (0.23 g, 1.0 mmol), sodium tert-butylate (3.36 g, 35.0 mmol), and tri-tert-butylphosphine (0.20 g, 1.0 mmol) are dissolved in toluene (60 mL), and then heated under reflux and atmospheric nitrogen for 10 h. The mixture is subjected to the vacuum rotary evaporation for removing the solvent. After then, dichloromethane is added into the residues under stirring; subsequently, it is filtered and extracted by the silica gel column chromatography to obtain the solid compound 35 (3.80 g, 7.2 mmol). A yield of compound 35 is 72%. By the gas chromatography-mass spectrometry, ESI-MS (m/z) is determined as 527.3.

The synthesis method of compound 28 is similar to that of compound 35, except that phenoxazine used as the raw material in the third step is substituted with 9,3':6',9''-tercarbazole.

Example 3

Synthesis scheme of compound 53 is as follows:

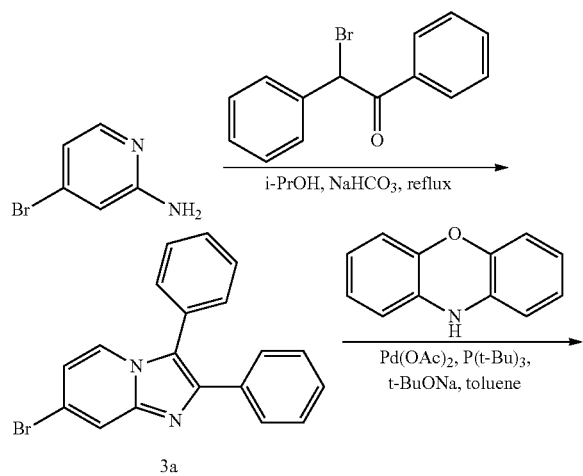

Synthesis of Compound 3a:

4-bromo-2-pyridinamine (8.60 g, 50.0 mmol), 2-bromo-2-phenylacetophenone (16.5 g, 60.0 mmol), and NaHCO₃ (5.04 g, 60.0 mmol) are dissolved in isopropanol (100 mL), and then stirred under reflux for 12 h. The mixture is subjected to the vacuum rotary evaporation for removing isopropanol. After then, dichloromethane (60 mL) and water (30 mL) are added into the solid residues. The organic phase is separated and washed twice with the saturated saline, followed by removing the solvent by the vacuum rotary evaporation; subsequently, it is extracted by the silica gel column chromatography to obtain the solid compound 3a (12.2 g, 35.0 mmol). A yield of compound 3a is 70%. By the gas chromatography-mass spectrometry, ESI-MS (m/z) is determined as 349.3.

Synthesis of Compound 53:

The compound 3a (3.48 g, 10.0 mmol), phenoxazine (2.01 g, 11.0 mmol), palladium(II) acetate (0.23 g, 1.0 mmol), sodium tert-butylate (3.36 g, 35.0 mmol), and tri-tert-butylphosphine (0.20 g, 1.0 mmol) are dissolved in toluene (60 mL), and then heated under reflux and atmospheric nitrogen for 10 h. The mixture is subjected to the vacuum rotary evaporation for removing the solvent. After then, dichloromethane is added into the residues under stirring; subsequently, it is filtered and extracted by the silica gel column chromatography to obtain the solid compound 53 (3.20 g, 7.1 mmol). A yield of compound 53 is 71%. By the gas chromatography-mass spectrometry, ESI-MS (m/z) is determined as 451.2.

The synthesis method of compound 55 is similar to that of compound 53, except that phenoxazine used as the raw material in the second step is substituted with 10H-spiro[acridine-9,9'-fluorene].

Example 4

Synthesis scheme of compound 74 is as follows:

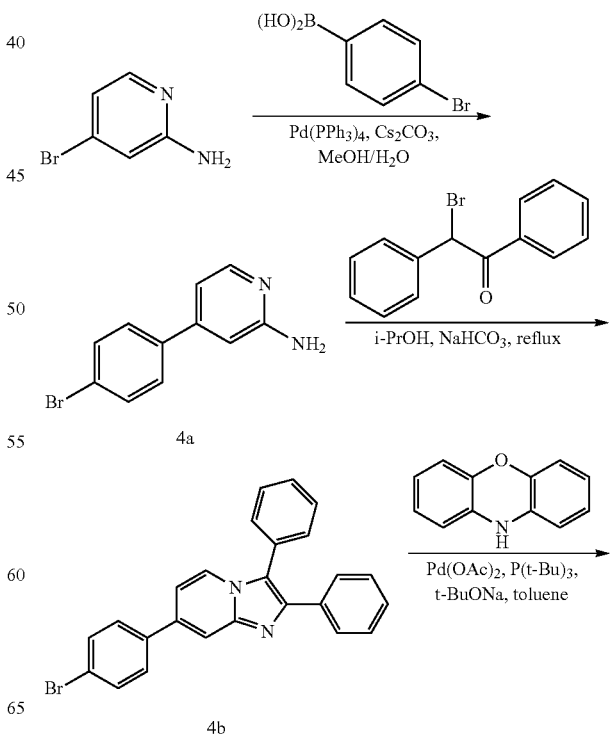

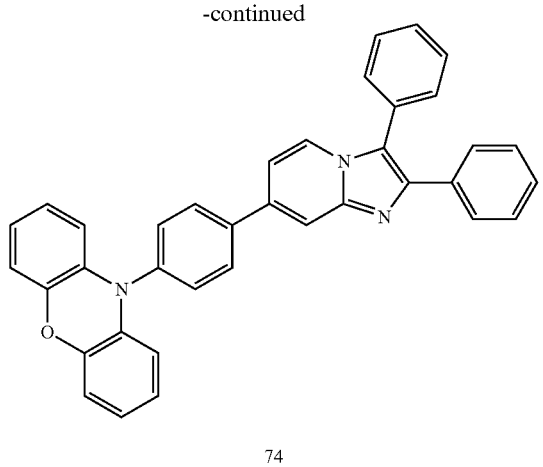

74

Synthesis of Compound 4a:

4-bromo-2-pyridinamine (8.60 g, 50.0 mmol), 4-bromophenylboronic acid (11.0 g, 55.0 mmol), tetrakis(triphenylphosphine)palladium (2.89 g, 2.5 mmol), and caesium carbonate (10.8 g, 33.0 mmol) are dissolved in methanol/water (200 mL, 1/1), and then stirred under reflux for 12 h. After then, ethyl ethanoate and water are added into the mixture. The organic phase is separated and washed twice with the saturated saline, followed by removing the solvent by the vacuum rotary evaporation; subsequently, it is extracted by the silica gel column chromatography to obtain the solid compound 4a (8.08 g, 32.5 mmol). A yield of compound 4a is 65%. By the gas chromatography-mass spectrometry, ESI-MS (m/z) is determined as 248.5.

Synthesis of Compound 4b:

The compound 4a (12.5 g, 50.0 mmol), 2-bromo-2-phenylacetophenone (16.5 g, 60.0 mmol), and NaHCO$_3$ (5.04 g, 60.0 mmol) are dissolved in isopropanol (100 mL), and then stirred under reflux for 12 h. The mixture is subjected to the vacuum rotary evaporation for removing isopropanol. After then, dichloromethane (60 mL) and water (30 mL) are added into the solid residues. The organic phase is separated and washed twice with the saturated saline, followed by removing the solvent by the vacuum rotary evaporation; subsequently, it is extracted by the silica gel column chromatography to obtain the solid compound 4b (12.8 g, 30.0 mmol). A yield of compound 4b is 60%. By the gas chromatography-mass spectrometry, ESI-MS (m/z) is determined as 425.3.

Synthesis of Compound 74:

The compound 4b (4.25 g, 10.0 mmol), phenoxazine (1.84 g, 11.0 mmol), palladium(II) acetate (0.23 g, 1.0 mmol), sodium tert-butylate (3.36 g, 35.0 mmol), and tri-tert-butylphosphine (0.20 g, 1.0 mmol) are dissolved in toluene (60 mL), and then heated under reflux and atmospheric nitrogen for 10 h. The mixture is subjected to the vacuum rotary evaporation for removing the solvent. After then, dichloromethane is added into the residues under stirring; subsequently, it is filtered and extracted by the silica gel column chromatography to obtain the solid compound 74 (3.95 g, 7.5 mmol). A yield of compound 74 is 75%. By the gas chromatography-mass spectrometry, ESI-MS (m/z) is determined as 527.3.

The synthesis method of compound 67 is similar to that of compound 74, except that phenoxazine used as the raw material in the third step is substituted with 9,3':6',9''-tercarbazole.

Example 5

Synthesis scheme of compound 92 is as follows:

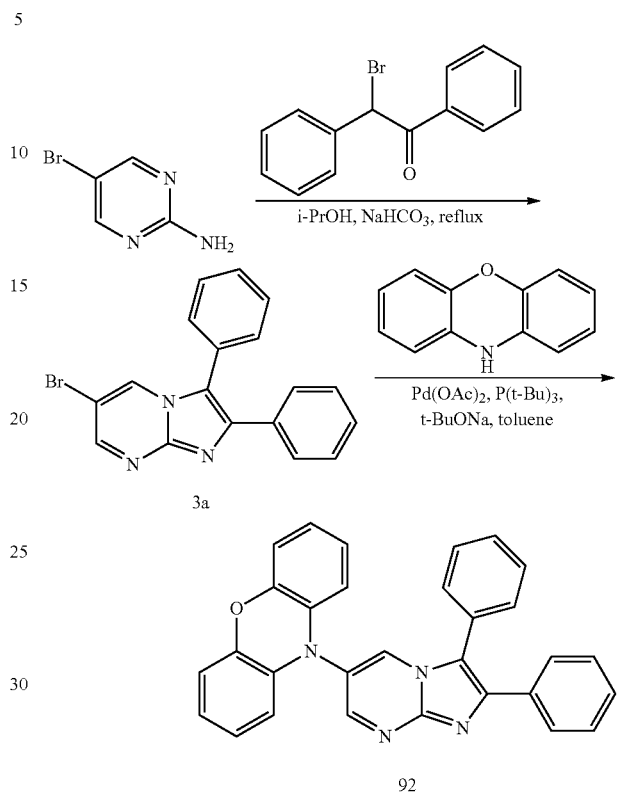

Synthesis of Compound 5a:

5-bromo-2-pyrimidinamine (8.70 g, 50.0 mmol), 2-bromo-2-phenylacetophenone (16.5 g, 60.0 mmol), and NaHCO$_3$ (5.04 g, 60.0 mmol) are dissolved in isopropanol (100 mL), and then stirred under reflux for 12 h. The mixture is subjected to the vacuum rotary evaporation for removing isopropanol. After then, dichloromethane (60 mL) and water (30 mL) are added into the solid residues. The organic phase is separated and washed twice with the saturated saline, followed by removing the solvent by the vacuum rotary evaporation; subsequently, it is extracted by the silica gel column chromatography to obtain the solid compound 5a (13.1 g, 37.5 mmol). A yield of compound 5a is 75%. By the gas chromatography-mass spectrometry, ESI-MS (m/z) is determined as 350.1.

Synthesis of Compound 92:

The compound 5a (3.5 g, 10.0 mmol), phenoxazine (2.01 g, 11.0 mmol), palladium(II) acetate (0.23 g, 1.0 mmol), sodium tert-butylate (3.36 g, 35.0 mmol), and tri-tert-butylphosphine (0.20 g, 1.0 mmol) are dissolved in toluene (60 mL), and then heated under reflux and atmospheric nitrogen for 10 h. The mixture is subjected to the vacuum rotary evaporation for removing the solvent. After then, dichloromethane is added into the residues under stirring; subsequently, it is filtered and extracted by the silica gel column chromatography to obtain the solid compound 92 (3.07 g, 6.8 mmol). A yield of compound 92 is 68%. By the gas chromatography-mass spectrometry, ESI-MS (m/z) is determined as 452.2.

The synthesis method of compound 94 is similar to that of compound 92, except that phenoxazine used as the raw material in the second step is substituted with 10H-spiro[acridine-9,9'-fluorene].

Example 6

Synthesis scheme of compound 113 is as follows:

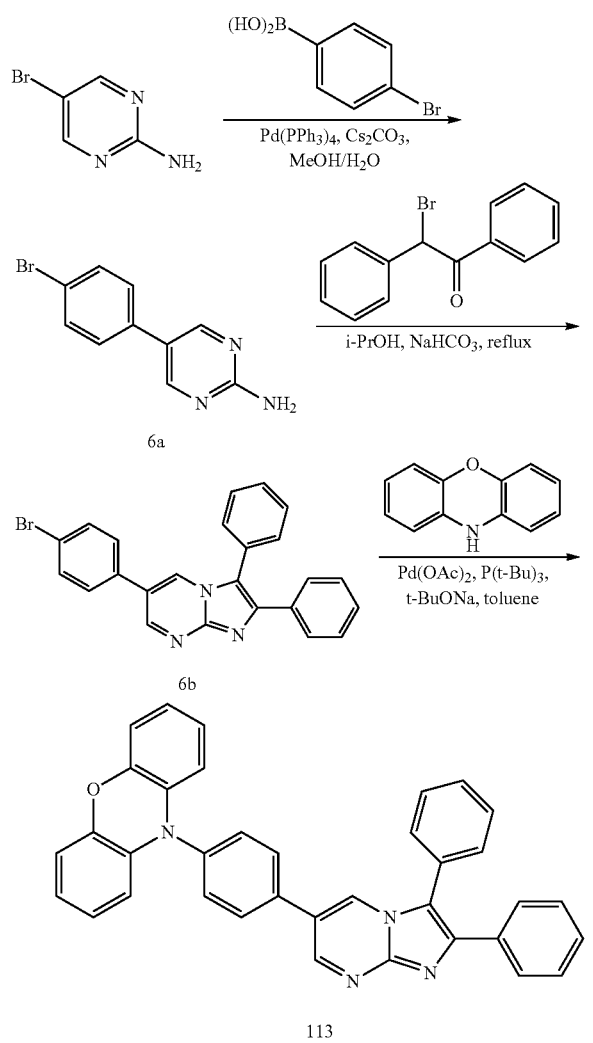

Synthesis of Compound 6a:

5-bromo-2-pyrimidinamine (8.70 g, 50.0 mmol), 4-bromophenylboronic acid (11.0 g, 55.0 mmol), tetrakis(triphenylphosphine)palladium (2.89 g, 2.5 mmol), and caesium carbonate (10.8 g, 33.0 mmol) are dissolved in methanol/water (200 mL, 1/1), and then stirred under reflux for 12 h. After then, ethyl ethanoate and water are added into the mixture. The organic phase is separated and washed twice with the saturated saline, followed by removing the solvent by the vacuum rotary evaporation; subsequently, it is extracted by the silica gel column chromatography to obtain the solid compound 6a (7.75 g, 31.0 mmol). A yield of compound 6a is 62%. By the gas chromatography-mass spectrometry, ESI-MS (m/z) is determined as 249.5.

Synthesis of Compound 6b:

The compound 6a (12.5 g, 50.0 mmol), 2-bromo-2-phenylacetophenone (16.5 g, 60.0 mmol), and NaHCO$_3$ (5.04 g, 60.0 mmol) are dissolved in isopropanol (100 mL), and then stirred under reflux for 12 h. The mixture is subjected to the vacuum rotary evaporation for removing isopropanol. After then, dichloromethane (60 mL) and water (30 mL) are added into the solid residues. The organic phase is separated and washed twice with the saturated saline, followed by removing the solvent by the vacuum rotary evaporation; subsequently, it is extracted by the silica gel column chromatography to obtain the solid compound 6b (13.8 g, 32.5 mmol). A yield of compound 6b is 65%. By the gas chromatography-mass spectrometry, ESI-MS (m/z) is determined as 426.3.

Synthesis of Compound 113:

The compound 6b (4.26 g, 10.0 mmol), phenoxazine (1.84 g, 11.0 mmol), palladium(II) acetate (0.23 g, 1.0 mmol), sodium tert-butylate (3.36 g, 35.0 mmol), and tri-tert-butylphosphine (0.20 g, 1.0 mmol) are dissolved in toluene (60 mL), and then heated under reflux and atmospheric nitrogen for 10 h. The mixture is subjected to the vacuum rotary evaporation for removing the solvent. After then, dichloromethane is added into the residues under stirring; subsequently, it is filtered and extracted by the silica gel column chromatography to obtain the solid compound 113 (3.75 g, 7.1 mmol). A yield of compound 113 is 71%. By the gas chromatography-mass spectrometry, ESI-MS (m/z) is determined as 528.3.

The synthesis method of compound 106 is similar to that of compound 113, except that phenoxazine used as the raw material in the third step is substituted with 9,3':6',9''-tercarbazole.

Example 7

Synthesis scheme of compound 131 is as follows:

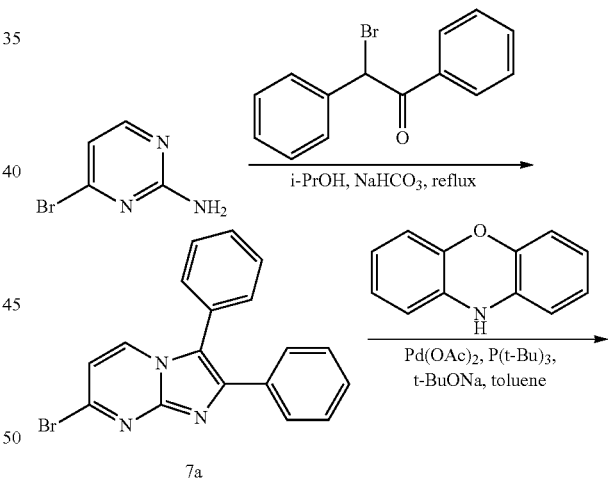

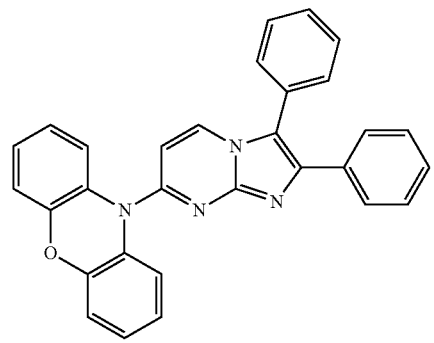

Synthesis of Compound 7a:

4-bromo-2-pyrimidinamine (8.70 g, 50.0 mmol), 2-bromo-2-phenylacetophenone (16.5 g, 60.0 mmol), and NaHCO$_3$ (5.04 g, 60.0 mmol) are dissolved in isopropanol (100 mL), and then stirred under reflux for 12 h. The mixture is subjected to the vacuum rotary evaporation for removing isopropanol. After then, dichloromethane (60 mL) and water (30 mL) are added into the solid residues. The organic phase is separated and washed twice with the saturated saline, followed by removing the solvent by the vacuum rotary evaporation; subsequently, it is extracted by the silica gel column chromatography to obtain the solid compound 7a (13.3 g, 38.0 mmol). A yield of compound 7a is 76%. By the gas chromatography-mass spectrometry, ESI-MS (m/z) is determined as 350.2.

Synthesis of Compound 131:

The compound 7a (3.5 g, 10.0 mmol), phenoxazine (2.01 g, 11.0 mmol), palladium(II) acetate (0.23 g, 1.0 mmol), sodium tert-butylate (3.36 g, 35.0 mmol), and tri-tert-butylphosphine (0.20 g, 1.0 mmol) are dissolved in toluene (60 mL), and then heated under reflux and atmospheric nitrogen for 10 h. The mixture is subjected to the vacuum rotary evaporation for removing the solvent. After then, dichloromethane is added into the residues under stirring; subsequently, it is filtered and extracted by the silica gel column chromatography to obtain the solid compound 131 (3.26 g, 7.2 mmol). A yield of compound 131 is 72%. By the gas chromatography-mass spectrometry, ESI-MS (m/z) is determined as 452.1.

The synthesis method of compound 133 is similar to that of compound 131, except that phenoxazine used as the raw material in the second step is substituted with 10H-spiro[acridine-9,9'-fluorene].

Example 8

Synthesis scheme of compound 152 is as follows:

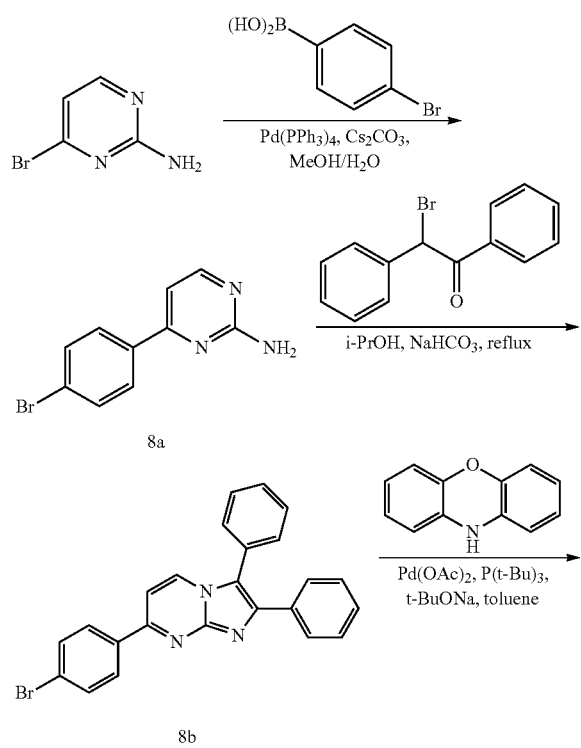

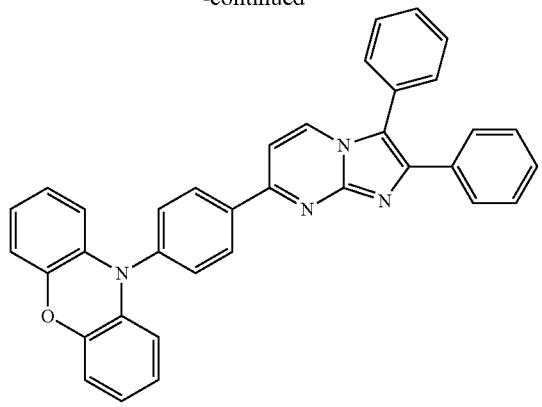

152

Synthesis of Compound 8a:

4-bromo-2-pyrimidinamine (8.70 g, 50.0 mmol), 4-bromophenylboronic acid (11.0 g, 55.0 mmol), tetrakis(triphenylphosphine)palladium (2.89 g, 2.5 mmol), and caesium carbonate (10.8 g, 33.0 mmol) are dissolved in methanol/water (200 mL, 1/1), and stirred under reflux for 12 h. After then, ethyl ethanoate and water are added into the mixture. The organic phase is separated and washed twice with the saturated saline, followed by removing the solvent by the vacuum rotary evaporation; subsequently, it is extracted by the silica gel column chromatography to obtain the solid compound 8a (7.50 g, 30.0 mmol). A yield of compound 8a is 60%. By the gas chromatography-mass spectrometry, ESI-MS (m/z) is determined as 249.8.

Synthesis of Compound 8b:

The compound 8a (12.5 g, 50.0 mmol), 2-bromo-2-phenylacetophenone (16.5 g, 60.0 mmol), and NaHCO$_3$ (5.04 g, 60.0 mmol) are dissolved in isopropanol (100 mL), and then stirred under reflux for 12 h. The mixture is subjected to the vacuum rotary evaporation for removing isopropanol. After then, dichloromethane (60 mL) and water (30 mL) are added into the solid residues. The organic phase is separated and washed twice with the saturated saline, followed by removing the solvent by the vacuum rotary evaporation; subsequently, it is extracted by the silica gel column chromatography to obtain the solid compound 8b (13.2 g, 31.0 mmol). A yield of compound 8b is 62%. By the gas chromatography-mass spectrometry, ESI-MS (m/z) is determined as 426.1.

Synthesis of Compound 152:

The compound 8b (4.26 g, 10.0 mmol), phenoxazine (1.84 g, 11.0 mmol), palladium(II) acetate (0.23 g, 1.0 mmol), sodium tert-butylate (3.36 g, 35.0 mmol), and tri-tert-butylphosphine (0.20 g, 1.0 mmol) are dissolved in toluene (60 mL), and then heated under reflux and atmospheric nitrogen for 10 h. The mixture is subjected to the vacuum rotary evaporation for removing the solvent. After then, dichloromethane is added into the residues under stirring; subsequently, it is filtered and extracted by the silica gel column chromatography to obtain the solid compound 152 (3.85 g, 7.3 mmol). A yield of compound 152 is 73%. By the gas chromatography-mass spectrometry, ESI-MS (m/z) is determined as 528.2.

The synthesis method of compound 145 is similar to that of compound 152, except that phenoxazine used as the raw material in the third step is substituted with 9,3':6',9''-tercarbazole.

Examples 9-14

The compounds obtained from the above Examples are used in the manufacture of an organic electroluminescent device.

Figure 3:
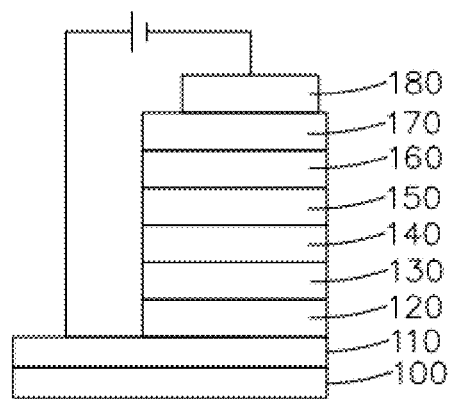
FIG. 3. is a diagram of the structure of the organic electroluminescent device of the present invention.

Substrate 100 having anode 110 formed thereon is provided, in which the anode 110 is transparent and conductive, made of indium tin oxide (ITO), and substrate 100 is a glass substrate. Substrate 100 is washed with distilled water, acetone, and isopropanol by ultrasounds, and then dried in an oven. Subsequently, the substrate 100 is exposed to ultraviolet light for 20 mins, and then placed in a vacuum evaporator. Under the condition of the degree of vacuum of $2*10^{-5}$ Pa, each layer is deposited. First, 10 nm of 2,3,6,7,10,11-hexacyano-1,4,5,8,9,12-hexaazatriphenylene (HATCN) is deposited to form a hole injection layer 120. Next, 60 nm of naphtylphenylbenzidine (NPB) is deposited to form a hole transport layer 130, and 10 nm of 4,4',4"-tris(N-carbazolyl)triphenylamine (TCTA) is deposited to form an electron blocking layer 140. After then, 4,4'-bis(N-carbazolyl)-1,1'-biphenyl (CBP) as host material (94 wt %) and the nitrogen-containing heterocyclic organic compound of the present invention as doped material (6 wt %) are simultaneously deposited on the electron blocking layer 140 to form 30 nm of a light emitting layer 150. Further, 40 nm of 1,3,5-tris(1-phenyl-1H-benzimidazol-2-yl)benzene (TPBi) is deposed on the light emitting layer 150 to act as an electron transport layer 160. Finally, 1 nm of LiF is deposited to act as an electron injection layer 170, and 100 nm of aluminum (Al) is deposited to act as a cathode 180 of the device. The organic electroluminescent device manufactured by this process is shown in FIG. 3, and specifically has the following structure:

ITO (100 nm)/HATCN (10 nm)/NPB (60 nm)/TCTA (10 nm)/CBP: the nitrogen-containing heterocyclic organic compound of the present invention (94 wt %:6 wt %, 30 nm)/TPBi (40 nm)/LiF (1 nm)/Al (100 nm).

Comparison Examples 1-2

The manufacture processes of the organic electroluminescent devices of Comparison examples 1-2 are similar to that of the devices of Examples 9-14, except that green fluorescent dopant C-545MT and green phosphorescent dopant Ir(ppy)3 are used as doped material, respectively, instead of the nitrogen-containing heterocyclic organic compounds of the present invention.

In the above examples and comparison examples, the structure formulas of the mentioned compounds are shown below:

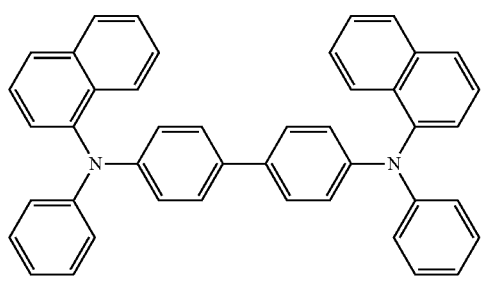

NPB

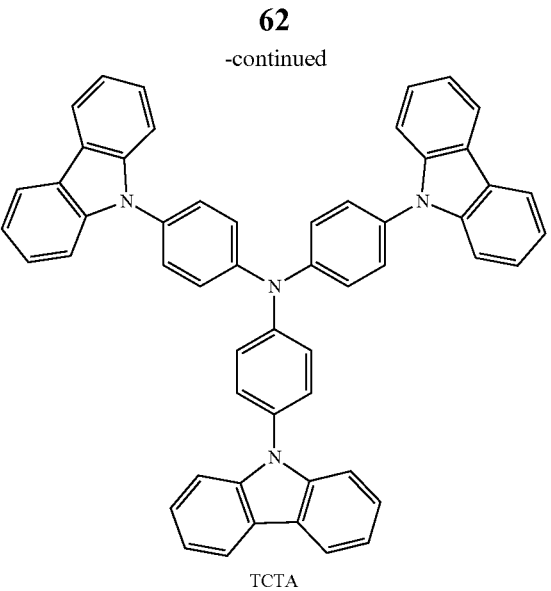

TCTA

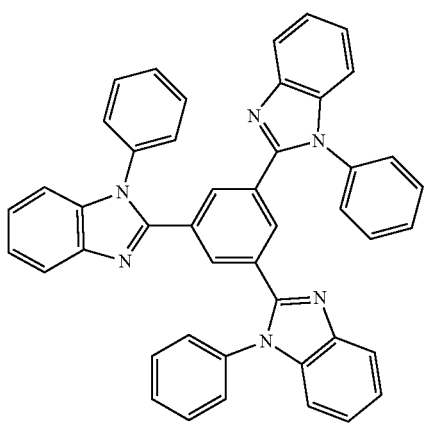

TPBi

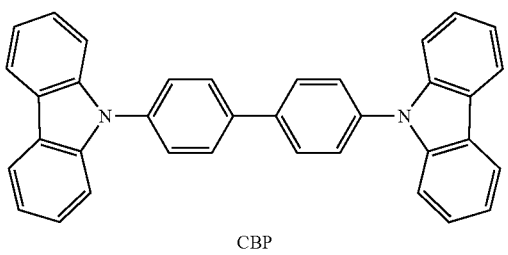

CBP

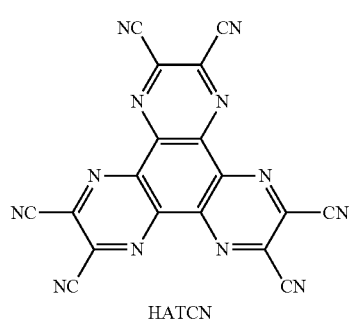

HATCN

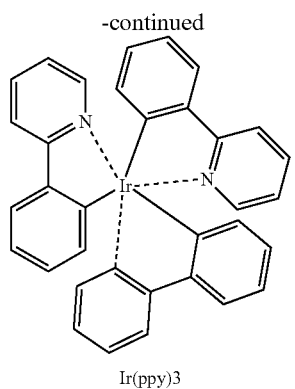

Ir(ppy)3

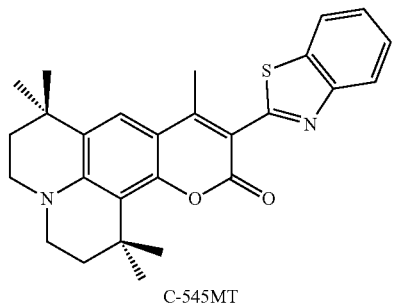

C-545MT

Evaluation of the properties of the organic electroluminescent devices:

The current of the organic electroluminescent device under the different voltages is determined by Keithley 2400 Sourcemeter. Further, the current density is calculated by dividing the current by the light emitting area. The brightness and the radiant energy density of the organic electroluminescent device under the different voltages are determined by Photo Research PR655. Based on the current density and the brightness of the organic electroluminescent device under the different voltages, the current efficiency (cd/A) and the external quantum efficiency (EQE) of the organic electroluminescent device could be decided. The current efficiency and the external quantum efficiency of the obtained organic electroluminescent device at 1000 cd/m² of brightness are shown in Table 1.

TABLE 1

The property reports of the organic electroluminescent devices obtained from the examples and the comparison examples

|  | Doped material in light emitting layer | Current efficiency (cd/A) | External quantum efficiency (%) | Color |
| --- | --- | --- | --- | --- |
| Example 9 | Compound 14 | 34.5 | 12.5 | Green |
| Example 10 | Compound 35 | 45.2 | 14.5 | Green |
| Example 11 | Compound 53 | 43.0 | 13.8 | Green |
| Example 12 | Compound 74 | 56.6 | 17.5 | Green |
| Example 13 | Compound 106 | 51.5 | 15.5 | Green |
| Example 14 | Compound 145 | 52.4 | 16.0 | Green |
| Comparison example 1 | C-545MT | 7.8 | 3.5 | Green |
| Comparison example 2 | Ir(ppy)3 | 55.0 | 15.4 | Green |

According to Table 1, the organic electroluminescent device containing the nitrogen-containing heterocyclic organic compound of the present invention as a novel organic light emitting material exhibits high luminous efficiency, implying that the compound is a TADF light emitting material having excellent properties.

From the above, the organic electroluminescent device containing the nitrogen-containing heterocyclic organic compound of the present invention has excellent luminous properties.

The above examples are the preferred embodiments of the present invention, but not intended to limit the application of the present invention. Any other changes, modifications, substitutions, combinations, and simplifications without departing from the spirit and principle of the present invention shall be regarded as equivalents of the present invention and shall fall within the claimed scope of the present invention.

What is claimed is:

1. A nitrogen-containing heterocyclic organic compound, having a chemical structure represented by the following formula (I):

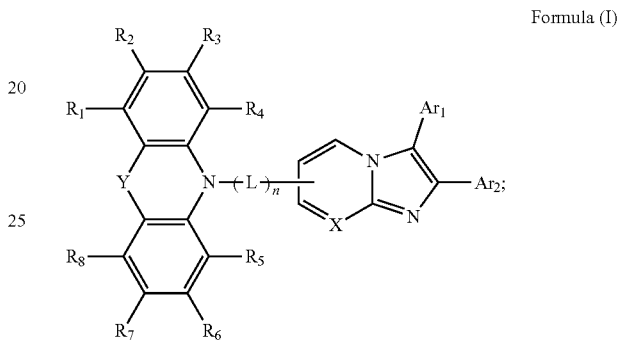

Formula (I)

wherein,

X is N or CH;

Y is a single bond, O, S, an imino, a methylene, a methylidenesilane group, a substituted imino, a substituted methylene, or a substituted methylidenesilane group, and the substituents in the substituted imino, the substituted methylene, and the substituted methylidenesilane group are each independently selected from one of a hydrogen, a deuteron, a $C_1$-$C_{30}$ alkyl, a $C_1$-$C_{30}$ alkyl substituted with a heteroatom, a $C_6$-$C_{30}$ aryl, and a $C_3$-$C_{30}$ heteroaryl;

L, $Ar_1$, and $Ar_2$ are each independently selected from one of a $C_6$-$C_{30}$ aryl, a $C_3$-$C_{30}$ heteroaryl, a substituted $C_6$-$C_{30}$ aryl, and a substituted $C_3$-$C_{30}$ heteroaryl;

n is an integer from 0 to 3;

$R_1$ to $R_8$ are each independently selected from one of a hydrogen, a deuteron, a halogen, a $C_1$-$C_{30}$ alkyl, a $C_1$-$C_{30}$ alkyl substituted with a heteroatom, a $C_6$-$C_{30}$ aryl, and a $C_3$-$C_{30}$ heteroaryl.

2. The nitrogen-containing heterocyclic organic compound according to claim 1, having a chemical structure represented by the following formula (II):

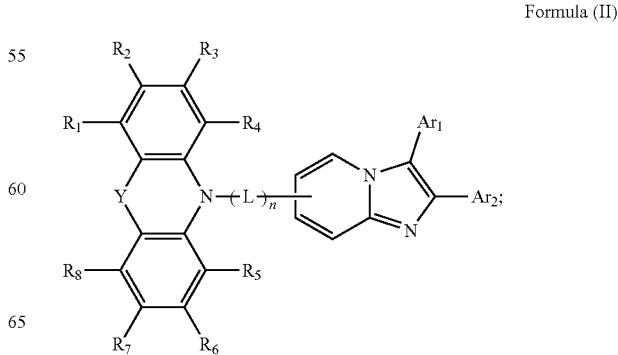

Formula (II)

wherein,
Y is a single bond, O, S, an imino, a methylene, a methylidenesilane group, a substituted imino, a substituted methylene, or a substituted methylidenesilane group, and the substituents in the substituted imino, the substituted methylene, and the substituted methylidenesilane group are each independently selected from one of a hydrogen, a deuteron, a $C_1$-$C_{30}$ alkyl, a $C_1$-$C_{30}$ alkyl substituted with a heteroatom, a $C_6$-$C_{30}$ aryl, and a $C_3$-$C_{30}$ heteroaryl;

L, $Ar_1$, and $Ar_2$ are each independently selected from one of a $C_6$-$C_{30}$ aryl, a $C_3$-$C_{30}$ heteroaryl, a substituted $C_6$-$C_{30}$ aryl, and a substituted $C_3$-$C_{30}$ heteroaryl;

n is an integer from 0 to 3;

$R_1$ to $R_8$ are each independently selected from one of a hydrogen, a deuteron, a halogen, a $C_1$-$C_{30}$ alkyl, a $C_1$-$C_{30}$ alkyl substituted with a heteroatom, a $C_6$-$C_{30}$ aryl, and a $C_3$-$C_{30}$ heteroaryl.

3. The nitrogen-containing heterocyclic organic compound according to claim 1, having a chemical structure represented by the following formula (III):

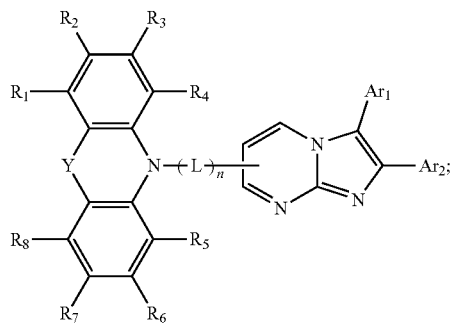

Formula (III)

wherein,
Y is a single bond, O, S, an imino, a methylene, a methylidenesilane group, a substituted imino, a substituted methylene, or a substituted methylidenesilane group, and the substituents in the substituted imino, the substituted methylene, and the substituted methylidenesilane group are each independently selected from one of a hydrogen, a deuteron, a $C_1$-$C_{30}$ alkyl, a $C_1$-$C_{30}$ alkyl substituted with a heteroatom, a $C_6$-$C_{30}$ aryl, and a $C_3$-$C_{30}$ heteroaryl;

L, $Ar_1$, and $Ar_2$ are each independently selected from one of a $C_6$-$C_{30}$ aryl, a $C_3$-$C_{30}$ heteroaryl, a substituted $C_6$-$C_{30}$ aryl, and a substituted $C_3$-$C_{30}$ heteroaryl;

n is an integer from 0 to 3;

$R_1$ to $R_8$ are each independently selected from one of a hydrogen, a deuteron, a halogen, a $C_1$-$C_{30}$ alkyl, a $C_1$-$C_{30}$ alkyl substituted with a heteroatom, a $C_6$-$C_{30}$ aryl, and a $C_3$-$C_{30}$ heteroaryl.

4. The nitrogen-containing heterocyclic organic compound according to claim 1, wherein the $C_6$-$C_{30}$ aryl is phenyl, naphthyl, or biphenyl.

5. The nitrogen-containing heterocyclic organic compound according to claim 1, wherein the $C_3$-$C_{30}$ heteroaryl is pyridyl, pyrimidinyl, imidazolyl, oxazolyl, triazinyl, carbazolyl, or diphenylamino.

6. The nitrogen-containing heterocyclic organic compound according to claim 1, being selected from one of Compounds 1 to 156, and each structural formula of Compounds 1 to 156 is as follows:

Compound 1

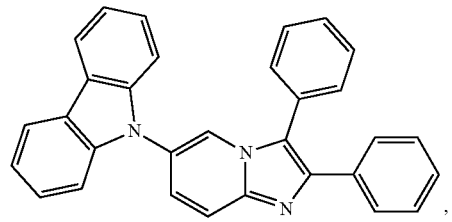

,

Compound 2

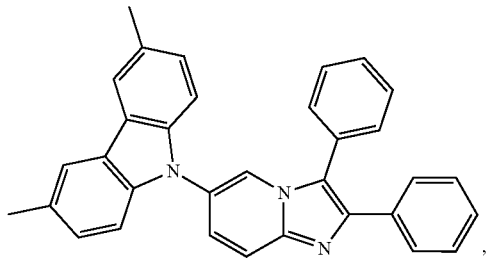

,

Compound 3

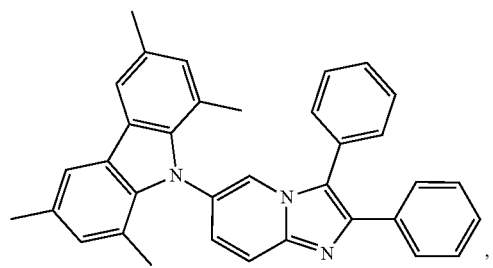

,

Compound 4

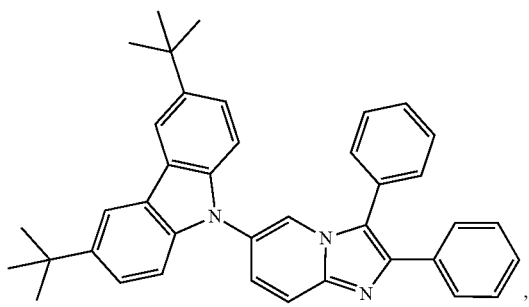

,

-continued
Compound 5
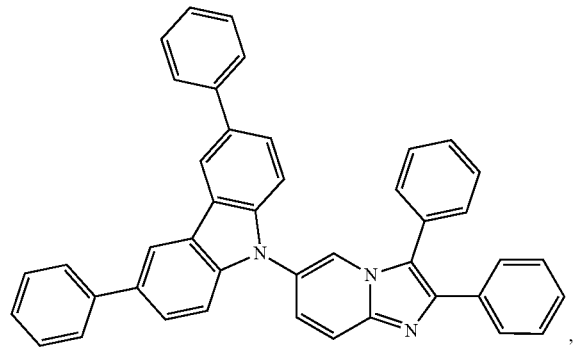
Compound 6
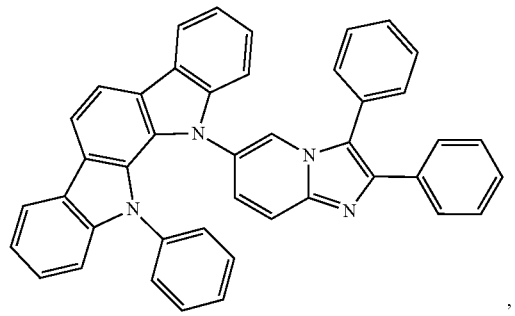
Compound 7
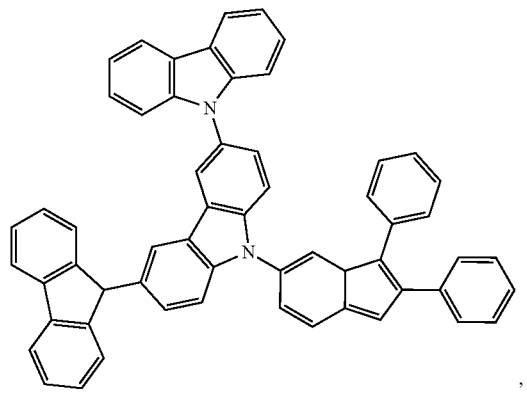
Compound 8
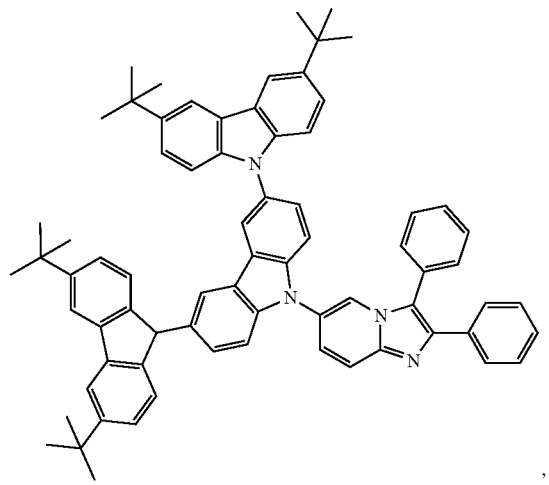
Compound 9
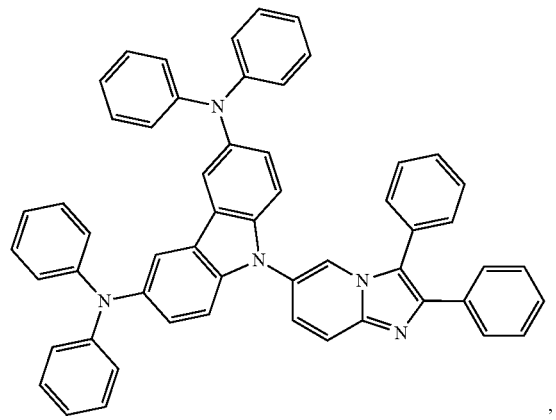
Compound 10
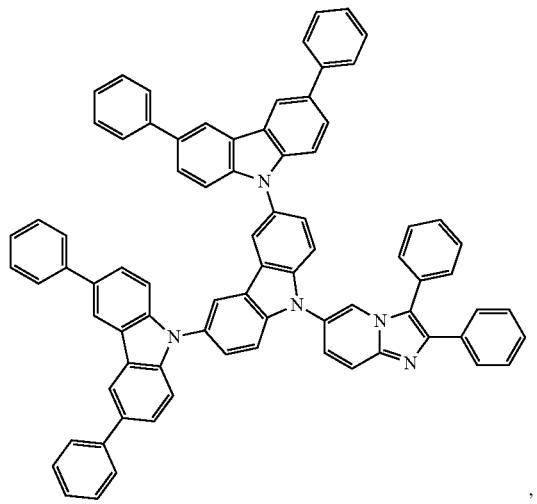

-continued
Compound 11
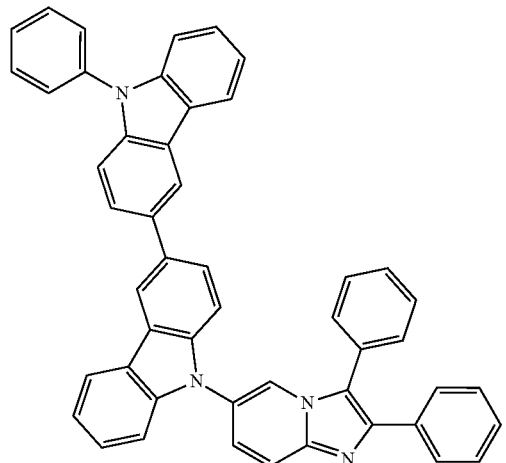
Compound 12
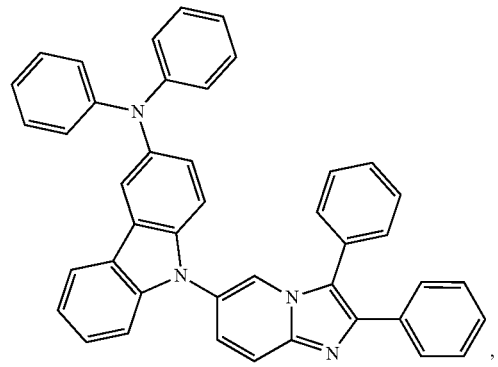
Compound 13
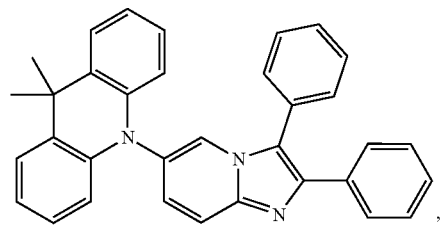
Compound 14
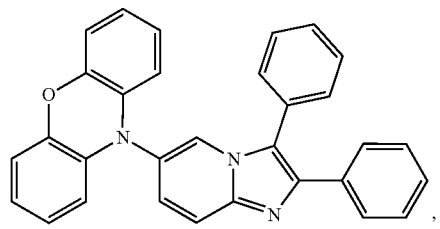
Compound 15
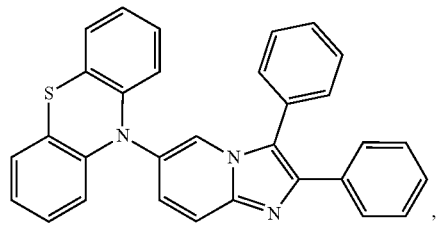
Compound 16
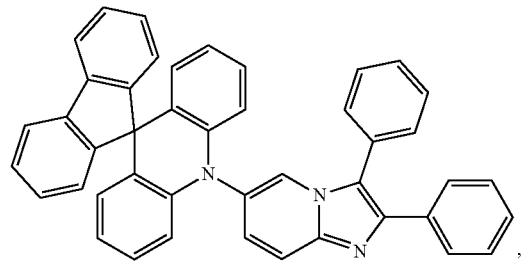
Compound 17
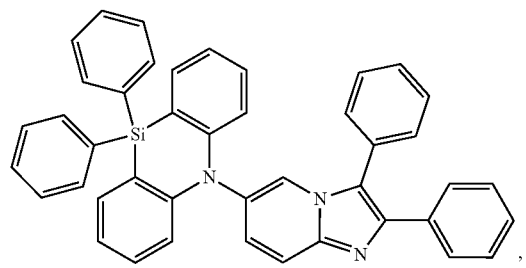
Compound 18
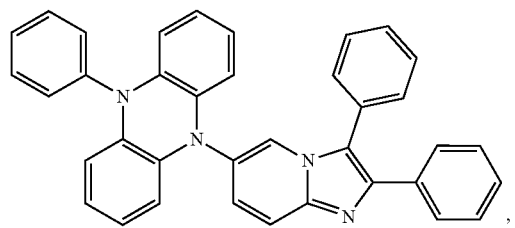
Compound 19
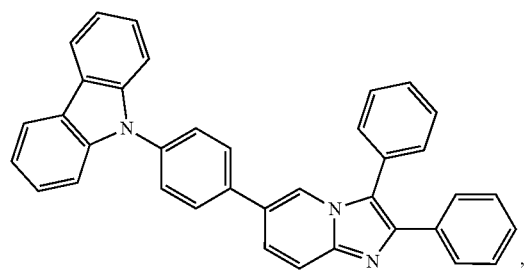
Compound 20
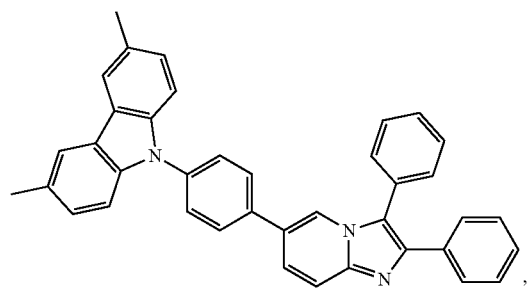

-continued
Compound 21
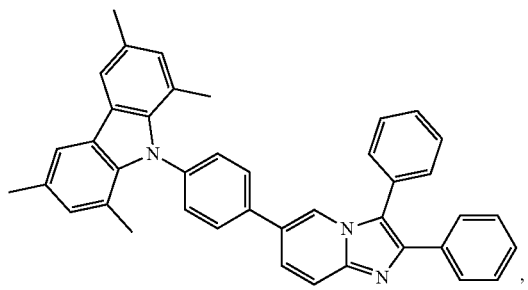
Compound 22
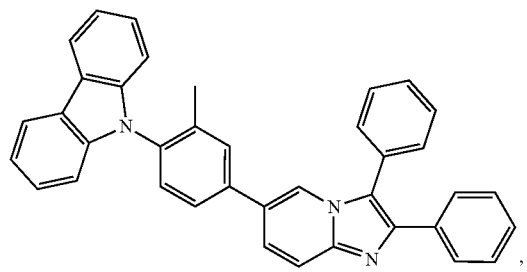
Compound 23
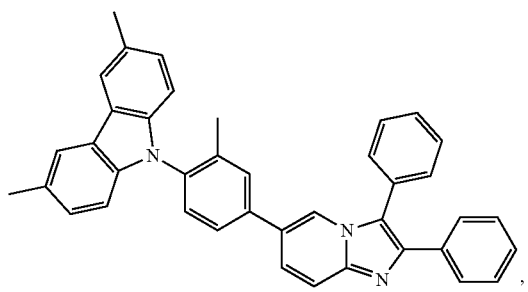
Compound 24
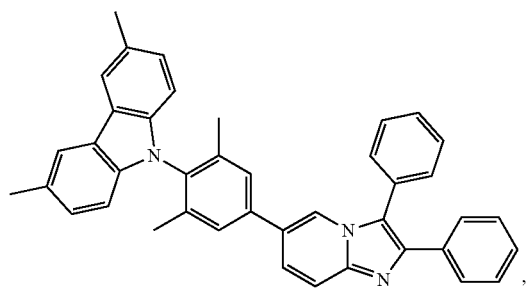
Compound 25
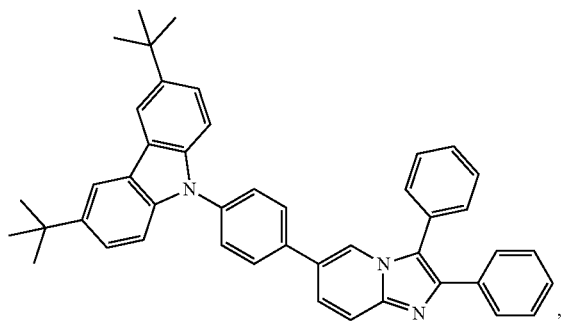
Compound 26
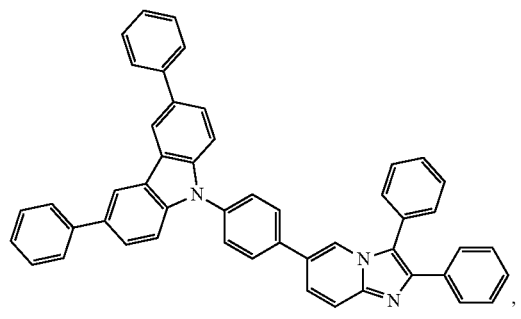
Compound 27
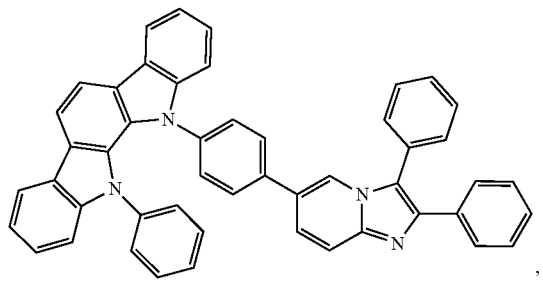
Compound 28
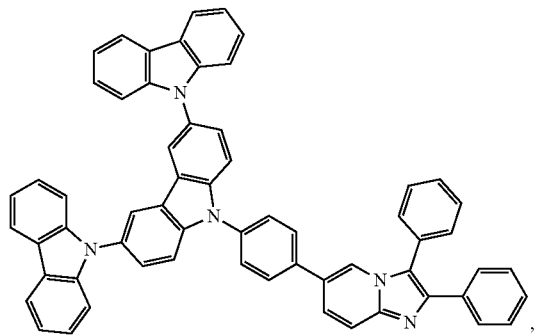

Compound 29
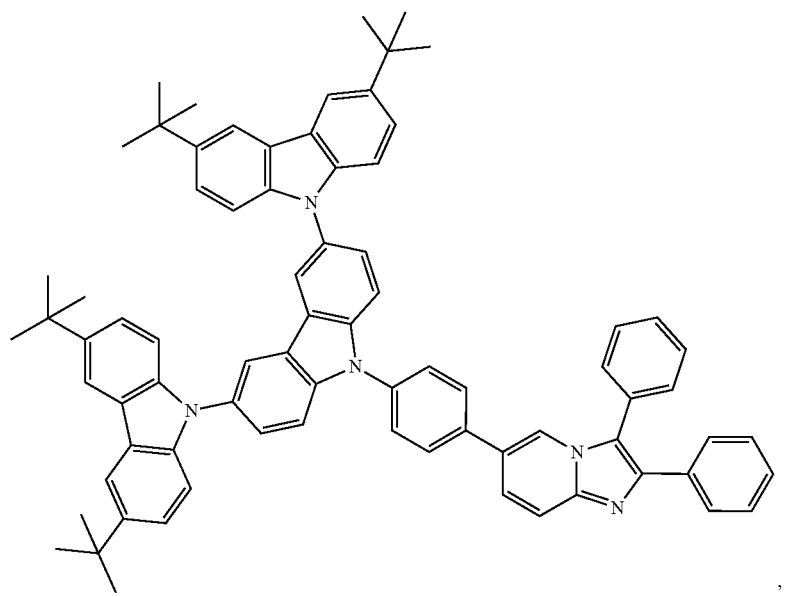
Compound 30
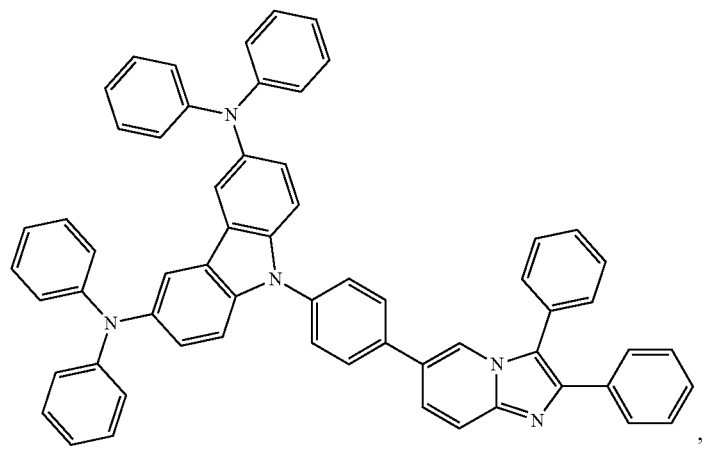

Compound 31
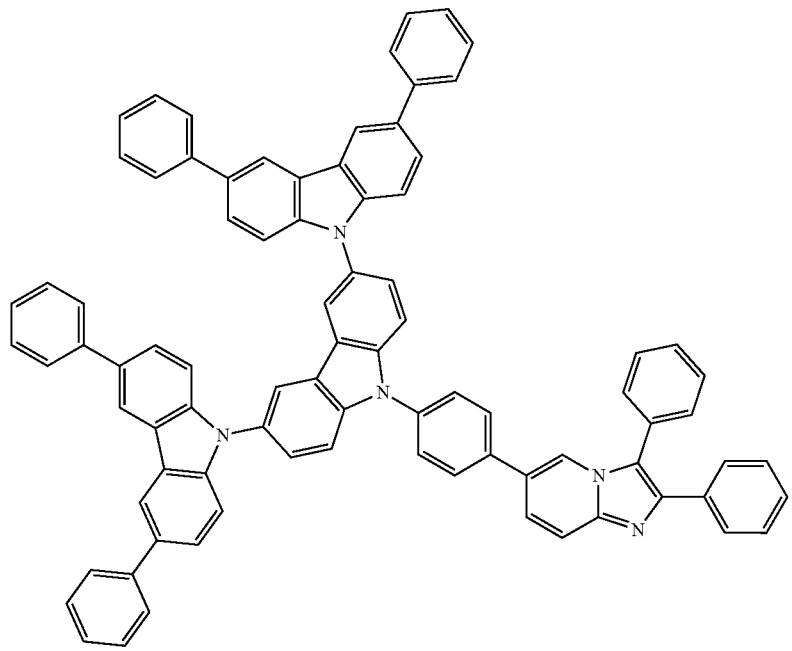
Compound 32
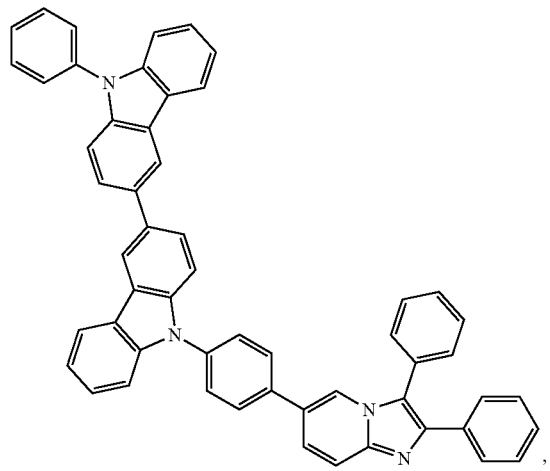
Compound 33
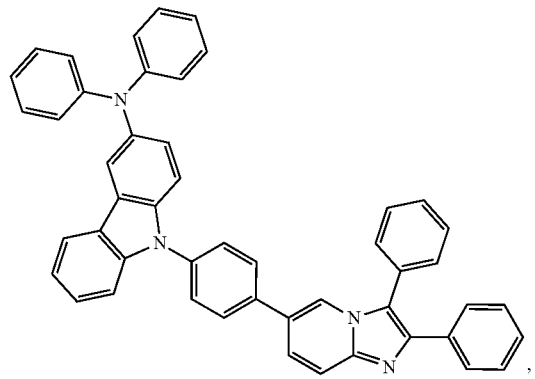
Compound 34
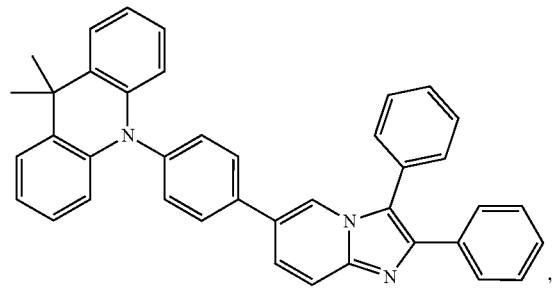
Compound 35
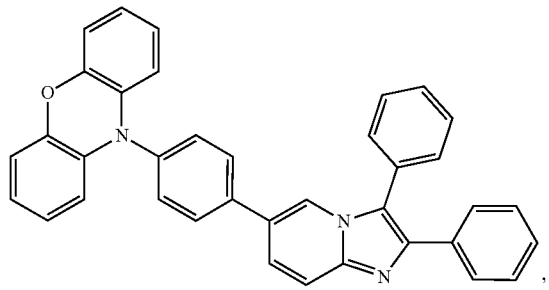

-continued
Compound 36
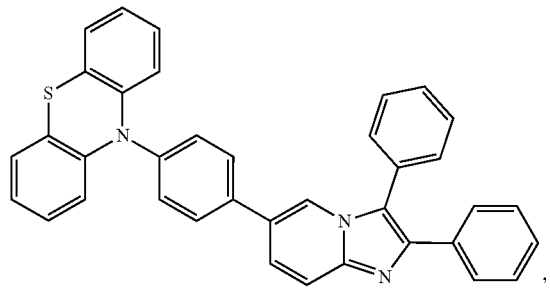
Compound 37
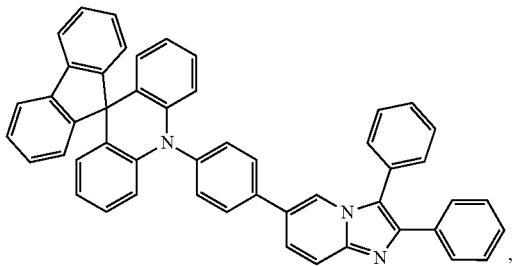
Compound 38
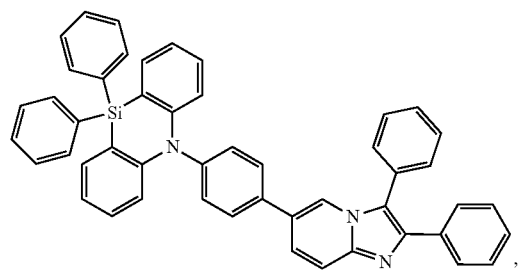
Compound 39
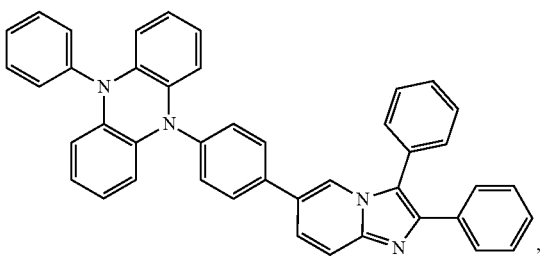
Compound 40
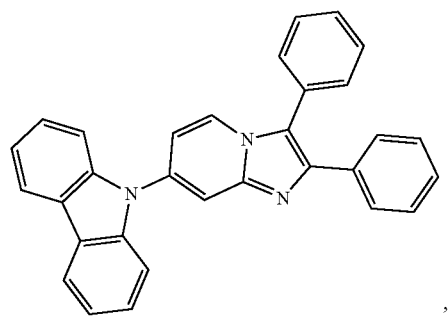
Compound 41
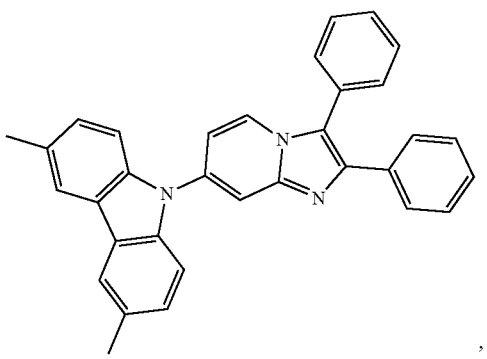
Compound 42
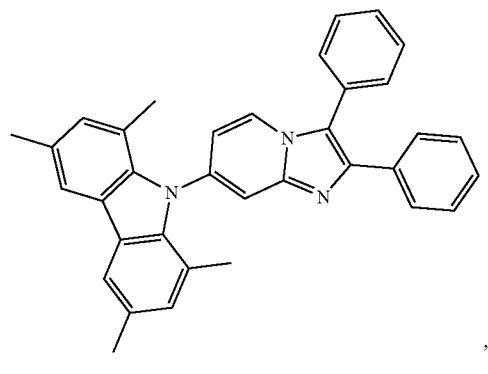
Compound 43
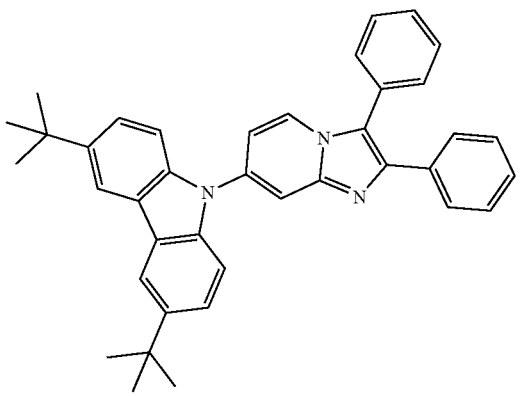

Compound 44
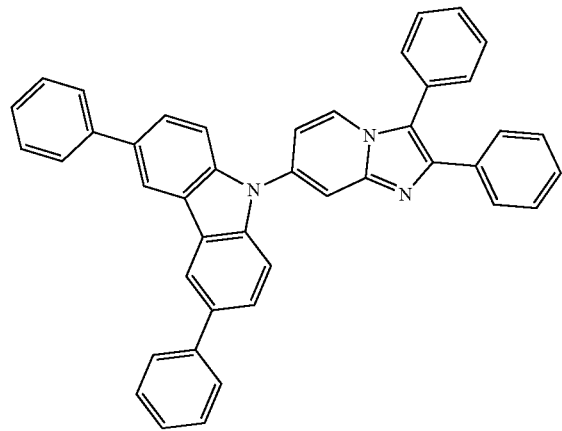
Compound 45
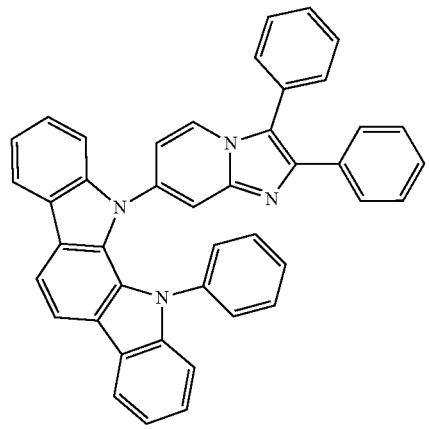
,
Compound 46
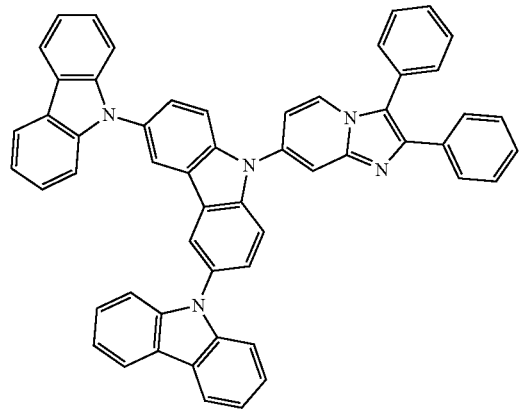
Compound 47
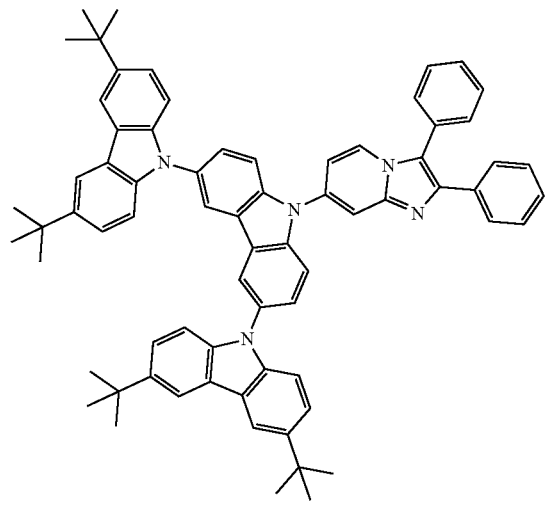
,
Compound 48
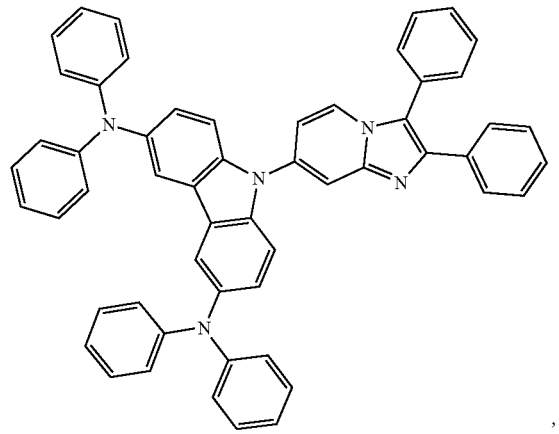
Compound 49
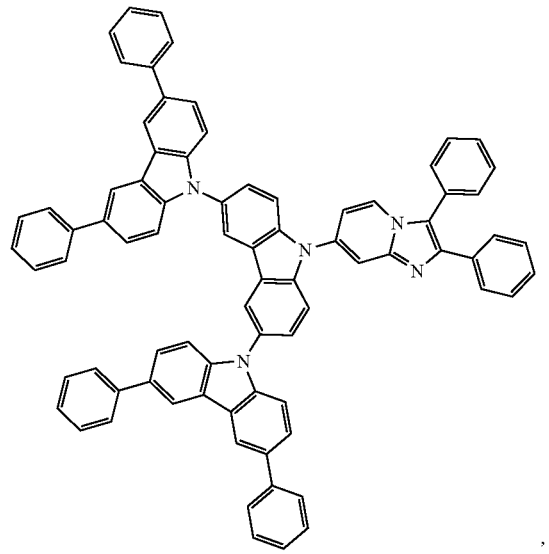
, -continued
Compound 50
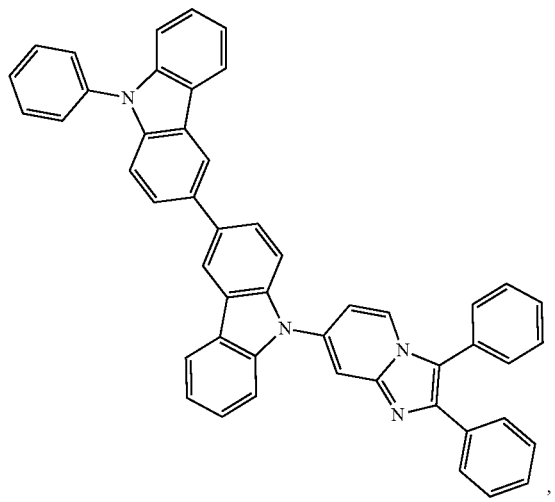
Compound 51
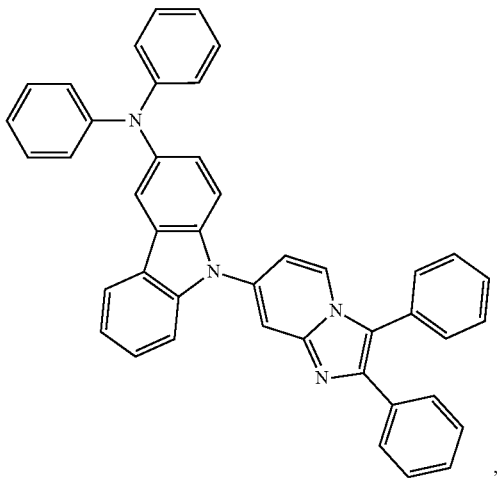
Compound 52
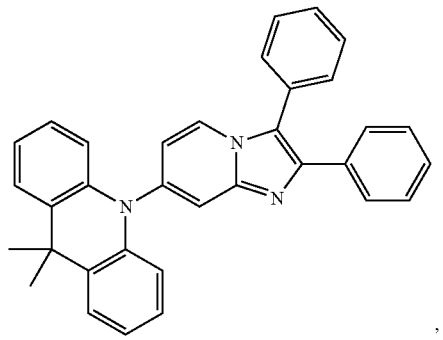
Compound 53
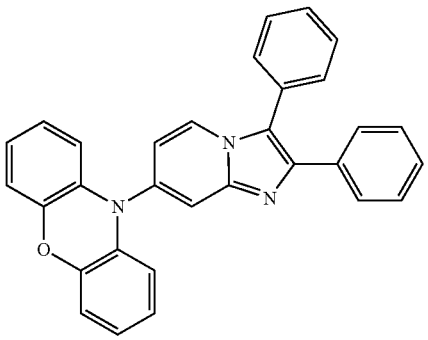
Compound 54
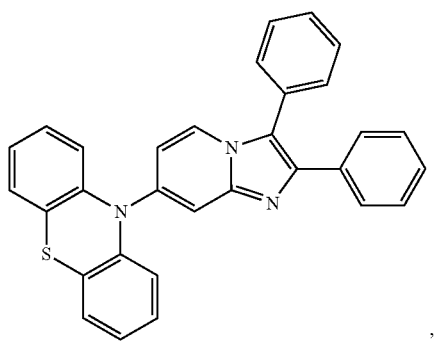
Compound 55
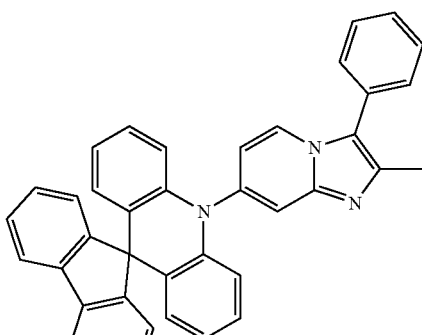
Compound 56
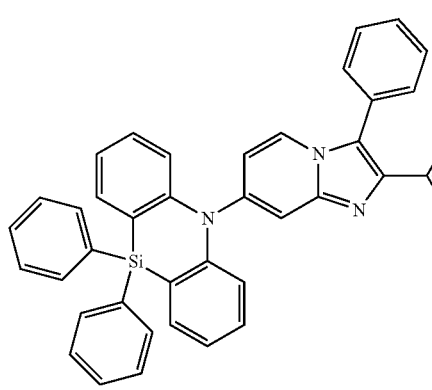
Compound 57
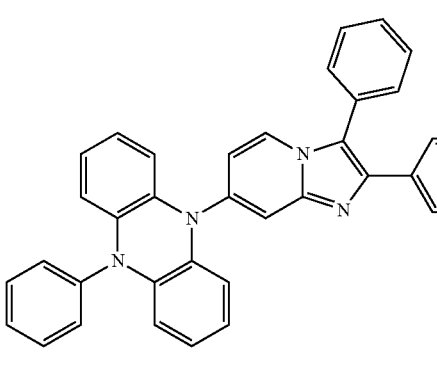

-continued
Compound 58
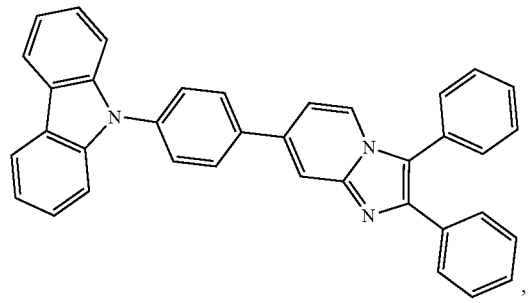
Compound 59
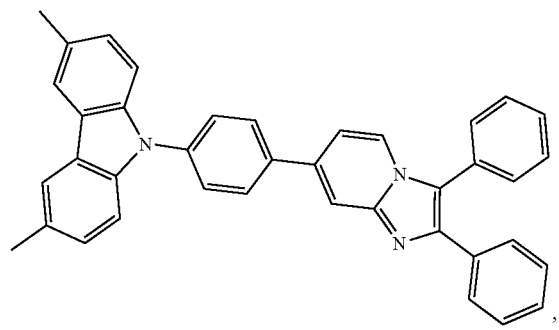
Compound 60
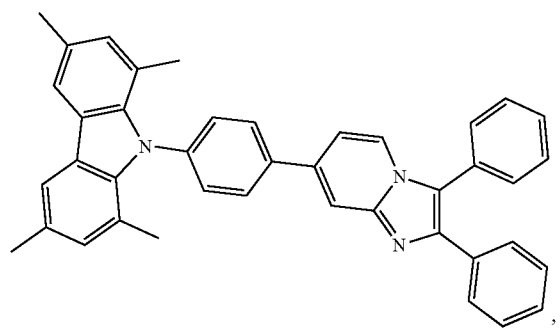
Compound 61
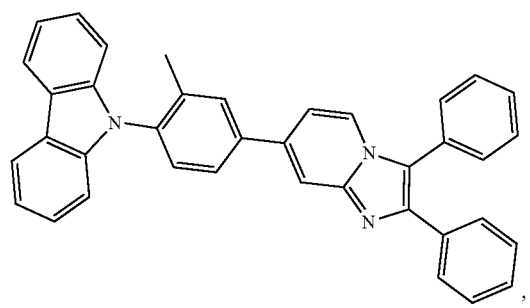
Compound 62
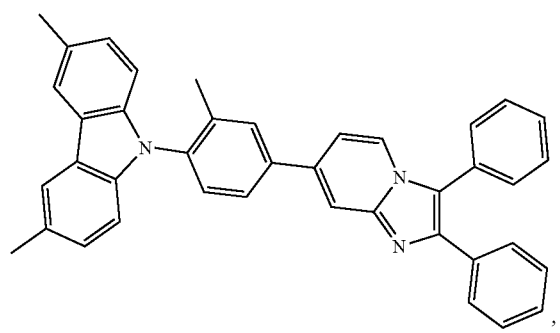
Compound 63
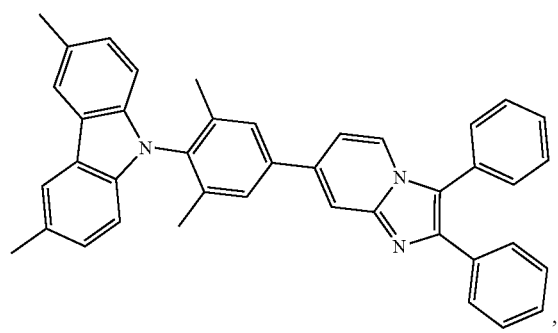
Compound 64
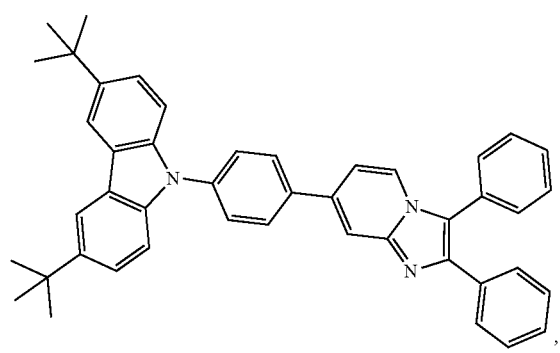
Compound 65
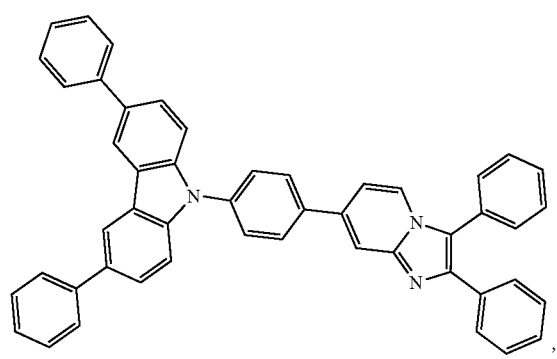

-continued
Compound 66
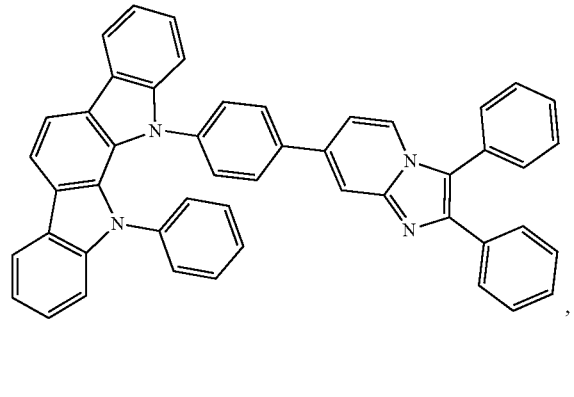
Compound 67
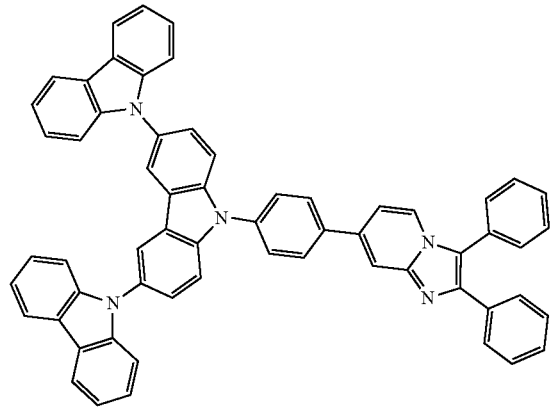
Compound 68
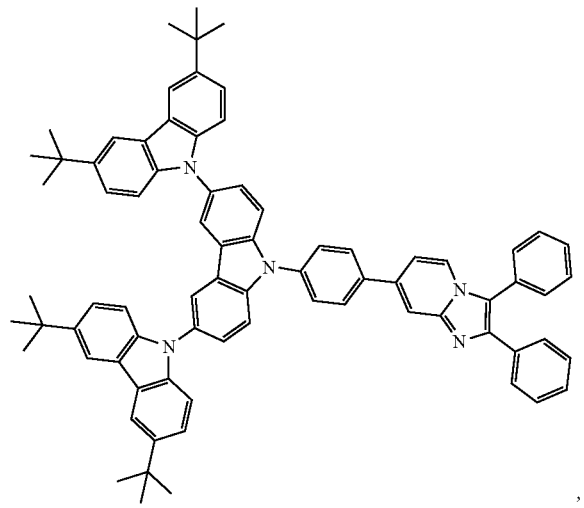
Compound 69
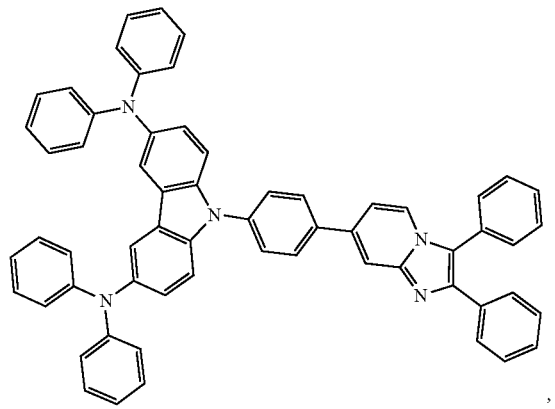
Compound 70
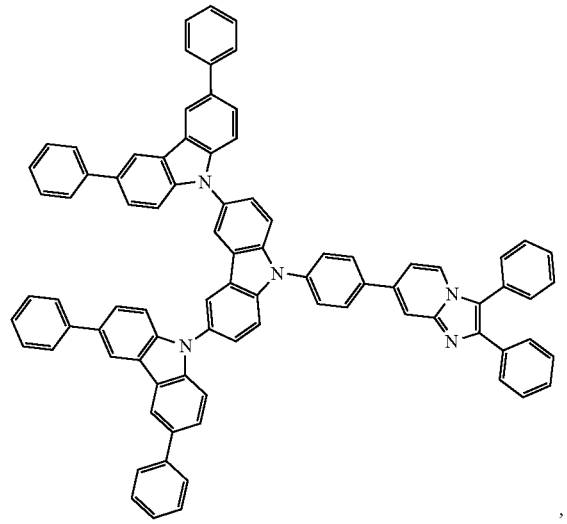
Compound 71
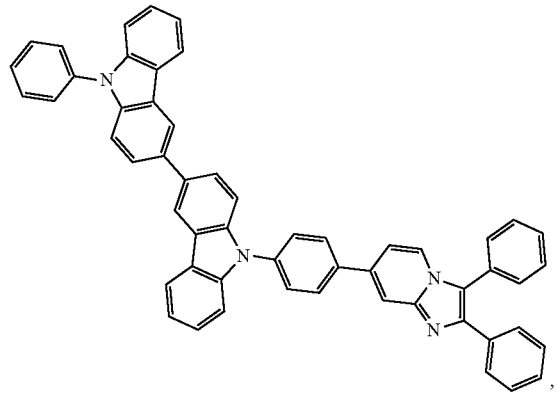

-continued
Compound 72
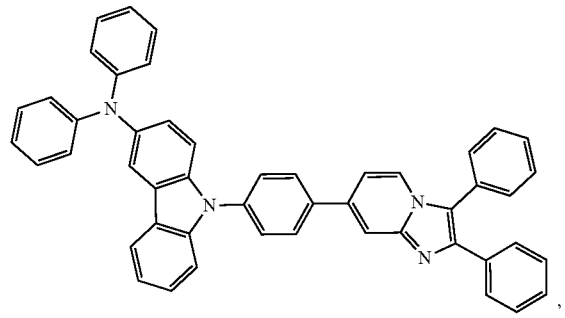
Compound 73
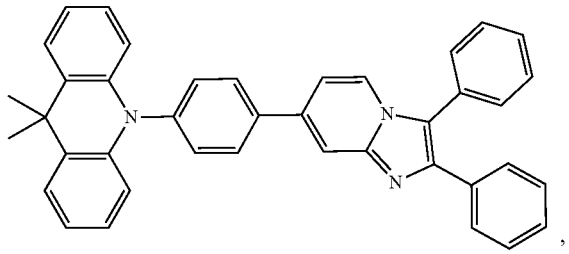
Compound 74
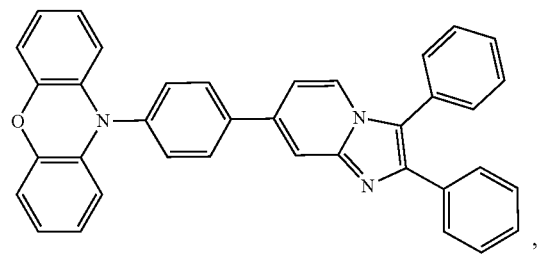
Compound 75
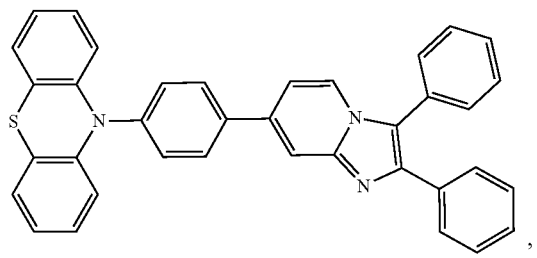
Compound 76
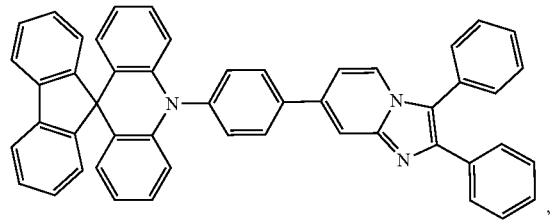
Compound 77
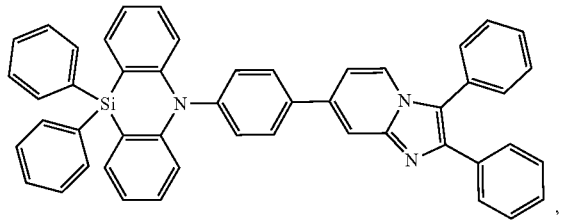
Compound 78
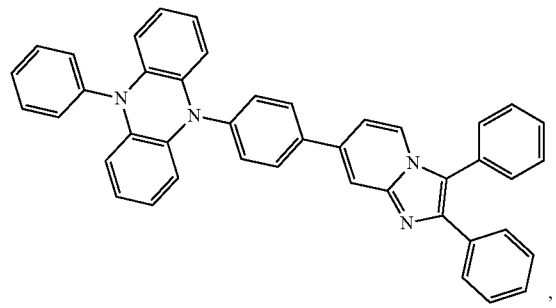
Compound 79
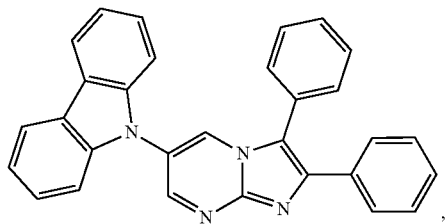
Compound 80
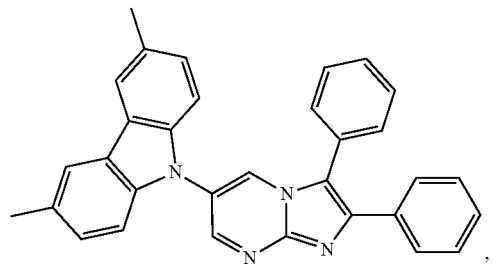
Compound 81
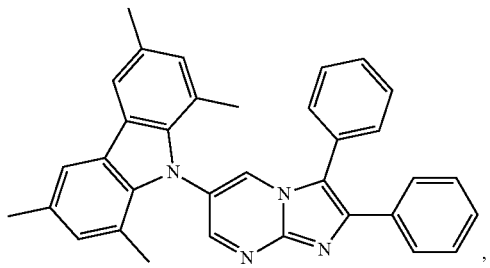

-continued
Compound 82
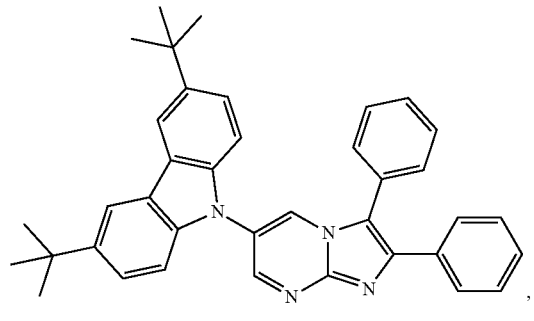
Compound 83
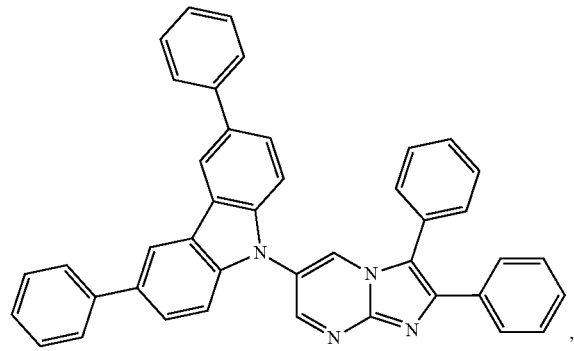
Compound 84
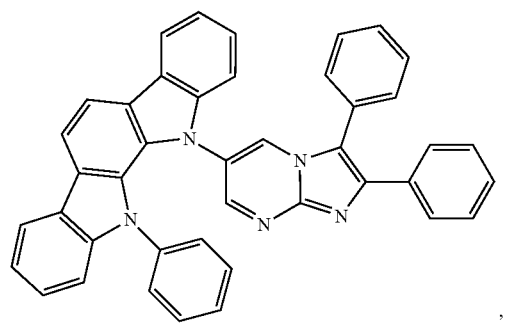
Compound 85
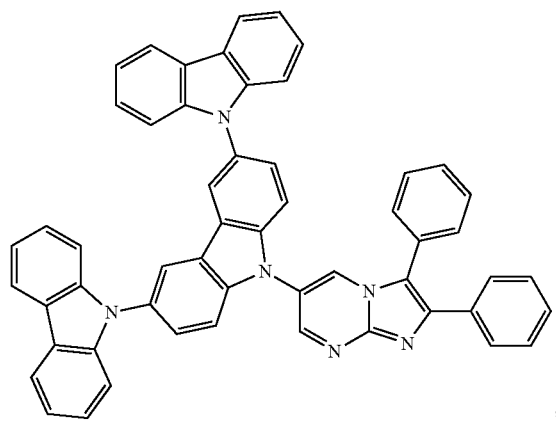
Compound 86
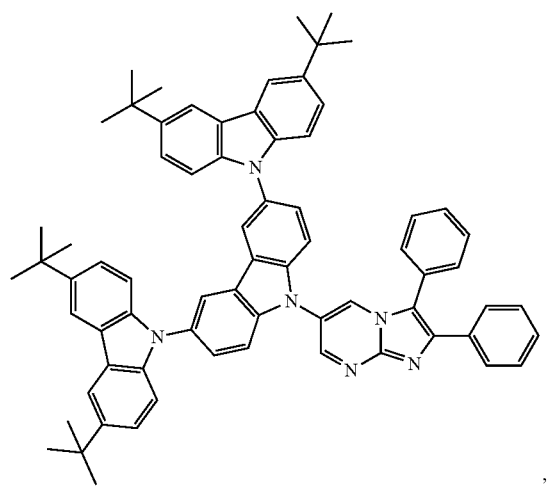
Compound 87
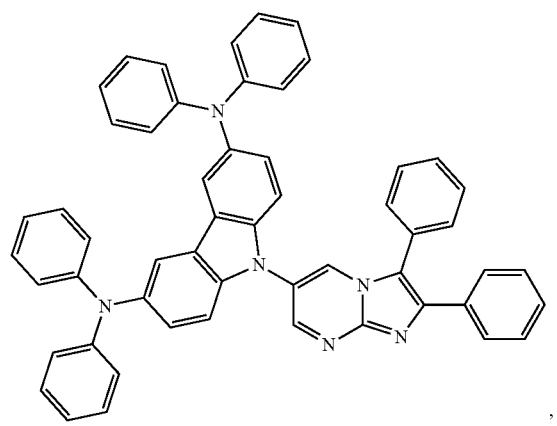

-continued
Compound 88
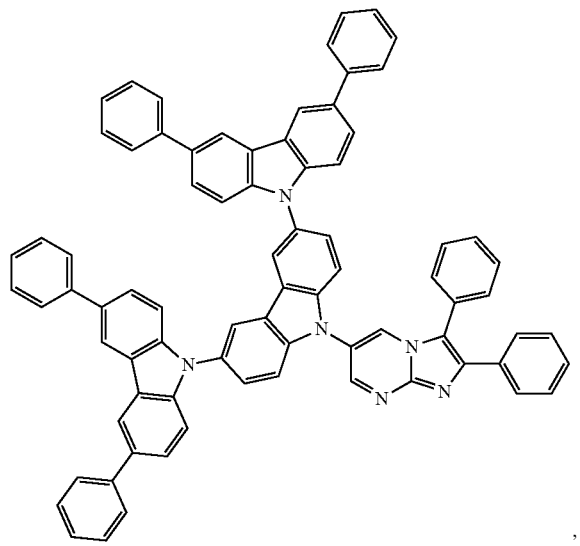
Compound 89
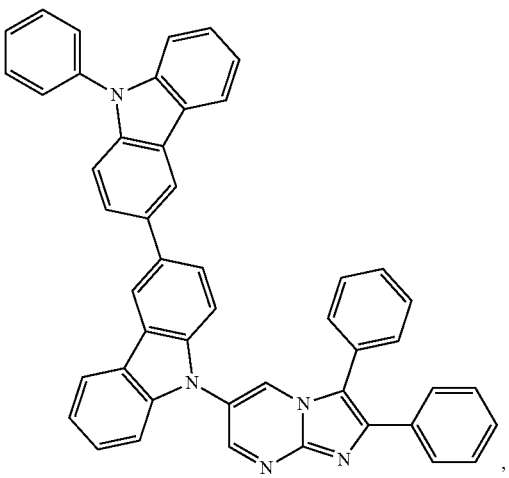
Compound 90
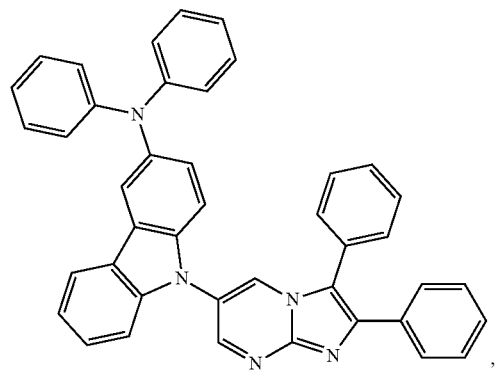
Compound 91
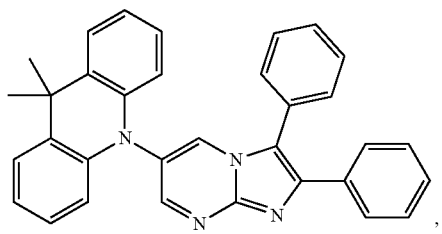
Compound 92
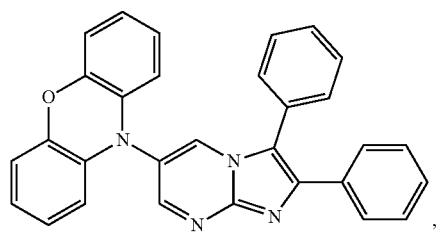
Compound 93
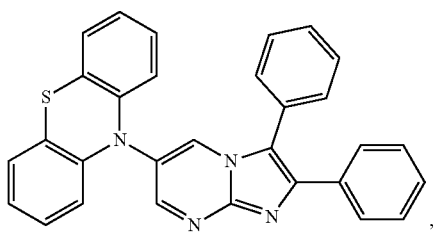
Compound 94
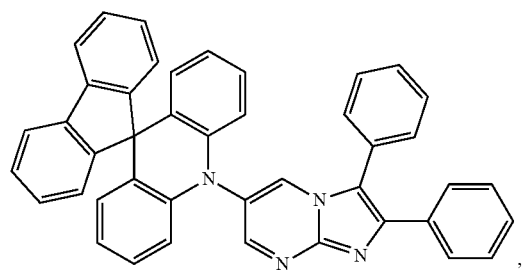
Compound 95
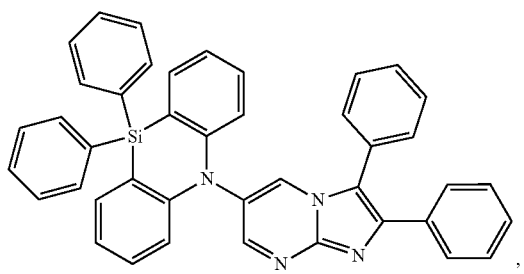

-continued
Compound 96
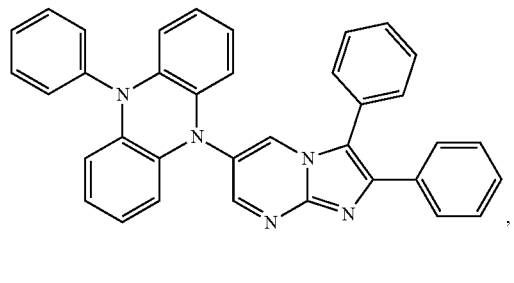
Compound 97
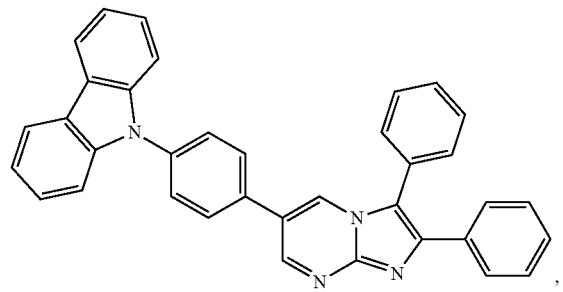
Compound 98
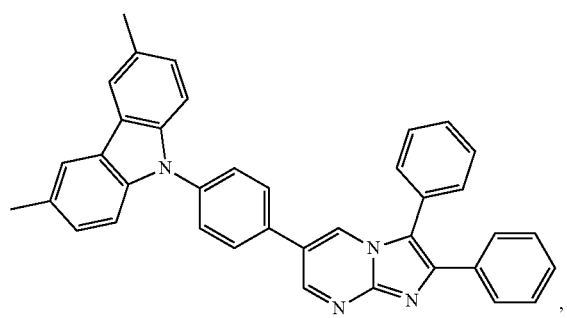
Compound 99
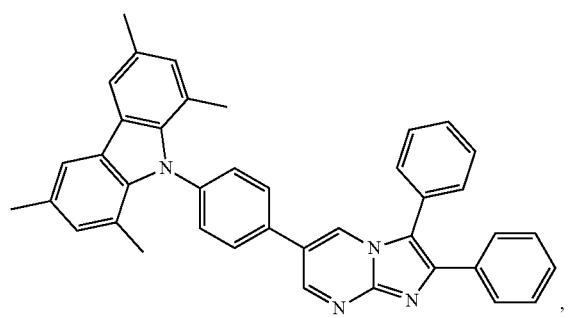
Compound 100
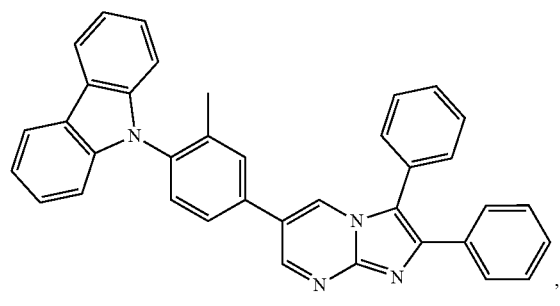
Compound 101
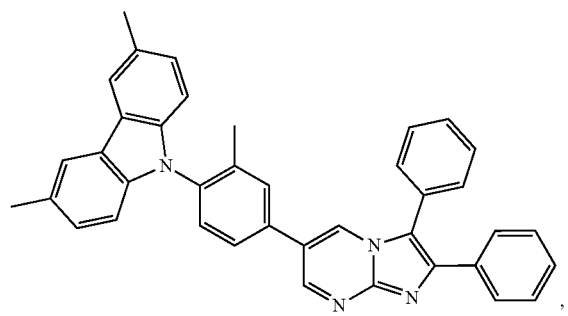
Compound 102
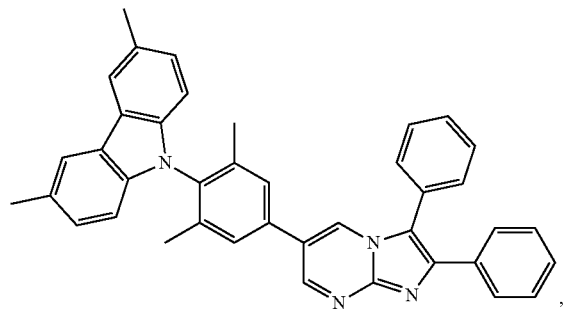
Compound 103
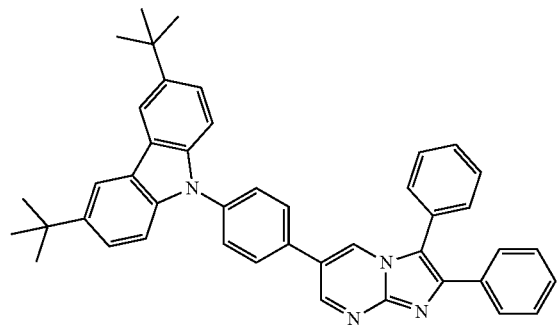

Compound 104
Compound 105
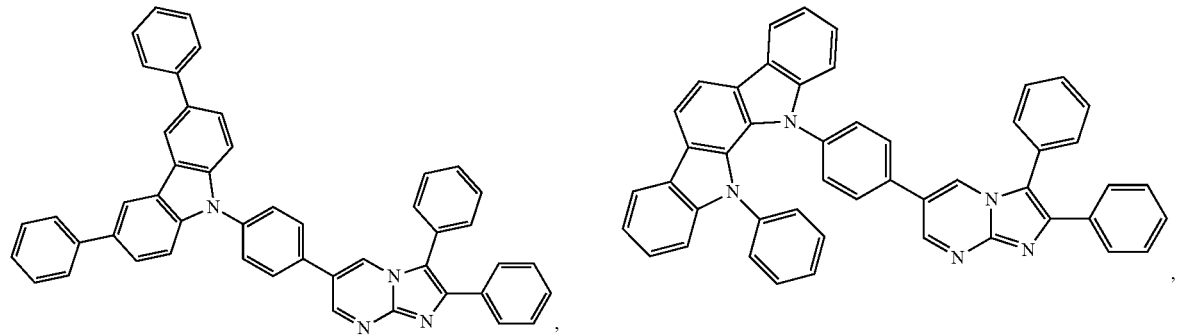
Compound 106
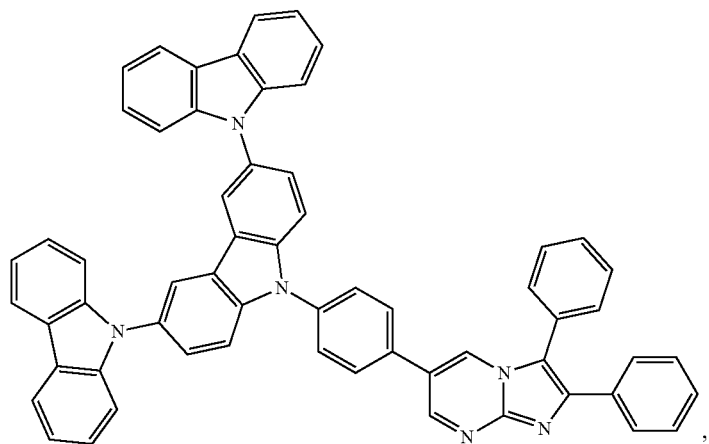
Compound 107
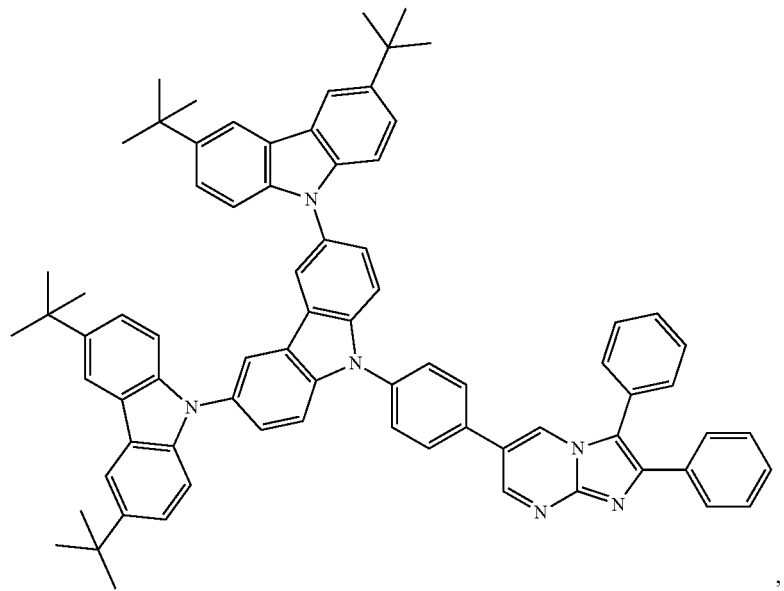

Compound 108
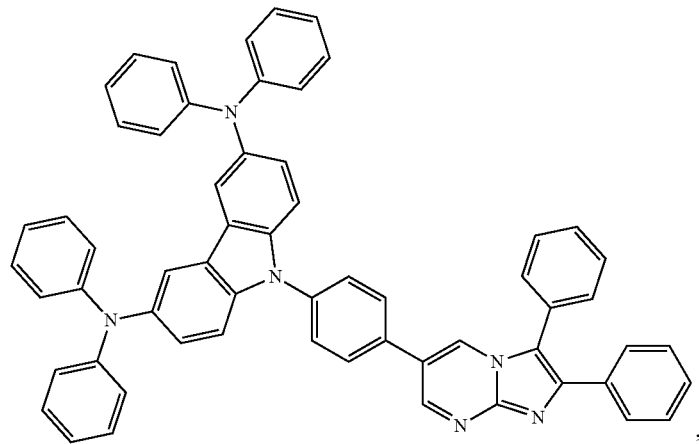
Compound 109
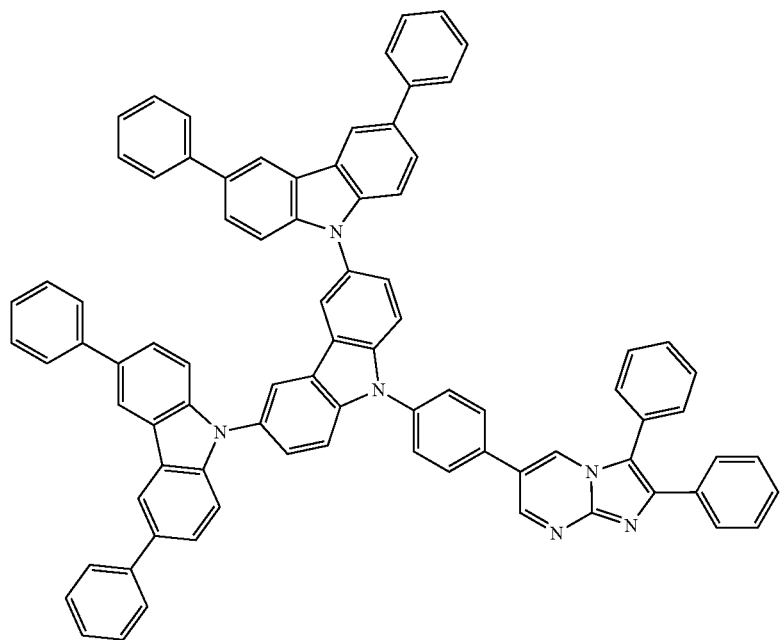
Compound 110
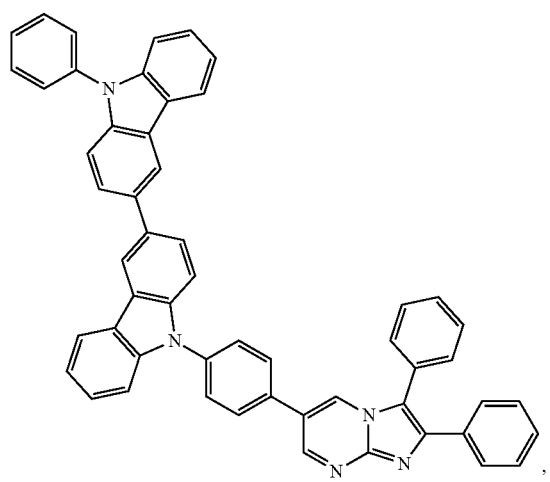
Compound 111
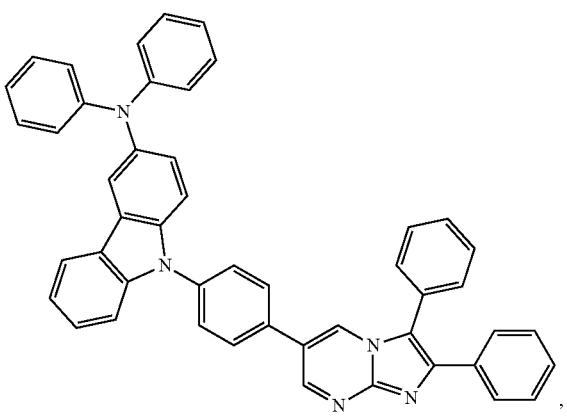

-continued
Compound 112
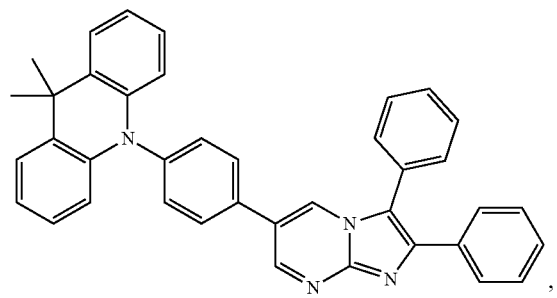
Compound 113
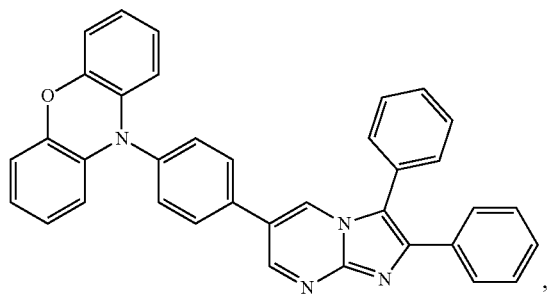
Compound 114
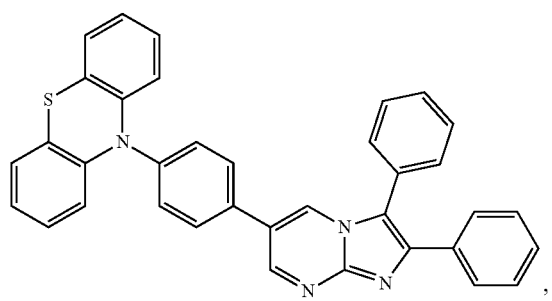
Compound 115
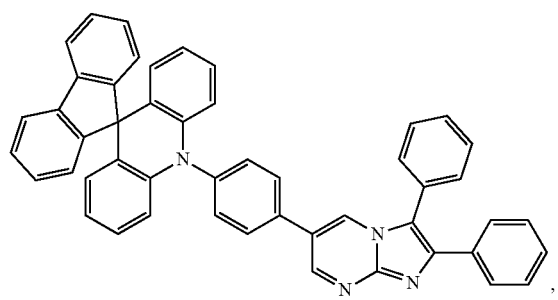
Compound 116
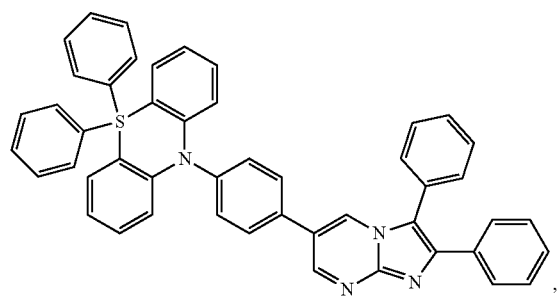
Compound 117
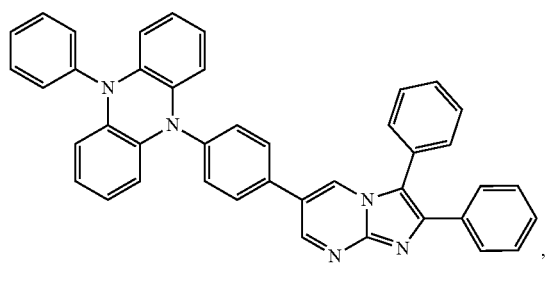
Compound 118
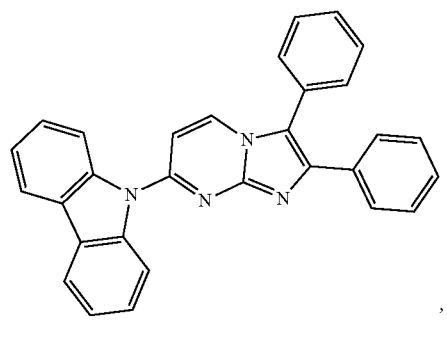
Compound 119
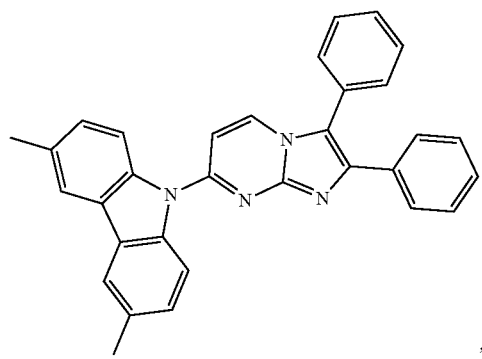

-continued
Compound 120
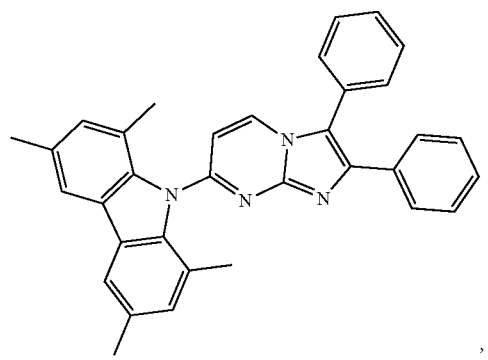
Compound 121
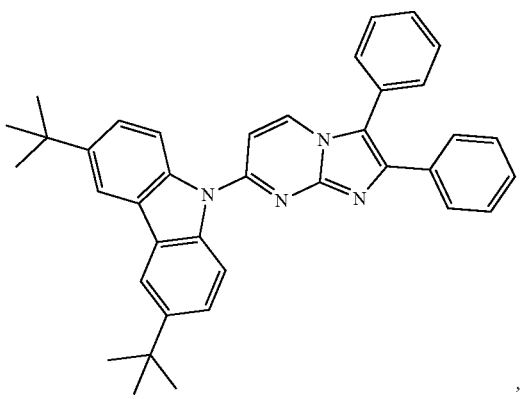
Compound 122
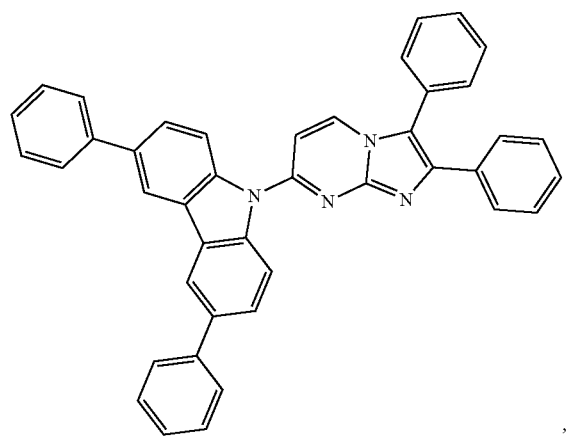
Compound 123
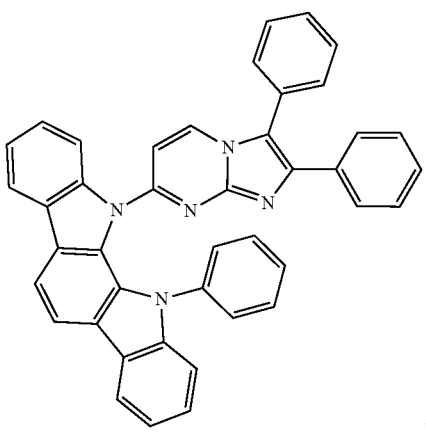
Compound 124
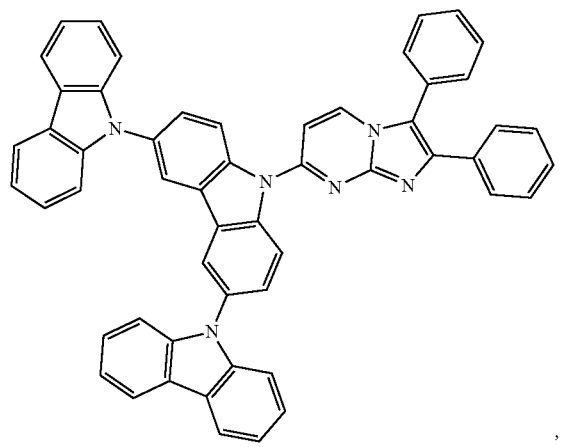
Compound 125
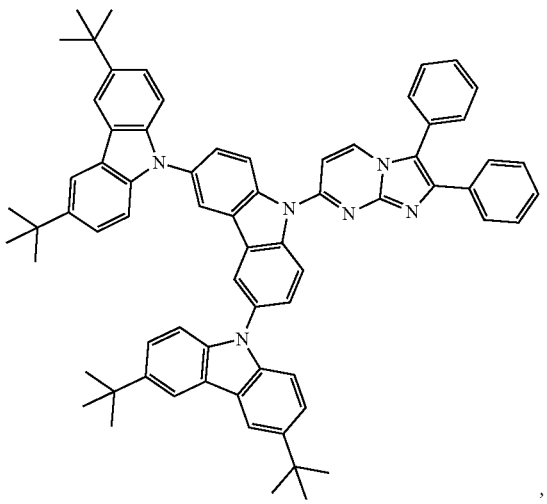

-continued
Compound 126
Compound 127
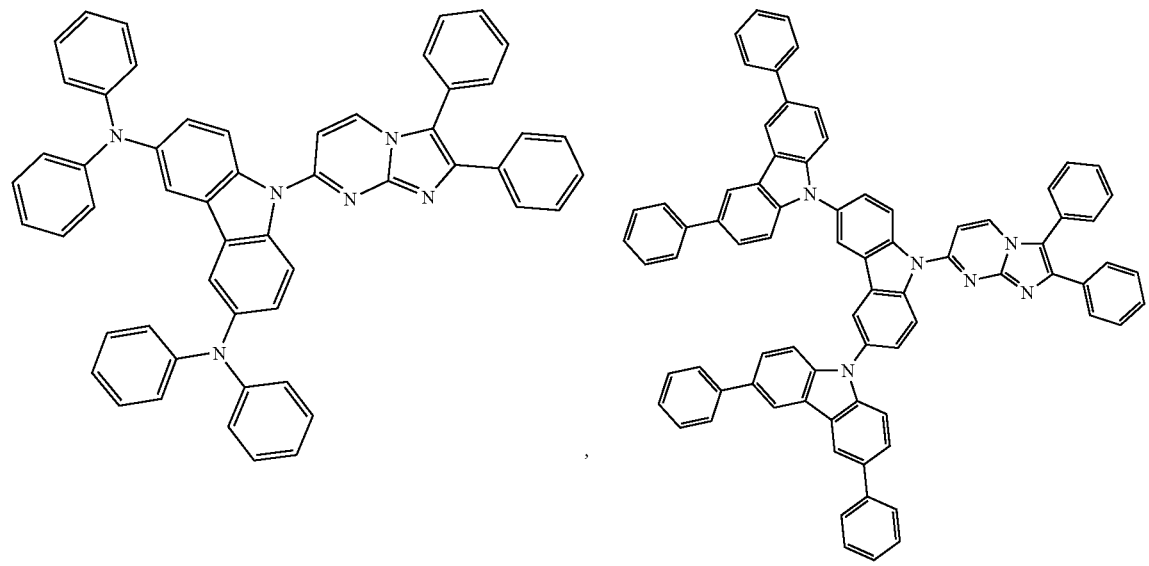
Compound 128
Compound 129
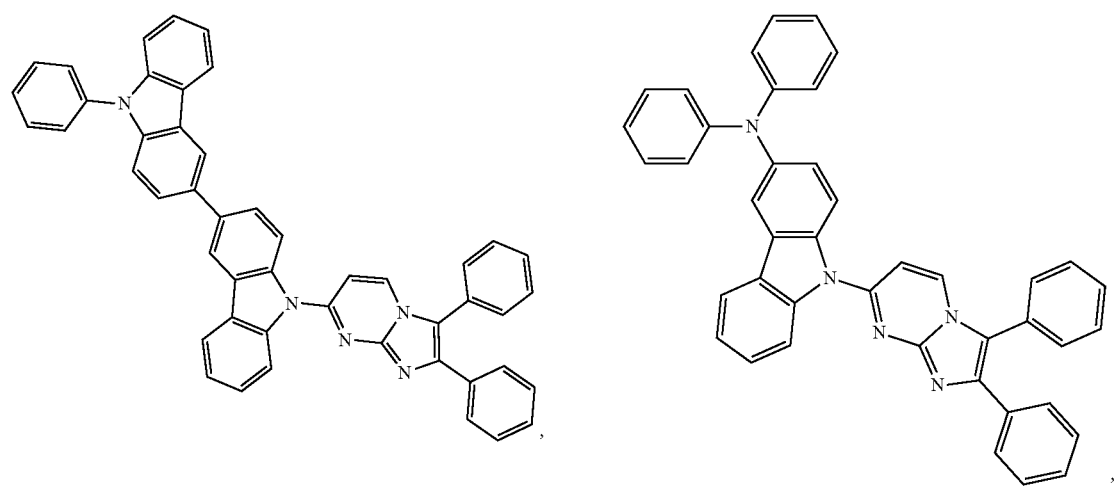
Compound 130
Compound 131
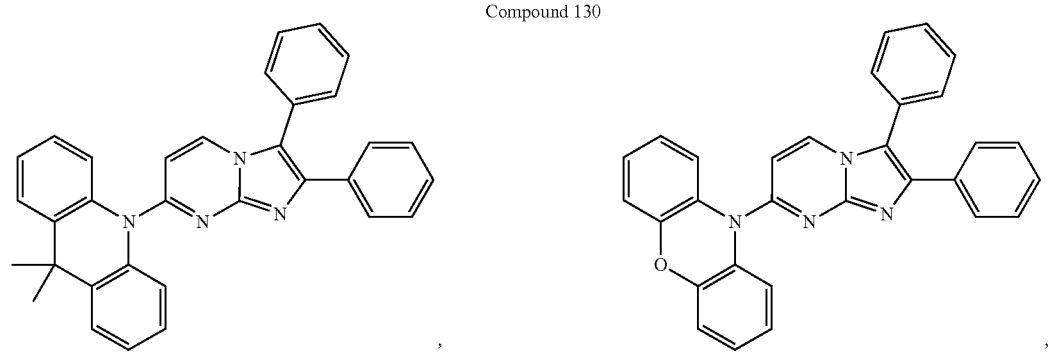

-continued
Compound 132
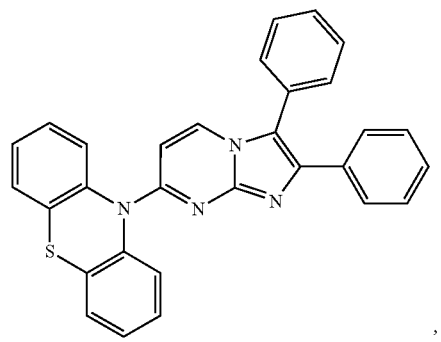
Compound 133
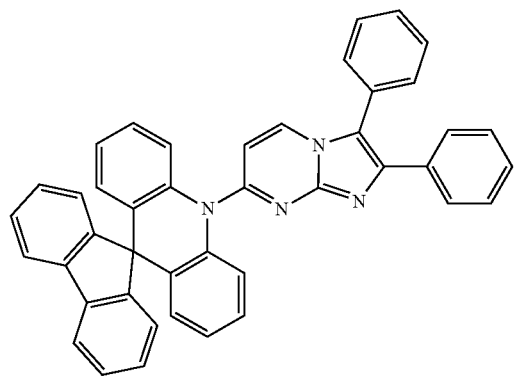
Compound 134
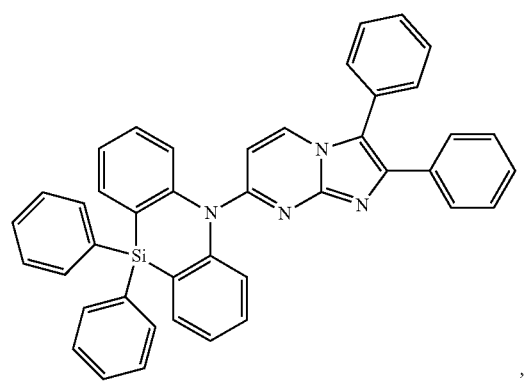
Compound 135
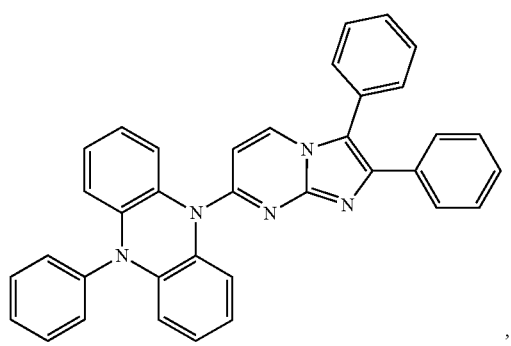
Compound 136
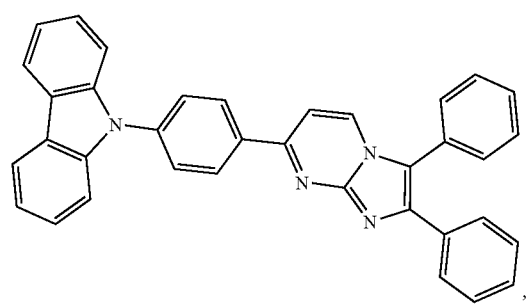
Compound 137
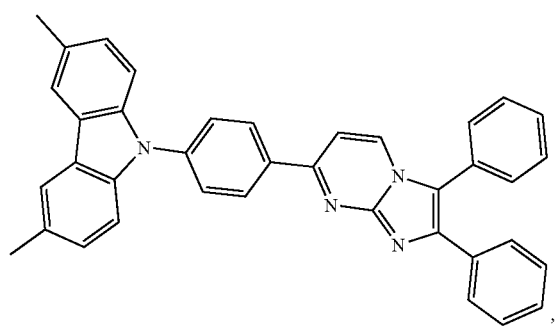
Compound 138
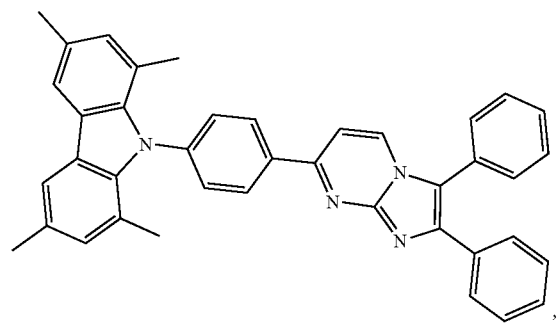
Compound 139
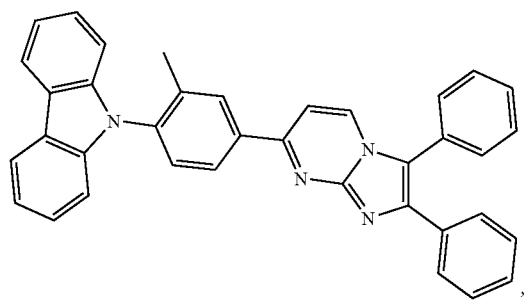

-continued
Compound 140
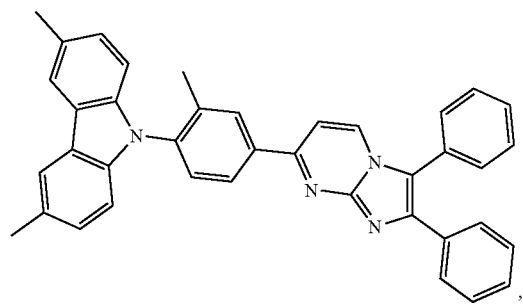
Compound 141
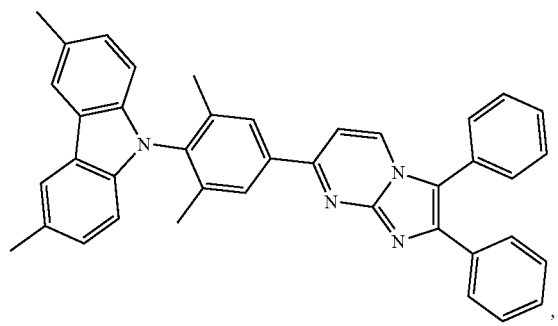
Compound 142
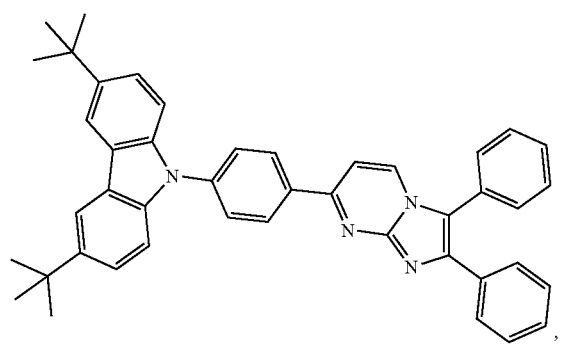
Compound 143
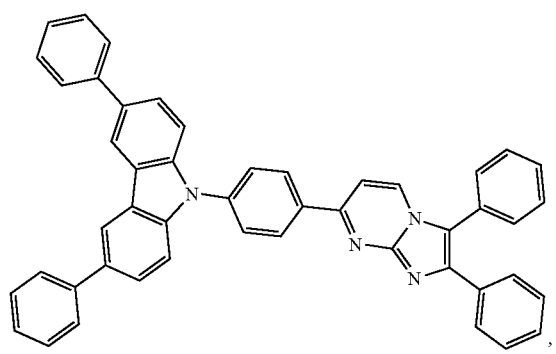
Compound 144
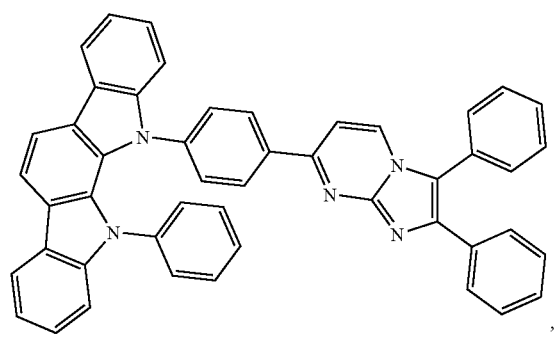
Compound 145
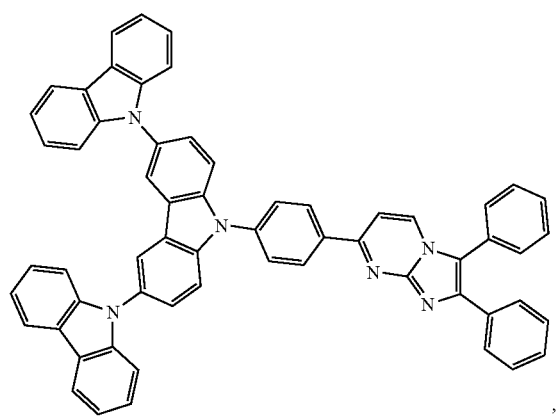

-continued
Compound 146 | Compound 147
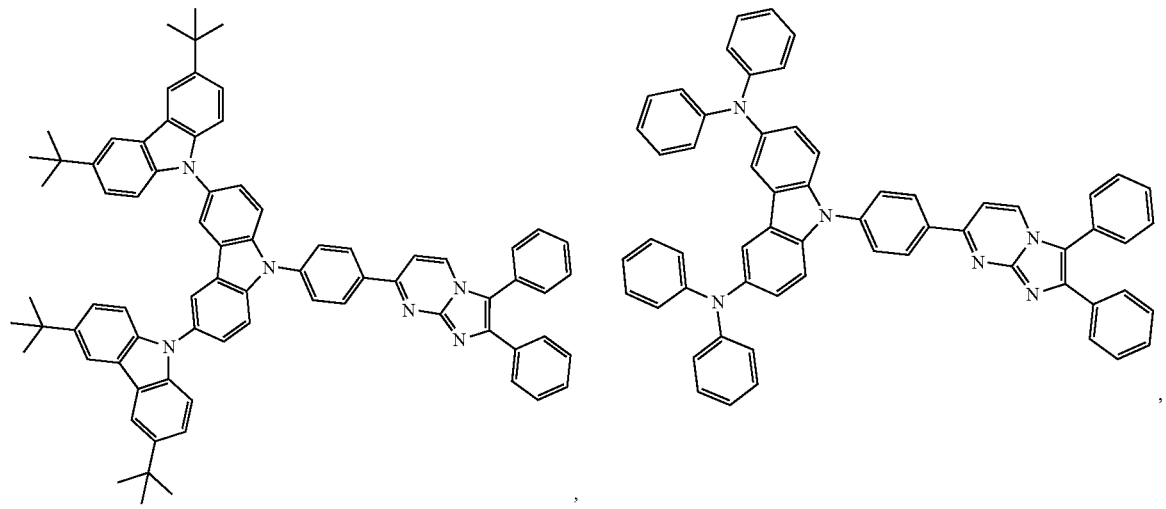
Compound 148 | Compound 149
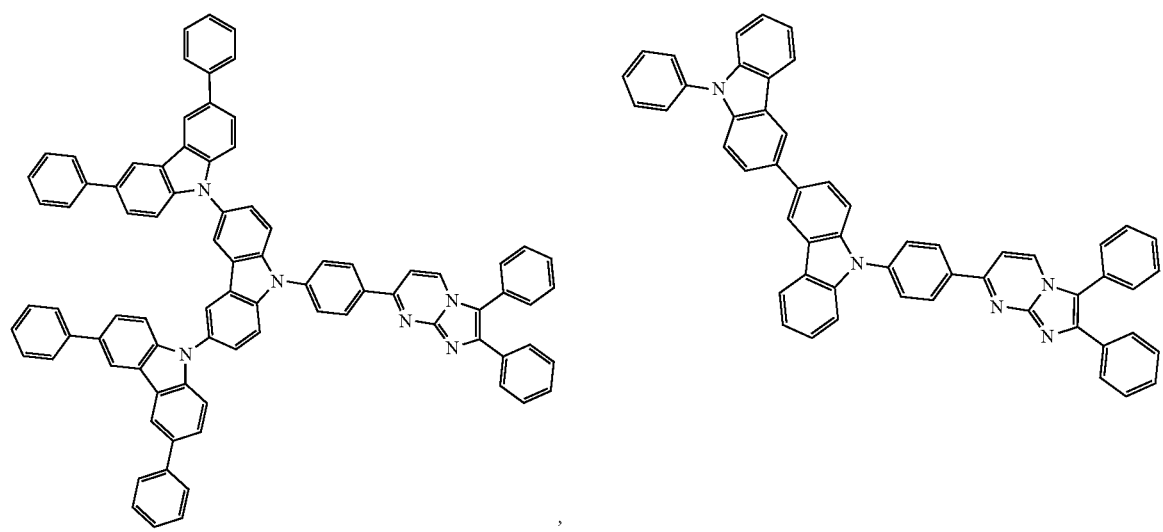
Compound 150 | Compound 151
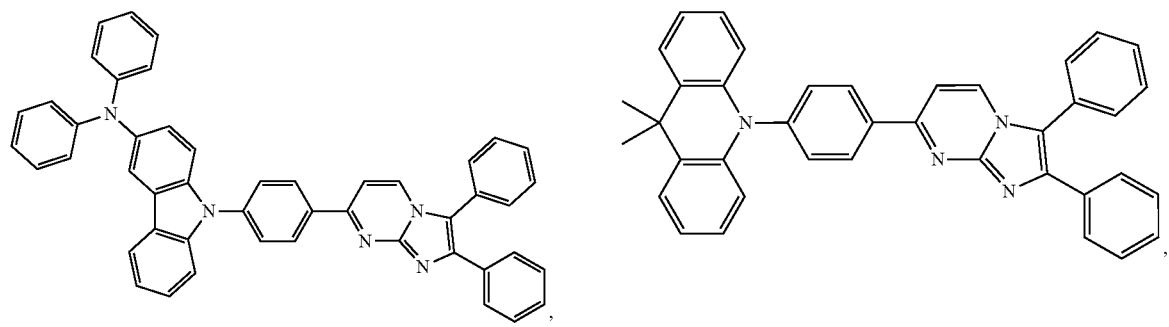

-continued

Compound 152

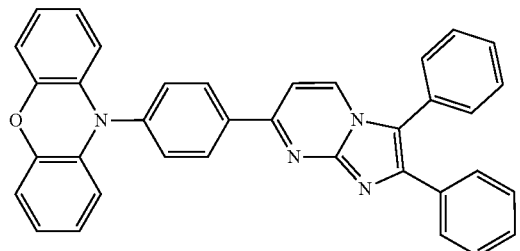

Compound 153

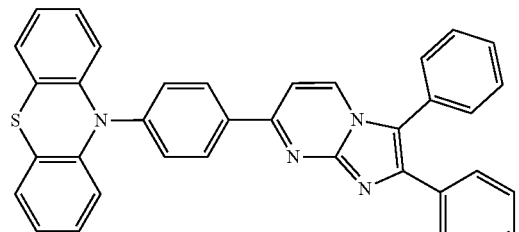

Compound 154

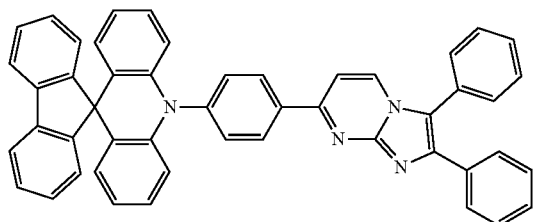

Compound 155

Compound 156

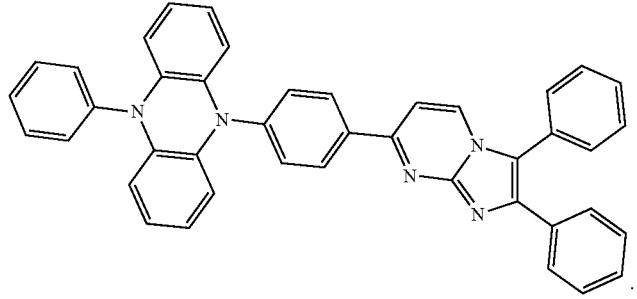

7. An organic electroluminescent device, comprising an anode and a cathode which are oppositely arranged, and an organic functional layer disposed between the anode and the cathode, wherein the organic functional layer comprises a plurality of organic layers, and wherein at least one of the organic layers contains one or more nitrogen-containing heterocyclic organic compounds according to claim 1.

8. The organic electroluminescent device according to claim 7, wherein the plurality of organic layers comprise at least one layer of a hole injection layer, a hole transport layer, an electron blocking layer, a light emitting layer, a hole blocking layer, an electron transport layer, and an electron injection layer.

9. The organic electroluminescent device according to claim 7, wherein the organic layers in the organic functional layer are formed by vacuum evaporation, molecular beam epitaxy, spin coating, dip coating, bar coating, or inkjet printing, and wherein the anode and the cathode are both formed by evaporation or sputtering.

10. The organic electroluminescent device according to claim 8, wherein the plurality of organic layers comprise the light emitting layer, and the light emitting layer comprises a host light emitting material and the nitrogen-containing heterocyclic organic compound according to claim 1.

* * * * *